US006277591B1

(12) United States Patent
Civelli et al.

(10) Patent No.: US 6,277,591 B1
(45) Date of Patent: Aug. 21, 2001

(54) DOPAMINE RECEPTORS AND GENES

(75) Inventors: Olivier Civelli; James R. Bunzow; David K. Grandy; Curtis A. Machida, all of Portland, OR (US)

(73) Assignee: Oregon Health Science University, Portland, OR (US)

( * ) Notice: Subject to any disclaimer, the term of this patent is extended or adjusted under 35 U.S.C. 154(b) by 0 days.

(21) Appl. No.: 08/480,390

(22) Filed: Jun. 7, 1995

Related U.S. Application Data

(63) Continuation of application No. 07/973,588, filed on Nov. 9, 1992, now abandoned, which is a continuation of application No. 07/438,544, filed on Nov. 20, 1989, now abandoned, which is a continuation-in-part of application No. 07/273,373, filed on Nov. 18, 1988, now abandoned.

(51) Int. Cl.[7] .......................... C07K 14/705; C12N 5/10; C12N 15/12

(52) U.S. Cl. ................. 435/69.1; 435/172.3; 435/252.3; 435/320.1; 530/350; 536/23.5

(58) Field of Search ................................. 435/6, 7.1, 7 R, 435/252.3, 64.1, 320.1, 172.3; 530/350; 536/23.5

(56) References Cited

U.S. PATENT DOCUMENTS

| 4,675,285 | * | 6/1987 | Clark et al. ............................... 435/6 |
| 4,705,858 | | 11/1987 | Hadley . |
| 4,736,866 | | 4/1988 | Leder et al. . |

OTHER PUBLICATIONS

Casey et al., Nucleic Acids Research, vol. 4, No. 5, pp. 1539–1552 (Dec. 24, 1976).

Dixon et al., Nature 321:75–79 (May 1, 1986).

Krust et al., EMBO J., 5:891–897 (May 1986).

Kubo et al., Nature, 323:411–416 (Oct. 2, 1986).

Kobilka et al., J.B.C., 262(15), pp. 7321–7327 (May 25, 1987).

Kobilka et al., Nature, 329:75–79 (Sep. 3, 1987).

Britten et al., Meth. in Enzymology, vol. 19, Part E, pp.363–418, "Analysis of Repeating DNA Sequences by Reassociation".

Grigoriadis et al., FEBs Let. 227:220–224 (Jan. 1988).

Sims et al., Science 241:585–589 (Jul. 29, 1988).

Hauptmann et al. *Nucleic Acids Research* 13(13): 4734–4749, 1985.*

* cited by examiner

Primary Examiner—John Ulm
(74) Attorney, Agent, or Firm—McDonnell Boehnen Hulbert & Berghoff

(57) ABSTRACT

A mammalian $D_2$ dopamine receptor gene has been cloned. Thus, DNA sequences encoding all or a part of the dopamine receptor are provided, as well as the corresponding polypeptide sequences and methods for producing the same both synthetically and via expression of a corresponding sequence from a host transformed with a suitable vector carrying the corresponding DNA sequence. The various structural information provided by this invention enables the preparation of labeled or unlabeled immunospecific species, particularly antibodies, as well as nucleic acid probes labeled in conventional fashion. Pharmaceutical compositions and methods of using various products of this invention are also provided.

48 Claims, 47 Drawing Sheets

FIG. 1A

```
                                                                    GGCTGCCGG
                                                                         -120
AGGGGCGGGCCGTGCCGTGGATGCGGGGAGCTGGAAGCCTCGAGCAGCCGGGCGCCTTCT
CTGGCCCCCGGCGCCATATGGCTTGAAGAGCCCCAGTGGCCCCCACTGCCCCA         -1
     1                    *
Met Asp Pro Leu Asn Leu Ser Trp Tyr Asp Asp Leu Glu Arg                10
ATG GAT CCA CTG AAC CTG TCC TGG TAC GAT GAC CTG GAG AGG
  1
                  *                                              30
Gln Asn Trp Ser Arg Pro Phe Asn Gly Ser Glu Gly Lys Ala Asp
CAG AAC TGG AGC CGG CCC TTC AAT GGG TCA GAA GGG AAG GCA GAC
            20                       40                          90
Arg Pro His Tyr Asn Tyr Tyr Ala Met Leu Leu Thr Leu Leu Ile
AGG CCC CAC TAC AAC TAC TAT GCC ATG CTG CTC ACC CTC CTC ATC     60
     50
Phe Ile Val Phe Gly Asn Val Leu Val Cys Met Ala Val Ser
TTT ATC ATC GTC TTT GGC AAT GTG CTG GTG TGC ATG GCT GTA TCC    180
```

```
Arg Glu Lys Ala Leu Gln Thr Thr Asn Tyr Leu Ile Val Ser
GCA GAG AAG GCT TTG CAG ACC ACC AAC TAC TTG ATA GTC AGC
                        70                              90

Leu Ala Val Ala Asp Leu Val Ala Thr Leu Val Met Pro Trp
CTT GCT GTG GCT GAT CTT GTG GCC ACA CTG GTA ATG CCG TGG
                80                                      270

Val Val Tyr Leu Glu Val Val Gly Glu Trp Lys Phe Ser Arg Ile
GTT GTC TAC CTG GAG GTG GTG GGT GAG TGG AAA TTC AGC AGG ATT
                        100                             120

His Cys Asp Ile Phe Val Thr Leu Asp Val Met Met Cys Thr Ala
CAC TGT GAC ATC TTT GTC ACT CTG GAT GTC ATG ATG TGC ACA GCA
                        110                             360

Ser Ile Leu Asn Leu Cys Ala Ile Ser Ile Asp Arg Tyr Thr Ala
AGC ATC CTG AAC CTG TGT GCC ATC AGC ATT GAC AGG TAC ACA GCT
                        130                             150

Val Ala Met Pro Met Leu Tyr Asn Thr Arg Tyr Ser Ser Lys Arg
GTG GCA ATG CCC ATG CTG TAT AAC ACA CGC TAC AGC TCC AAG CGC
                140                                     450
```

FIG. 1B

```
Arg Val Thr Val Met Ile Ala Ile Val Trp Val Leu Ser Phe Thr
CGA GTT ACT GTC ATG ATT GCC ATT GTC TGG GTC CTG TCC TTC ACC
                         170                 160              180

Ile Ser Cys Pro Leu Phe Gly Leu Asn Asn Thr Asp Gln Asn
ATC TCC TGC CCA CTC TTC GGA CTC AAC AAT ACA GAC CAG AAT
                                                    540

Glu Cys Ile Ile Ala Asn Pro Ala Phe Val Val Tyr Ser Ser Ile
GAG TGT ATC ATT GCC AAC CCT GCC TTT GTG TAC TCC TCC ATT
                         200                 190              210

Val Ser Phe Tyr Val Pro Phe Ile Val Thr Leu Leu Val Tyr Ile
GTC TCA TTC TAC GTG CCC TTC ATC GTC ACT CTG CTG GTC TAT ATC
                                                    630

Lys Ile Tyr Ile Val Leu Arg Arg Lys Arg Lys Arg Val Asn Thr
AAA ATC TAC ATC GTC CTC CGG AAG CGC AAG CGG GTC AAC ACC
                         230                 220              240

Lys Arg Ser Ser Arg Ala Phe Arg Ala Asn Leu Lys Thr Pro Leu
AAG CGC AGC AGT CGA GCT TTC AGA GCC AAC CTG AAG ACA CCA CTC
                                                    720
```

FIG. 1C

```
Lys Asp Ala Ala Arg Arg Ala Gln Glu Leu Glu Met Glu Met Leu
AAG GAT GCT GCC CGC CGA GCT CAG GAG CTG GAA ATG GAG ATG CTG
                                    250                     270

Ser Ser Thr Ser Pro Pro Glu Arg Thr Arg Tyr Ser Pro Ile Pro
TCA AGC ACC AGC CCC CCA GAG AGG ACC CGG TAT AGC CCC ATC CCT
            260                     280                     810

Pro Ser His His Gln Leu Thr Leu Pro Asp Pro Ser His His Gly
CCC AGT CAC CAC CAG CTC ACT CTC CCT GAT CCA TCC CAC CAC GGC
                            290                     300

Leu His Ser Asn Pro Asp Ser Pro Ala Lys Pro Gly Lys Asn Gly
CTA CAT AGC AAC CCT GAC AGT CCT GCC AAA CCA GAG AAG AAT GGG
                                                            900

His Ala Lys Ile Val Asn Pro Arg Ile Ala Lys Phe Phe Glu Ile
CAC GCC AAG ATT GTC AAT CCC AGG ATT GCC AAG TTC TTT GAG ATC
                            310                     320

Gln Thr Met Pro Asn Gly Lys Thr Arg Thr Ser Leu Lys Thr Met
CAG ACC ATG CCC AAT GGC AAA ACC CGG ACC TCC CTT AAG ACG ATG
                                320                     330
                                                            990
```

FIG. 1D

| | | | | | | | | | | |
|---|---|---|---|---|---|---|---|---|---|---|
| Ser | Arg | Arg | Lys | Leu | Ser | Gln | Gln | Lys | | |
| AGC | CGC | AGA | AAG | CTC | TCC | CAG | CAG | AAG | | |
| | | | | | | | | | | |
| Lys | Glu | Lys | Lys | Ala | Thr | Gln | | | | |
| AAG | GAG | AAA | GCC | ACT | CAG | | | | | |
| | | | | | 340 | | | | | 360 |
| Met | Leu | Ala | Ile | Val | Leu | Gly | Val | Phe | Ile | Ile |
| ATG | CTT | GCC | ATT | GTT | CTC | GGT | GTG | TTC | ATC | ATC |
| | | 350 | | | | | | | | |
| Cys | Trp | Leu | Pro | | | | | | | |
| TGC | TGG | CTG | CCC | | | | | | | |
| | | | 1080 | | | | | | | |
| Phe | Phe | Ile | Thr | His | Ile | Leu | Asn | Ile | His | Cys |
| TTC | TTC | ATC | ACG | CAC | ATC | CTG | AAT | ATA | CAC | TGT |
| | | | | | | | | 370 | | |
| Asp | Cys | Asn | Ile | | | | | | | |
| GAT | TGC | AAC | ATC | | | | | | | |
| | | | | | | | | | | |
| Pro | Pro | Val | Leu | Tyr | Ser | Ala | Phe | Thr | Trp | Leu |
| CCA | CCA | GTC | CTC | TAC | AGC | GCC | TTC | ACA | TGG | CTG |
| | | | | 380 | | | | | | |
| Gly | Tyr | Val | Asn | | | | | | | |
| GGC | TAT | GTC | AAC | | | | | | | |
| | | | 1170 | | | | | | | 390 |
| Ser | Ala | Val | Asn | Pro | Ile | Ile | Tyr | Thr | Thr | Phe |
| AGT | GCC | GTC | AAC | CCC | ATC | ATC | TAC | ACC | ACC | TTC |
| | | | | | | 400 | | | | |
| Asn | Ile | Glu | Phe | | | | | | | |
| AAC | ATC | GAG | TTC | | | | | | | |
| | | | | | | | | | | |
| Arg | Lys | Ala | Phe | Met | Lys | Ile | Leu | His | Cys | |
| CGC | AAG | GCC | TTC | ATG | AAG | ATC | TTG | CAC | TGC | |
| | | | | 410 | | | | 415 | | |
| TGAGTCTGCCCCTTGCCTG | | | | | | | | | | |
| 1264 | | | | | | | | | | |

FIG. 1E

```
CACAGCAGCTGCTTCCCACCTCCTGCCTGCCTATGCAGGCCAGACCTCATCCCTGCAAGCTG
TGGGCAGAAGGCCCAGATGAACTTGGCCCTTCTCGACCCTGCAGGCCCTGCAGTGTTA   1383
GCTTGGCTCGATGCCCCTCTCTGCCCACACACCCCTCATCCTGCCAGGGTAGGGCCAGGG
AGACTGGTATCTTACCAGCTCTGGGTTGGACCCATGGCTCAGGGCTCAGCTCACAGAGTGC  1502
CCCTCTCATATCCAGACCCTGTCTCCTTGGCACCAAAGATGCAGCGGCCCTTCCTTGACC
TTCCTCTTGGGCACAGAAACTAGCTCAGTGGTCGAGCACACCCTGATCGCTGGCTTGGCC   1621
TGGCCCTTGCTGTGCCTGTGCCGGGATCAGGTGGTGGGAGGAGCGACACGTTCTTACTTT
ATAGGAACCACATAGGAAAGCAGGGAACGCCAAGTCCTCCAGGCACATCAGTGTCAGG    1740
AGACACACATAAACACCAGGTAGCTCCATGACCCCAGAGAAACTGAGGCTGAAAAATC
TGTTTCCACTCCAACTCTAGTGTGAGTCCCTACTTTTCATAGCCATGGGTATTACTATG   1859
```

FIG. 1F

```
TCCTACCCTTGTTATAGTATCCCATGGGGTTTCTGTACCATTTGGGGAAAACAACTCTA
ATCCTCAAGGGCCCCAAGAGAATCTGTAAGGAGAAAATAGGCTGATCTCCCCTACTCT  1978
CCAATCCACTCCACCACTTCTTGATATACCTTGGATGTATCCATTCCTCACAGCAAATG
CTGGCCAGTCAGGCCCTTGGACCAGTGTTGGAGTTGAAGCTGGATGTGGTAACTTGGGCT  2097
CTTTGGGGCTGGGGGGTTGTTAACATCGTCTCTTCCATATCTCTTCCTTCCCAGTG
CCCTCTGCCCTTAGAAGAGGCTGTGGATGGGGCTGCTGGGACTGCTGATACCATTGGGCCTGG  2216
CCCTGAATGAGGAGGGGAAGCTGCAGTTTGGAGGGTTCTGGGATCCAACTCTGTAACAT
CACTATACCTGTACCAAAACTAATAAACCCTTGACAAGAGTCAAAAAAAAAA
                                                    2317
```

```
         I
D6   MD....PL...NISWYDDDLERQNWSRPFNGSEGKADRPHYNYYAMILL.IFIIVFGNVLVCMAVSREKALQTITNY
β6   MGP...P...QNDSDFLLTTNGSHV...PDHDVTEERDEAWVVGMAIIMSVIVLAIVFGNVLVITAIAKFERLQTIVNY
α6   MGSLQ.PQA.GNASWNGTEAPG..GGARATPYSLQVT....LTLVCLAGII.MLLTVFGNVLVIIAVFTSRAIKAPQNL
G-21 MDVLS.PGQ.QNNTTSPPAPFE..TGGNTTGISDVTVSYQV.ITSLIFGTL.IFCAVIGNACVVAAIALERSLQNVANY
M1   MNTSAPPAVSPNITVLAP.....GKGPWQA.....FIGITIGLL.SLATVIGNILVIISFKVNTELIKTIVNNY
SK   MGACV.VMTDINIS.......SGLDSNATGITAFSMPGWQLALWTAAYLAL.VLVAVMGNATMWIILAHQRMRIVINY

II
D6   LIVSLAMADLIVATLVMPWVVYLEVTGEWKFSRIHCDIFVTLDVMCTASILNLCAISIDRYTAVAMPMLYNTRYSSKRR
β6   FLDSLACADLIVGIAVMPFGASHIIMKMWTFGNFWCEFWTSIDVLCVTASIETLCVIAVDRYIAITSPFKYQSLLTKNKA
α6   FLSLASADLVATLVIPFSLANEVMGYWPFGTFCNIWIAVDVLCCTASIIETLCAISIDRYWSITQAIEYNLKRTPRRI
G-21 LIGSLAVTDIMVSVLVIPMAALYQVLNNWTLGQVTCDLFIALDVLCCTSSILHLCAIAIQRYWAITDPIDYVNKRTPRR
M1   FLLSLACADLIIGTFSMNLYTTYLLMGHWALGTLACDLWLALDYVASNASVMNLLIISFDRYFSVTRPLSYRAKTRPRRA
SK   FLVNLALADICMAAFNAAFNFVYASHNIWFEGRAFCYFQNLFPITAMFVSIYSMTALAAQRYMAIVRFQPRLSAPGTR

III                                                      V
D6   VTMVMTIAIVWVLSFTISC.PLLFGLNNTD.......QNECIIANPAFVVYSSIMSFYVPFIVTLLVYIKIYIVLRKRR
β6   RMILMVWIVSGLTSFIPIQMHWYRATH..QKAIDCYHRETCCDFFTNQAYAIWSSIVSFYVPLLIMILVFYVSRVFQVA
α6   KAIIITVWVISAVISFPPLISIEKKGGG....GGPQPAEPRCEINDQKWYVISSCIGSFFAPCLIMILVHVRIYQIAKR
G-21 ALT.SLT.WLIGFLLSIPPMLGWRTPEDR....SDPDACTISKDMGYTIYSTFGAFYIPLILMLVLYGRIFRAARFRIR
M1   ALM.IGLAWLVSFVLWA.PAILFWQYLVGE....RTVLAGQCYIQFLSQPIITFGTAMAAFYLPVTVMCTIYWRIYRETENRAREL
SK   .AVL.IAGIWVALALAF.PQCFYSTITTDEGATKCVVAWPEDSGGKMLLLYHLIVMFVAYSVIGLTLWRSVPG

IV                              VI
D6   -KEKKATQMIAIVIGFIICWLPFFIITHIINIHCQCN.....IPPVLYSAFTWLGYVNSA..VNPLIYTTFNIEFRNAFMKILHC
β6   -KEKKAIKTLGIIMGIFTLCWLPFFIVNIVHVIQDNL....IPKEVYILLNWLGYVNSA...PNPLIYCRSP.DFRIAFQELLCL
α6   -REKRFTFVLAVVIGVFVVCWFPFFFETYTLIAVGCS...VPRTLFKFFPWIGYCNSS...LNPVIYTIFNHDFRRAFMKILRCRC
G-21 -REKKTVKTLGIIMGTFILCWIPFFIVALVLPPCESSC...HMPTILGAIINWLGYSNSL..INPVIYAYFNKDFQNAFMKIIKCNFCRQ
M1   -KEKKAARTLSAILLAFIVTWTPYNIMVLVSTFCKDC....VPETLWELGYWLCYVNST...INPMCYALQNKAFRDTFRLLLLHCR
SK   -AKKFVKTMVIMVIFAICWLPYHLYFILGTFQEDIYCHKFIQQVLPYIA..MSSTMYNPIIYCCINHRFRSQELAPRCC
```

(111)
(32)
(137)
(110)
(137)
(12)

(36)
(6)
(24)
(62)

| DRUG | Ki (nM) | |
|---|---|---|
| | RGB-2 Transformed Ltk-Cells | Rat Striatum |
| (+)-Butaclamol | 0.83 | 1.0 |
| (−)-Butaclamol | >1,000 | >1,000 |
| Haloperidol | 3.0 | 5.3 |
| Dopamine + GTP | 17,000 | 6,300 |
| Sulpiride | | |
|   high affinity | 80 | 67 (87%) |
|   low affinity | --- | >10,000 (13%) |
| SCH 23390 | | |
|   high affinity | --- | 35 (16%) |
|   low affinity | 1,000 | 780 (84%) |
| Ketanserin | | |
|   high affinity | --- | 27 (25%) |
|   low affinity | >1,000 | >1,000 (75%) |

FIG. 4C

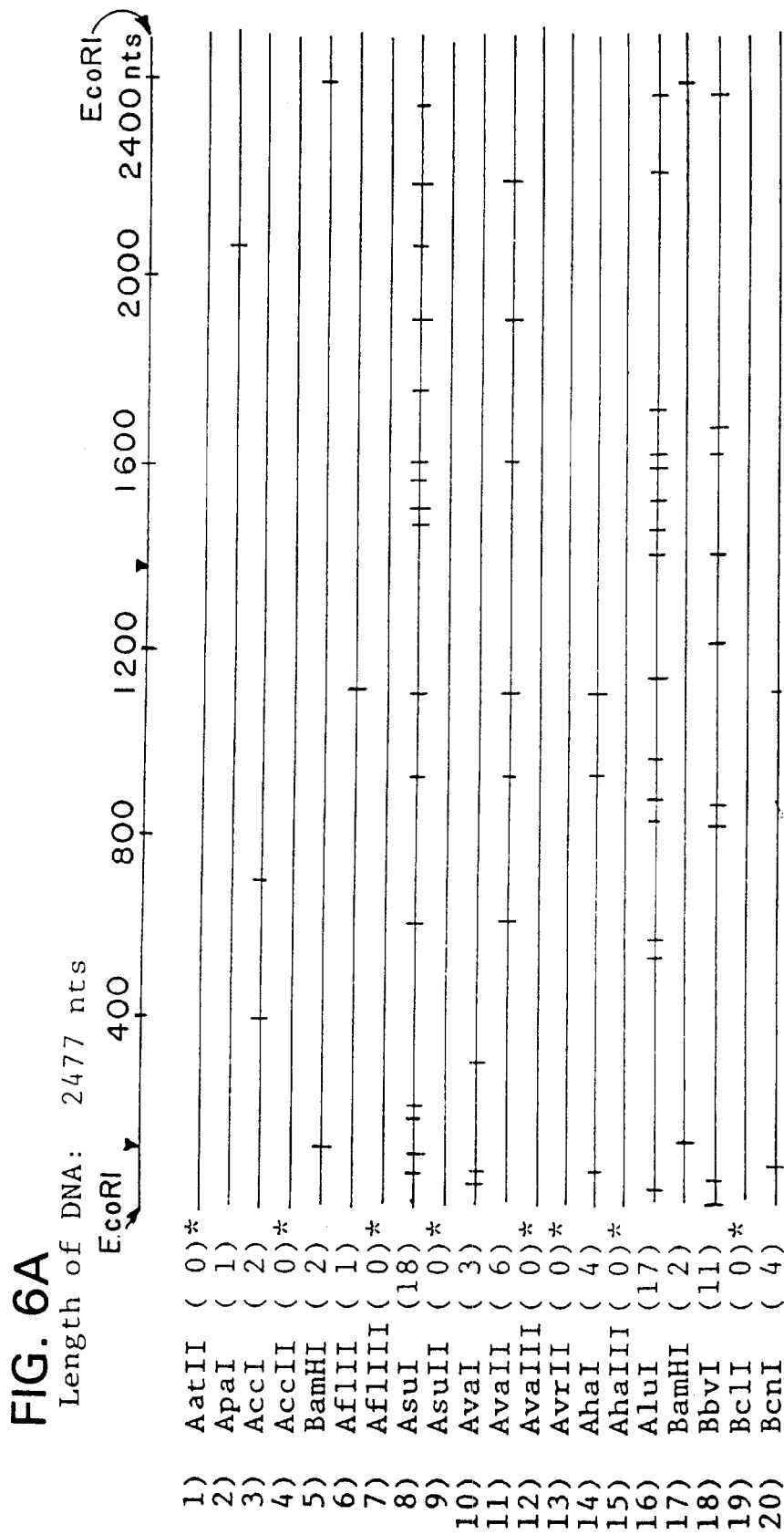

FIG. 7A

```
                    27                                                                                    54
3' GTC GGG TGG GCT CTC CTG GGC CAT GTC GGT GGG TGG GTC GGT GGT GGT CGA 5'
5' CAG CCC ACC CGA GAG GAC CCG GTA CAG CCC CAT CCC ACC CAG CCA CCA GCT 3'
   Gln Pro Thr Arg Glu Asp Pro Val Gln Pro His Pro Thr Gln Pro Pro Ala
   Ser Pro Pro Glu Arg Thr Arg Tyr Ser Pro Ile Pro Pro Ser His His Gln Leu
   Ala His Pro Arg Gly Pro Gly Thr Ala Pro Ser His Pro Ala Thr Thr Ser 81                                                                                   108
   CTG AGA GGG GCT GGG CAG GGT GGT ACC AGA GGT GTC GTG CAC GTC GGG GCG
   GAC TCT CCC CGA CCC GTC CCA GGT TCT CCA CAG CAC TCC CGA CAG CCC CGC
   Asp Ser Pro Arg Pro Val Pro Pro Trp Ser Pro Gln His Ser Arg Gln Pro Arg
   Thr Leu Pro Asp Pro Ser His His Gly Leu His Ser Thr Pro Asp Ser Pro Ala
   Leu Ser Pro Thr Arg Pro Thr MET Val Ser Thr Ala Leu Pro Thr Ala Pro Pro 135                                                                                   162
   GTT TGG TCT CTT CTT ACC CGT ACG GTT TTC CTG GTG GGG TTC CTA ACG GTT CTA
   CAA ACC AGA GAA GAA TGG GCA TGC CAA AAG GAC CAC CCC AAG GAT TGC CAA GAT
   Gln Thr Arg Glu Glu Trp Ala Cys Gln Lys Asp His Pro Lys Asp Cys Gln Asp
   Lys Pro Glu Lys Asn Gly His Ala Lys Arg Thr Thr Pro Arg Ile Ala Lys Ile
   Asn Gln Arg Arg MET Gly MET Pro Lys Gly Pro Pro Gln Gly Leu Pro Arg Ser 189                                                                                   216
   GAA ACT CTA GGT CTG GTA CGG GTT ACC GTT TTG GGC CTG GAG GGA GTT CTG GTA
   CTT TGA GAT CCA GAC CAT GCC CAA TGG CAA AAC CCG GAC CTC CCT CAA GAC CAT
   Leu  .  Asp Pro Asp His Ala Gln Trp Gln Asn Pro Asp Leu Pro Gln Asp His
       Phe Glu Ile Gln Thr MET Pro Asn Gly Lys Thr Arg Thr Ser Leu Lys Thr MET
```

FIG. 7B

```
                                                                              243                                                       270
CTC GGC ATC CTT C6A G55 GGT CGT CCT CTT CTT TCG GTG AGT CTA CGA GCG
GAG CCG TAG GAA G3T C44 CCA GCA GAA GAA AGC CAC TCA GAT GCT CGC
Glu Pro  .  Glu C      TT Pro Ala Glu Gly Glu Ser His Ser Asp Ala Arg
Ser Arg Arg Lys Leu Phe Gln Gln Lys Glu Lys Ala Thr Gln MET Leu Ala
Ala Val Gly          Ser       Ser Arg Arg Arg Arg Lys Pro Leu Arg Cys Ser Pro 297                                                   324
GTA 5CA AGA GCC GCA CAA GTA GAC CGA CGG GAA GAA GTA GTC TGT GTA
CAT 4GT TCT CGG CGT GTT CAT CTG GCT CTT CTT CAT CAC ACA CAT
His T   Ser Arg Arg Val His His Leu Ala Ala Leu Leu His His Thr His
ILE Val Leu Gly Val Phe Ile Cys Trp Leu Pro Phe Phe Ile Thr His Ile
le  Phe Ser Ala Cys Ser Ser Ser Ala Gly Cys Pro Ser Ser His Thr Ser 351                                                   378
GGA CTT GTA TGT GAC ACT GAC GTT GTA GGG CGG ACA GAT GTC GCG GAA GTG
CCT GAA CAT ACA CTG TGA CTG CAA CAT CCC GCC TGT CTA CAG CGC CTT CAC
Pro Glu His Thr Leu  .  Leu Gln His Pro Ala Cys Pro Val Gln Arg Leu His
Leu Asn Ile His Cys Asp Cys Asn Ile Pro Pro Val Leu Tyr Ser Ala Phe Thr
 .  Thr Tyr Thr Val Thr Ala Thr Ser Arg Leu Ser Cys Thr Ala Pro Ser Arg 405                                                   432
CAC CGA CCC GAT ACA GTT GTC GCG GCA CTT GGG GTA GAT GTG GTG GAA GTT
GTG GCT GGG CTA TGT CAA CAG CGC CGT GAA CCC CAT CTA CAC CAC CTT CAA
Val Ala Gly Leu Cys Gln Arg Arg Glu Pro His His Leu His His Leu Gln
Trp Leu Gly Tyr Val Asn Ser Ala Val Asn Pro Ile Tyr Thr Thr Thr Phe Asn
 .  Gly Trp Ala MET Ser Thr Ala Pro  .  Thr Pro Ser Ser Thr Pro Pro Ser Thr
```

```
                                                      459                                                  486
GTA ACT CAA GGC GTT CCG GAA GGA CTT CTA GGA GGT GAC GAC TGA GAC GAC CTG GGA
CAT TGA GTT CCG CAA GGC CTT GAA GAT CCT CCA CTG CCT ACT CTG CTG CCT
His . Val Pro Gln Gly Leu Pro Glu Asp Pro Pro Leu Thr Leu Leu Pro
    Ile Glu Phe Arg Lys Ala Phe Leu Lys Ile Leu His Cys STOPLeu Cys Cys Leu
        Leu Ser Ser Ala Arg Pro Ser .    Arg Ser Ser Thr Ala Asp Ser Ala Ala Cys
                                                      513                                                  540
CGG CGT GTC GTC GGA CGA AGG GTG GAG GGA CGG GTC ACG GCC CGG AGT GGG
GCC GCA CAG CAG CCT GCT TCC CAC CTC CCT GCC CAG TGC CGG CCA GCC TCA CCC
Ala Ala Gln Gln Pro Ala Ser His Leu Pro Ala Gln Cys Arg Pro Ala Ser Pro
    Pro His Ser Ser Leu Leu Pro Thr Ser Leu Pro Ser Ala Gly Gln Pro His Pro
        Arg Thr Ala Ala Cys Phe Pro Pro Pro Cys Pro Val Pro Ala Ser Leu Thr Leu
                                                      567                                                  594
AAC GCT TGG CAC TCG TCC TTC CGG ACC CAC CTA GCC GGA GGA GAA GAT CGG GGC
TTG CGA ACC GTG AGC AAG GCC TGG GTG GAT CGG CCT CTT CTA GCC CCG
Leu Arg Thr Val Ser Arg Lys Ala Trp Val Asp Arg Pro Leu Leu Ala Pro
    Cys Glu Pro . Ala Gly Arg Pro Gly Trp Ile Gly Leu Leu Phe . Pro Arg
        Ala Asn Arg Glu Gln Glu Gln Gly Leu Gly Ser Ala Ser Ser Ser Pro Gly

| | CONTROL | | | +P.T. | | |
|---|---|---|---|---|---|---|
| | BASAL | FSK | FSK+DA | BASAL | FSK | FSK+DA |
| $\bar{X}$ | 2.1 | 22.6 | 14.3 | 1.7 | 26.7 | 23.1 |
| S.E. | 0.2 | 2.2 | 2.1 | 0.4 | 2.0 | 0.5 |
| INH | — | — | 41% | — | — | 14% |

FIG. 12B

| | CONTROL | | | +P.T. | | |
|---|---|---|---|---|---|---|
| | BASAL | VIP | DA | VIP+DA | BASAL | VIP | DA | VIP+DA |
| $\bar{X}$ | 0.60 | 2.41 | 0.32 | 0.84 | 0.61 | 2.68 | 0.55 | 2.56 |
| S.E. | 0.02 | 0.31 | 0.02 | 0.13 | 0.09 | 0.08 | 0.03 | 0.25 |
| INH | — | — | 53% | 71% | — | — | 10% | 3% |

FIG. 12C

| | CONTROL | | | +P.T. | | |
|---|---|---|---|---|---|---|
| | BASAL | VIP | DA | VIP+DA | BASAL | VIP | DA | VIP+DA |
| $\bar{X}$ | 0.78 | 5.1 | 0.25 | 0.76 | 0.64 | 5.29 | 0.66 | 4.76 |
| S.E. | 0.04 | 0.4 | 0.03 | 0.01 | 0.01 | 0.44 | 0.03 | 0.16 |
| INH | — | — | 68% | 88% | — | — | 0% | 12% |

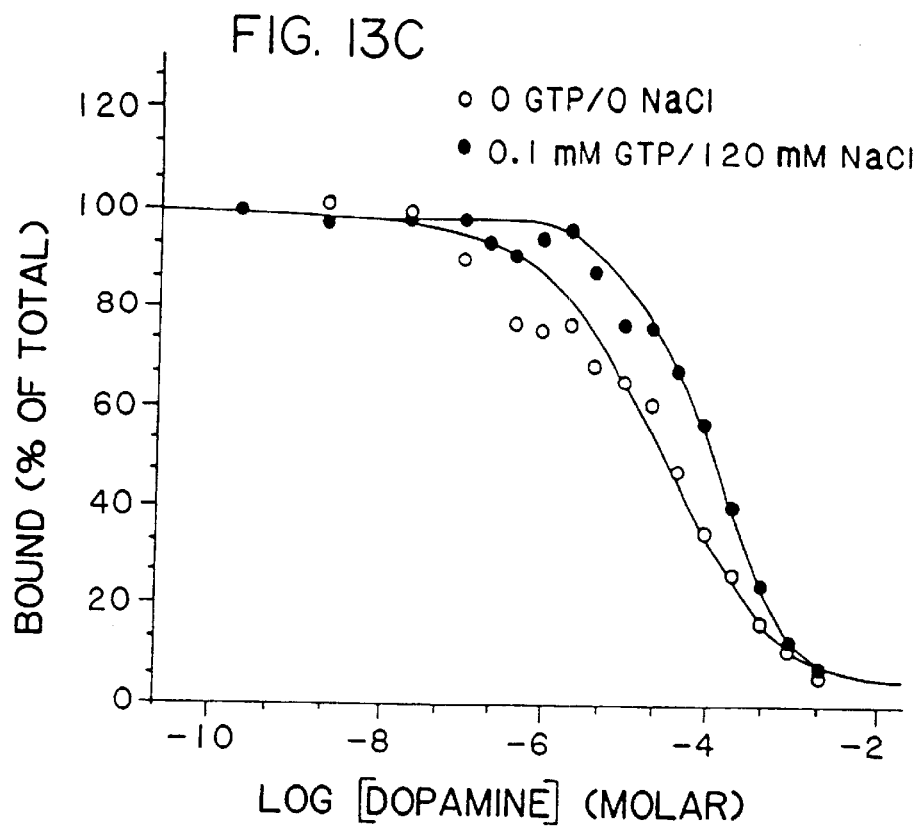
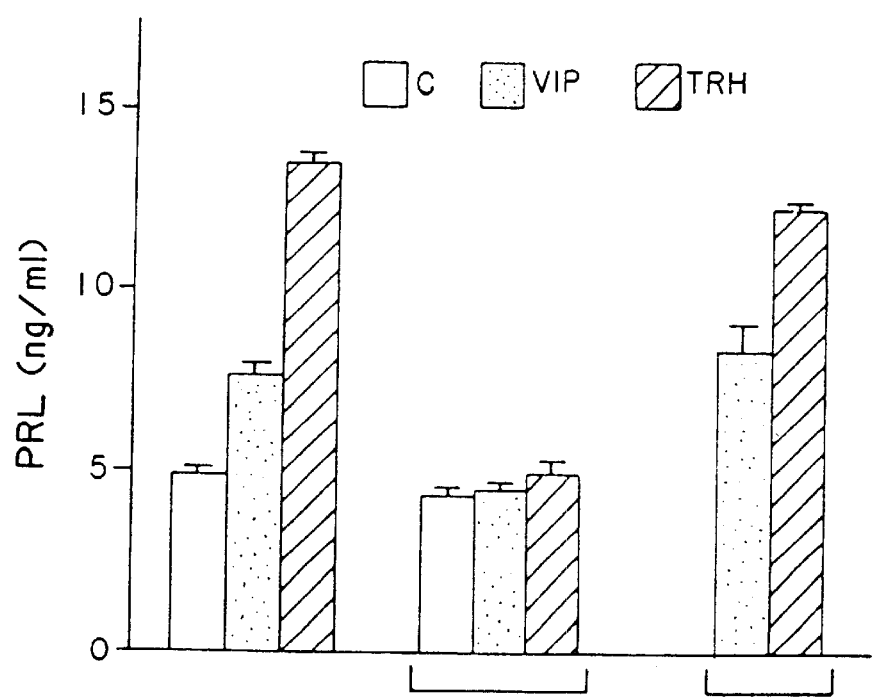

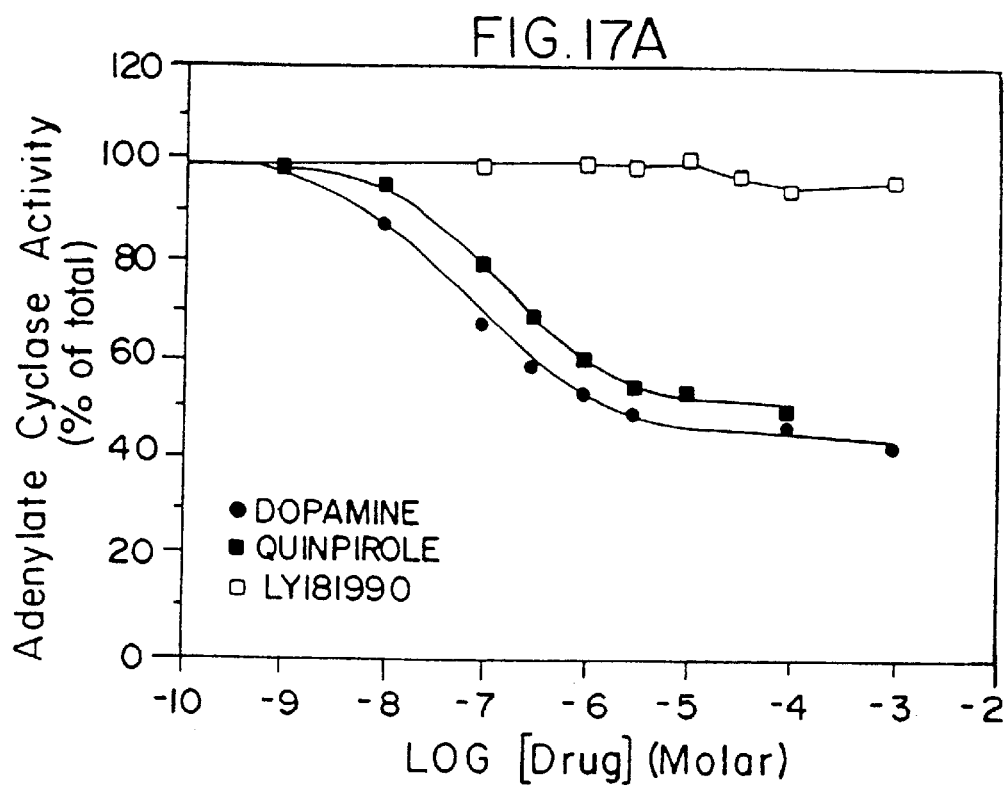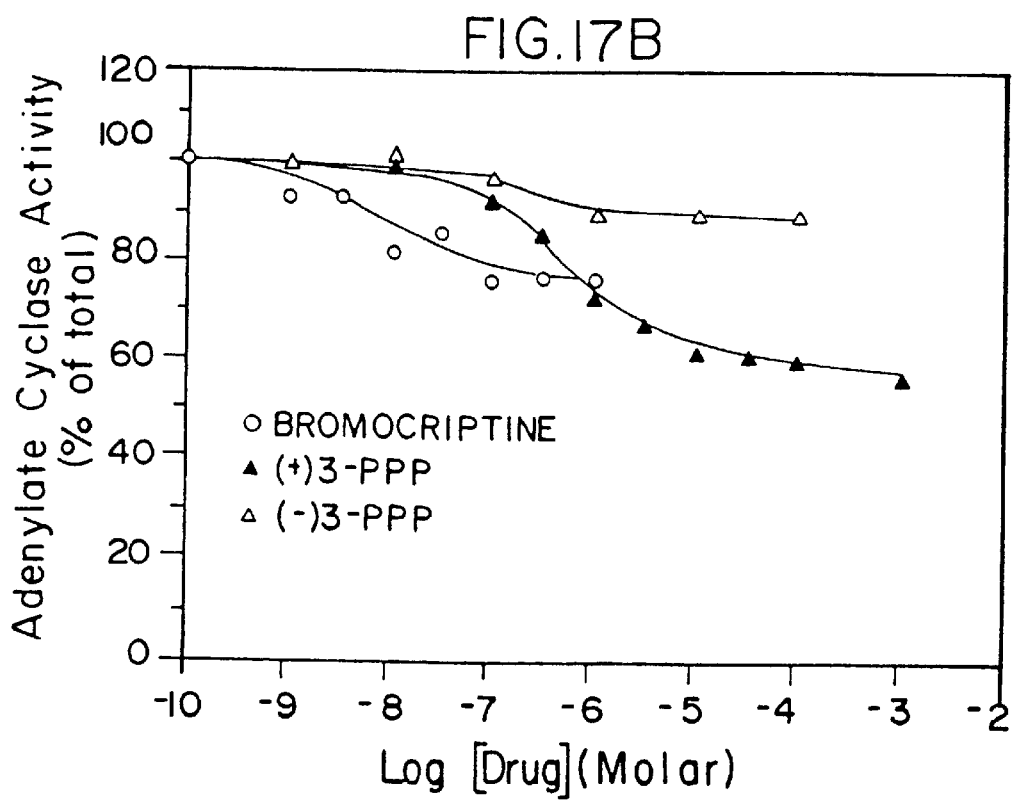

```
-33  AGAGCCTGGCCACCCAGTGGCTCCACCGCCCTG
                            *                                    *
     METAspProLeuAsnLeuSerTrpTyrAspAspLeuGluArgGlnAsnTrpSerArg
                    10                                  20
     ATGGATCCACTGAATCTGTCCTGGTATGATGATCTGGAGAGGCAGAACTGGAGCCGG
     |||||||||||||| |||||||||||| |||| |||| ||||||||||||||||||
     ATGGATCCACTGAACCTGTCCTGGTACGATGATCTGGAGAGGCAGAACTGGGAGCCGG
     METAspProLeuAsnLeuSerTrpTyrAspAspLeuGluArgGlnAsnTrpGluPro
                                                          Glu
                    *
     ProPheAsnGlySerAspGlyLysAlaAspArgProHisTyrAsnTyrTyr AlaThrLeu
                            30                                  40
     CCCTTCAACGGGTCAGACGGGAAGGCGGACAGACCCCACTACAACTACTATGCCACACTG
     ||||||| || ||||||||| |||||||||||||| ||||||||||||||| ||||||
     CCCTTCAATGGGTCAGAAGGCAGAGGCCAGACCCCACTACAACTACTATGCCATGCTG
                                                            MET
                                                              120
```

```
          1                                                   50                                60
          LeuThrLeuLeuIleAlaValIleValPheGlyAsnValLeuValCysMETAlaValSer
          CTCACCCTGCTCATCGCTGTCATCGTCTTCGGCAACGTCCTGGTGTGCATGGCTGTGTCC
          ||||||| ||||| |||||  ||||| |||||||||| || |||||||||||||||||
          CTCACCCTCCTCATCTTATCATCTTTGGCAATGTGCTGGTGTGCATGGCTGTATCC
                         PheIle 70                    11              80
          ArgGluLysAlaLeuGlnThrThrThrAsnTyr LeuIleValSerLeuAlaValAlaAlaAsp
          CGCGAGAAGGCGCTGCAGACCACCACCAACTACCTGATCGTCAGCCTCGCAGTGGCCGAC
          ||  ||||||  |||||||| ||||||||||||||| |||| ||||| ||||||  ||
          CGAGAGAAGGCTTTGCAGACCACCACCAACTACTTGATAGTCAGCCTTGCTGTGGCTGAT 240
                                          90                       100
          LeuLeuValAlaThrLeuValMETProTrpValValTyrLeuGluValValGlyGluTrp
          CTCCTCGTCGCCACACTGGTCATGCCCTGGGTTGTCTACCTGGAGGTGGTAGGTGAGTGG
          || || || ||||||||||| || ||||| ||||||||||||||| |||| |||||||
          CTTCTGGTGGCCACACTGGTAATGCCGTGGGTTGTCTACCTGGAGGTGGTGGGTGAGTGG
```

FIG. 18C

```
          IV
          ValLeuSerPheThrIleSerCysProLeuLeuPheGlyLeu|AsnAsnAlaAspGlnAsn
          GTCCTGTCCTTCACCATCTCCTGCCCACTCCTCCTTTCGGACTCAATAACGCAGACCAGAAC
          |||||||||||||||||||||||||||||||||||||||||||||| ||  |||||||||||
          GTCCTGTCCTTCACCATCTCCTGCCCACTCTCCTCTTCGGACTCAACAATACAGACCAGAAT
                                                               Thr
                      190                 200
          GluCysIleIleAlaAsn|ProAlaPheValValTyrSerSerIleValSerPheTyrVal
          GAGTGCATCATTGCCAACCCGGCCTTCGTGGTCTACTCCTCCATCGTCTCCTTCTACGTG
          |||| |||||||||||||||||| |||  ||||||||||| |||| ||||| |||||||
          GAGTGTATCATTGCCAACCCCTGCCTTGTGGTCTACTCCTTTGTCTCCATTGTCTCACGTG
                      210                  220
          ProPheIleValThrLeuLeuValTyrIle|LysIleTyrIleValLeuArgArgArgArg
          CCCTTCATTGTCACCCTGCTGGTCTACATCAAGATCTACATTGTCCTCCGCAGACGCCGC
          |||||||  ||||||||||||||||||||| |||||||| ||| ||||  |||| |||
          CCCTTCATCGTCACTCTGCTGGTCTACTCTGCTATATCAAAATCTACATCGTCCTCCGGAAGCGCCGG
                                                              Lys
```

FIG. 18D

```
                                                  240
LysArgValAsnThrLysArgSerSerArgArgAlaPheArgAlaHisLeuArgAlaProLeu
AAGCGAGTCAACACCAAGCGCAGCAGCCGAGCCGAGCTTTCAGGGCCCACCTGAGGGCTCCACTA       720
|||| ||||||||| ||||||| |||||||| ||||||| ||| ||||||| | | |||||
AAGCGGGTCAACACCCTCAAGGCAGCCGAGCTCGAGCTTTCAGAGCCAACCTGAAGACACCACTC
                                       Asn     LysThr
        *                                                     *
LysGlyAsnCysThrHisProGluAspMETLysLeuCysThrValIleMETLysSerAsn
AAGGGCAACTGTACTCACCCCGAGGACATGAAACTCTGCACCGTTATCATGAAGTCTAAT
||| !                                                              
AAG...

280
GlySerPheProValAsnArgArgArgValGluAlaAlaArgArgAlaGlnGluLeuGlu
GGGAGTTTCCCAGTGAACAGGCGGAGAGTGGAGGCTGCCCGGCGAGCCCAGGAGCTGGAG       840
        ||  |||||||| ||||  ||||| ||||| | |||||| ||||||||||
       GATGCTGCCCCGAGCTCAGGAGCTGGAA
        Asp
```

FIG. 18E

```
                                              290                                    300
        METGluMETLeuSerSerThrSerProProGluArgThrArgTyrSerProIleProPro
        ATGGAGATGCTCTCCAGCACCAGCCCGGAGAGGACCCGAGAGCCCCATCCCCACCC
        ||||||||| || |||||||||||| || ||||||||| || |||||||||||||
        ATGGAGATGCTGTCAAGCACCAGCCCCCAGAGAGACCCGGTATAGCCCCATCCCTCCC 310                                    320
        SerHisHisGlnLeuThrLeuProAspProSerHisHisGlyLeuHisSerThrProAsp
        AGCCACCACCAGCTCTCCCCCGACCCGTCCCACCATGGTCTCCACAGCACTCCCCGAC
        || ||||||||||||| ||| || ||| || ||||  || ||  |||||| ||| ||
        AGTCACCACCAGCTCACTCTCCCTGATCCCATCCCATAGCCCTACATAGCAACCCTGAC
                                                                Asn 330                                    339
        SerProAlaLysProGluLysAsnGlyHisAlaLys    AspHisProLysIleAlaLys
        AGCCCCGCCAAACCAGAAGAAGAATGGGCATGCCAAA...GACCACCCAAGATTGCCAAG
        ||  || ||||| ||||||||||||||| ||||||||   | |  |||||||| |||||
        AGTCCTGCCAAACCAGAGAAGAAGAATGGGCACGCCAAGATTGTCAATCCCAGGATTGCCAAG
                                                  IleValAsn    Arg
```

```
                                          VII  419
            409          ┌─────────────────────────────────────────┐
AspCysAsnIleProPro│ValLeuTyrSerAlaPheThrTrpLeuGlyTyrValAsnSer│

GACTGCAACATCCCGGCCCTGTCCTGTACAGGCGCCTTCACGTGGCTGGGCTATGTCAACAGC
 ||||||||||||||||  ||||  ||||| |||||||||||  ||||||||||||||||||
GATTGCAACATCCCACCAGTCCTCTACAGCCGCCTTCACATGGCTGGGCTATGTCAACAGT 429                               439
         ┌─────────────────────────────────────────┐
         │AlaValAsnProIleIleTyrThrThrPhe│AsnIleGluPheArgLysAlaPheLeuLys
                                                                    1317
GCCGTGAACCCCATCATCTACACCACCTTCAACATTGAGTTCCGCAAGGCCTTCCTGAAG
|||||||||| |||||||||||| |||||||||||| |||||||||||||||||| ||||
GCCGTCAACCCCATCATCTACACCTTCAACATCGAGTTCCGCAAGGCCTTCATGAAG
                                                       MET
IleLeuHisCys *
ATCCTCCACTGCTGACTCTGCTGCCCGCCTGCCCTGCCCACAGCAGCCTGCTTCCCACCTCCCTGCC
||| |  |||||||||| |||||||
ATCTTGCACTGCTGA

FIG. 18H
```

CAGGCCGGGCCAGCCTCACCCTTGCGAACCGTGAGCAGGAAGGCCTGGGTGGATCGGCCTC 1437

CTCTTCTTAGCCCCGGCCAGGCCCTGCAGTGTTCGCTTGGCTCCATGCTCCTCACTGCCCG

CACACCCTCACTCTGCCAGGGCAGTGCTAGTGAGCTGGGCATGGTACCAGCCCTGGGGCT 1557

GGCCCCAGCTCAGGGGCAGCTCATAGAGTCCCCCCACCTCCAGTCCCCCTATCCTT

GGCACCAAAGATGCAGCCCGCCTTCCCTTGACCTTCCTCTGGGCTCTAGGGTTGCTGGAGC 1677

CTGAGTCAGGGCCCAGAGGCTGAGTTTCTCTTTGTGGGCTTGGCGTTGGAGCAGGCGGT

GGGGAGAGATGGACAGTTCACACCCTGCCAAGGCCCACAGGAGGCAAGCTCTCTTGC 1797

CGAGGAGCCAGGCAACTTCAGTCCTGGGAGACCCATGTAAATACCAGACTGCAGGTTGGA

CCCCAAGGATTCCCAAGCCAAAAACCTTAGCTCCCCTCCCCGATGTGGACCTCTA 1917

FIG. 18I

```
CTTTCCAGGCTAGTCCCGGACCCTCACCCTTCACAGCTCCCCAAGTGGTTTCCACAT
GCTCTGAGAAGAGGAGCCCTCATCTTGAAGGCCCAGGAGGTCTATGGGAGAGGAACT  2037
CCTTGGCCTAGCCCACCCCTGCTGCCTTCTGACGGCCCCTGCAATGTATCCCTTCTCACAGC
ACATGCTGGCCAGCCTGGGGCCTGGCAGGGAGGTCAGGCCCTGGAACTCTATCTGGGCCT  2157
GGGCTAGGGACATCAGAGGTTCTTTGAGGACTGCCTCTGCCACACTCTGACGCAAAAACC
ACTTTCCTTTCTATTCCTTCTGGCCCTTTCCTCTCCCTGTTTCCCTTCCACTGC  2277
CTCTGCCTTAGAGGAGCCTAAGAGGCTGCTGAAAACCATCTGGCCTGGCCTGGC
CCTGCCCTGAGGAGGGCAAGCTTGGGAGAGCCCCTGGGCCTAGAGACTCTG  2397
TAACATCACTATCCGATGCACCAAACTAATAAAACTTTGACGAGTCACCTTC (A)$_n$  2449
```

| DRUG | HUMAN D$_2$ | RAT D$_2$ | RAT STRIATUM |
|---|---|---|---|
| SPIPERONE | 0.125 | 0.35 | 0.56 |
| (+) BUTACLAMOL | 0.94 | 1.2 | 1.6 |
| HALOPERIDOL | 2.4 | 5.1 | 5.8 |
| SULPIRIDE | 206 | 160 | 205 |
| MIANSERIN (5-HT) | 2685 | 4300 | 4600 |
| SCH 23390 (D1) | 2145 | 2500 | 3300 |
| (+) BUTACLAMOL | >10,000 | >10,000 | >10,000 |
| Kd [3H] DOMPERIDONE | 0.74 | 0.40 | 0.40 |

| | |
|---|---|
| 285¹ | 286 |
| exon1...GGAGgtaggtg...intron1...tccccagGTGG...exon2 | |
| 395 | 396 |
| exon2...ACAGgtgagcc...intron2...cttgcagGTAC...exon3 | |
| 532 | 533 |
| exon3...GCAGgtacatt...intron3...cccccagACCA...exon4 | |
| 723 | 724 |
| exon4...AAAGgtctcaa...intron4...tccacagGGCA...exon5 | |
| 810 | 811 |
| exon5...AGTGgtaagtg...intron5...ggtgcagGAGG...exon6 | |
| 1138 | 1139 |
| exon6...CTCGgtgagtc...intron6...cccccagGCGT...exon7 | |

¹Numbering begins with A of the putative initiator methionine codon (see Fig. 18)

DOPAMINE RECEPTORS AND GENES

This application is a continuation of application Ser. No. 07/973,588 filed Nov. 9, 1992, abandoned, which is a continuation of U.S. Ser. No. 07/438,544, filed Nov. 20, 1989, now abandoned, which was a continuation-in-part of U.S. Ser. No. 07/273,373, filed Nov. 18, 1988, now abandoned.

ACKNOWLEDGEMENT OF GOVERNMENT SUPPORT

This invention was made with government support under DK 37231 and MH 45614 awarded by the National Institutes of Health. The government has certain rights in the invention.

BACKGROUND OF THE INVENTION

This invention relates to dopamine receptors from mammalian species and the corresponding genes. In particular, it relates to the isolation, sequencing and/or cloning of $D_2$ dopamine receptor genes, the synthesis of $D_2$ dopamine receptors by transformed cells, and the manufacture and use of a variety of novel products enabled by the identification and cloning of DNA encoding dopamine receptors.

Dopamine receptors in general have been implicated in a large number of neurological and other disorders, including, for example, movement disorders, schizophrenia, drug addiction, Parkinson's disease, Tourette syndrome, Tardive Dyskinesia, and many others. As a result, the dopamine receptor has been the subject of numerous pharmacological and biochemical studies.

In general, dopamine receptors can be classified into $D_1$ and $D_2$ subtypes based on pharmacological and biochemical characteristics (1,2). The $D_2$ dopamine receptor has been implicated in the pathophysiology and treatment of the mentioned disorders. In addition, it is known that the $D_2$ dopamine receptor interacts with guanine nucleotide binding proteins to modulate second messenger systems (6,7).

Despite the heavy emphasis placed on elucidation of the existence and properties of the dopamine receptor and its gene, identification, isolation and cloning have been inaccessible heretofore. This is true despite the knowledge that other members of the family of receptors that are coupled to G proteins share a significant similarity in primary amino acid sequence and exhibit an archetypical topology predicted to consist of seven putative transmembrane domains (8). Regarding the serotonin receptor, e.g., see Julius et al., Science, Vol. 241, 558 (1988).

SUMMARY OF THE INVENTION

This invention has successfully identified, isolated and cloned mammalian, including human, $D_2$ dopamine receptor gene sequences and produced the encoded dopamine receptor. The corresponding polypeptide has been synthesized. Sequences of both the gene and the polypeptide have been determined. The invention also provides a variety of new and useful nucleic acid, cell line, vector, and polypeptide and medicinal products, inter alia, as well as methods of using these.

Thus, this invention relates to an isolated DNA sequence, an identified portion of which is a structural gene which encodes a polypeptide having the biological activity of a mammalian $D_2$ dopamine receptor. In particular, it relates to an isolated DNA sequence which will hybridize to a DNA sequence encoding a mammalian $D_2$ dopamine receptor. It also relates to fragments, variants and mutants of such sequences, particularly those which also encode a polypeptide having biological activity of a mammalian dopamine receptor, most particularly a mammalian $D_2$ dopamine receptor. In a preferred aspect, the dopamine receptor is human. In another preferred aspect, the sequence is that of rat $D_2$ dopamine receptor as shown in FIG. 1. Of course, the nucleic acids of this invention also include complementary strands of the foregoing, as well as sequences differing therefrom by codon degeneracy and sequences which hybridize with the aforementioned sequences.

In other preferred aspects, this invention includes nucleic acid sequences and fragments useful as oligonucleotide probes, preferably labelled with a detectable moiety such as a radioactive or biotin label. For example, such probes can hybridize with DNA encoding a polypeptide having the biological activity of a $D_2$ dopamine receptor or with DNA associated therewith, e.g., DNA providing control of a $D_2$ dopamine receptor gene or introns thereof, etc. DNA of this invention can also be part of a vector.

The invention also involves cells transformed with vectors of this invention as well as methods of culturing these cells to manufacture polypeptides, e.g., having the biological activity of a $D_2$ dopamine receptor. Preferably, the cells are of mammalian origin when used in such methods.

The invention also relates to polypeptides encoded by the foregoing nucleic acid sequences, especially to isolated mammalian dopamine receptors, preferably of human origin. The invention further relates to polypeptides which are mutants or variants of such receptors, preferably those wherein one or more amino acids are substituted for, inserted into and/or deleted from the receptor, especially those mutants which retain the biological activity of a dopamine receptor. This invention also relates to antibodies, preferably labelled, and most preferably monoclonal, capable of binding a dopamine receptor amino acid sequence, preferably wherein the latter is human, or a fragment of such an antibody.

The invention further relates to compositions comprising one of the various products mentioned above and, typically, a pharmaceutically acceptable carrier as well as to methods of employing these products to achieve a wide variety of utilitarian results.

BRIEF DESCRIPTION OF THE DRAWINGS

Various other objects, features and attendant advantages of the present invention will be more fully appreciated as the same becomes better understood when considered in conjunction with the accompanying drawings, and wherein.

a) 1: Saturation isotherms of the specific binding of $^3$H-spiperone to membranes prepared from L-RGB2Zem-1 cells and rat striatum. Results are shown from one of four independent experiments.

2: Scatchard transformation of the data.

b) Competitions curves using L-RGB2Zem-1 membranes. Representative curves are shown for inhibition of specifically bound $^3$H-spiperone by drugs in membranes from L-RGB2Zem-1 cells. Each drug was tested 3 times.

c) Table of $K_i$ values for L-RGB2Zem-1 and rat striatum. Results are geometric means of 3 experiments in which 0.5 nM $^3$H-spiperone was inhibited by various concentrations of unlabeled drug. For some drugs, inhibition curves in rat striatal tissue were fit best by assuming the presence of two classes of binding sites. The proportions of binding sites with high or low affinity for inhibitor are shown in parentheses. $K_i$ values for the class of binding sites representing 10–25% of specific binding were calculated by assuming that the radioligand was binding to serotonin receptors with a Kd value of 1 nM.

Figures 1, 4A:
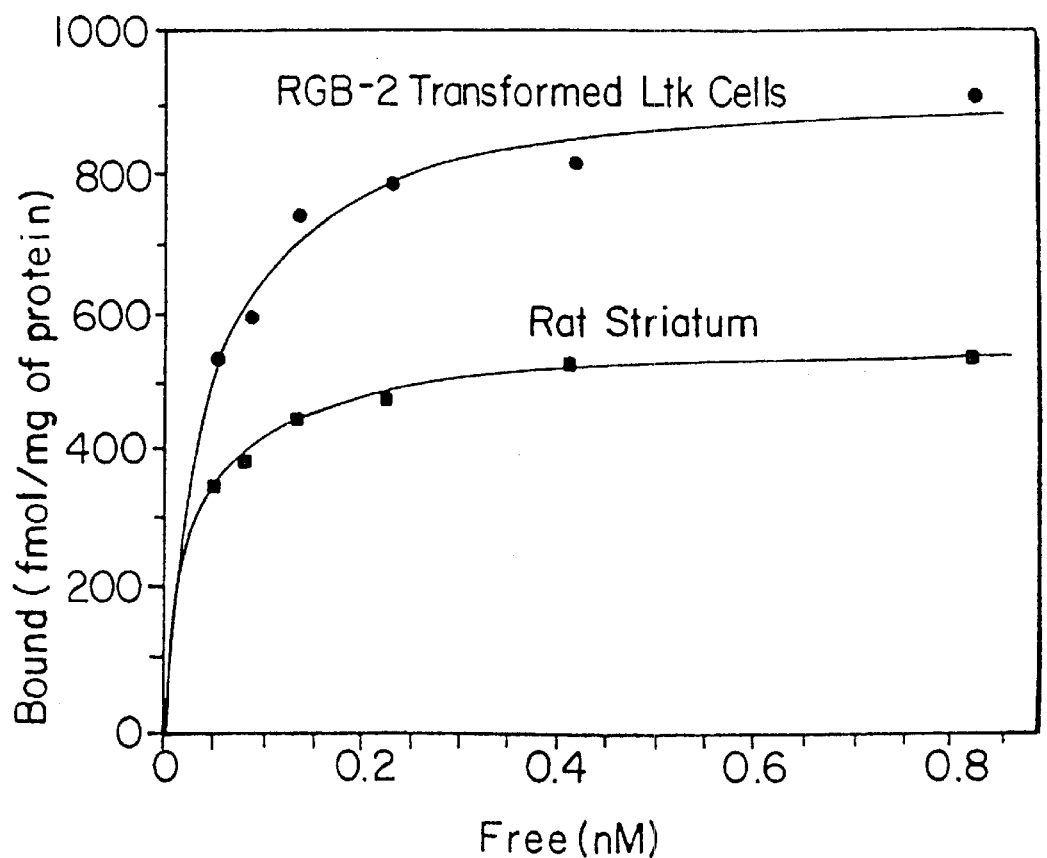
FIG. 1 shows the nucleotide sequence for the RGB-2 cDNA and deduced amino acid sequence of the rat $D_2$ dopamine receptor. The nucleotide sequence is numbered beginning with the first methionine of the long open reading frame. Nucleotide numbering appears beneath the nucleotide sequence at the right-hand end of each line. The deduced amino acid sequence is shown above the nucleotide sequence. The double underline denotes the small open reading frame in the 5' untranslated region. Postulated N-linked glycosylation sites are indicated by asterisks. Putative protein kinase A phosphorylation sites have a line above them. The intron splice junction is designated by an arrow. The poly A adenylation site is underlined.
Figure 5A:
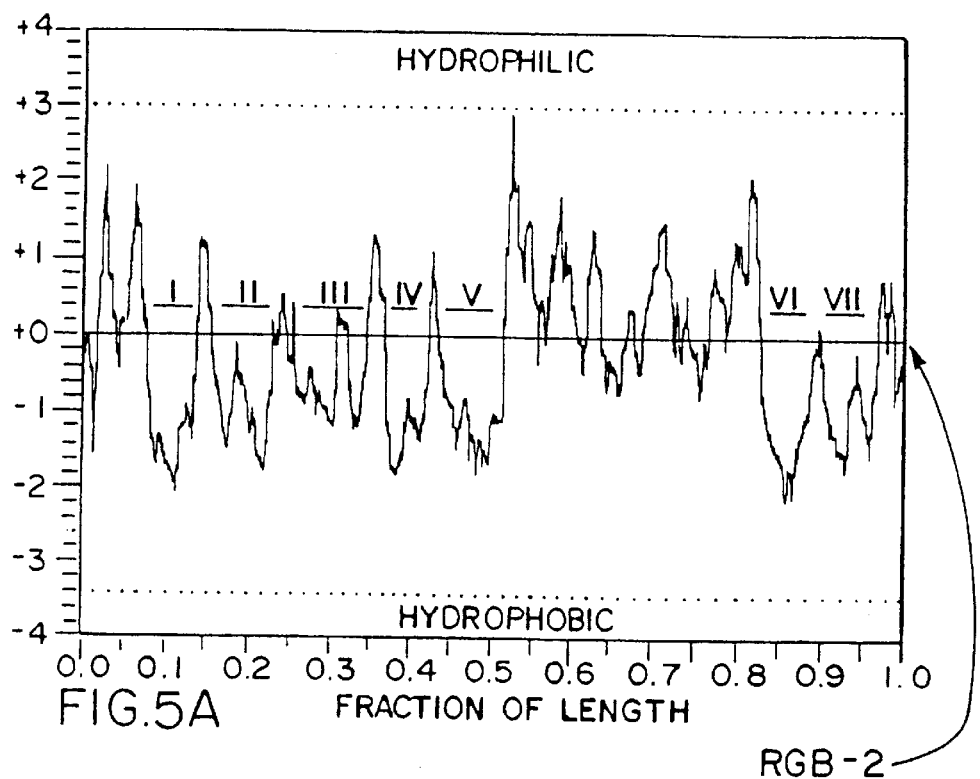
Figure 5B:
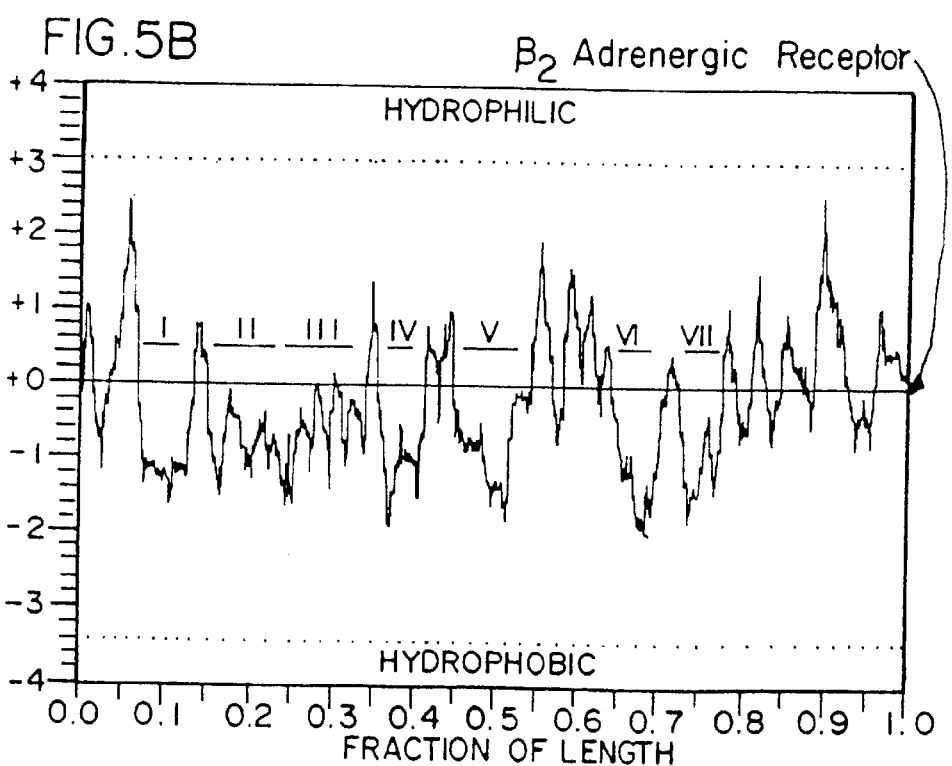
Figure 6B:
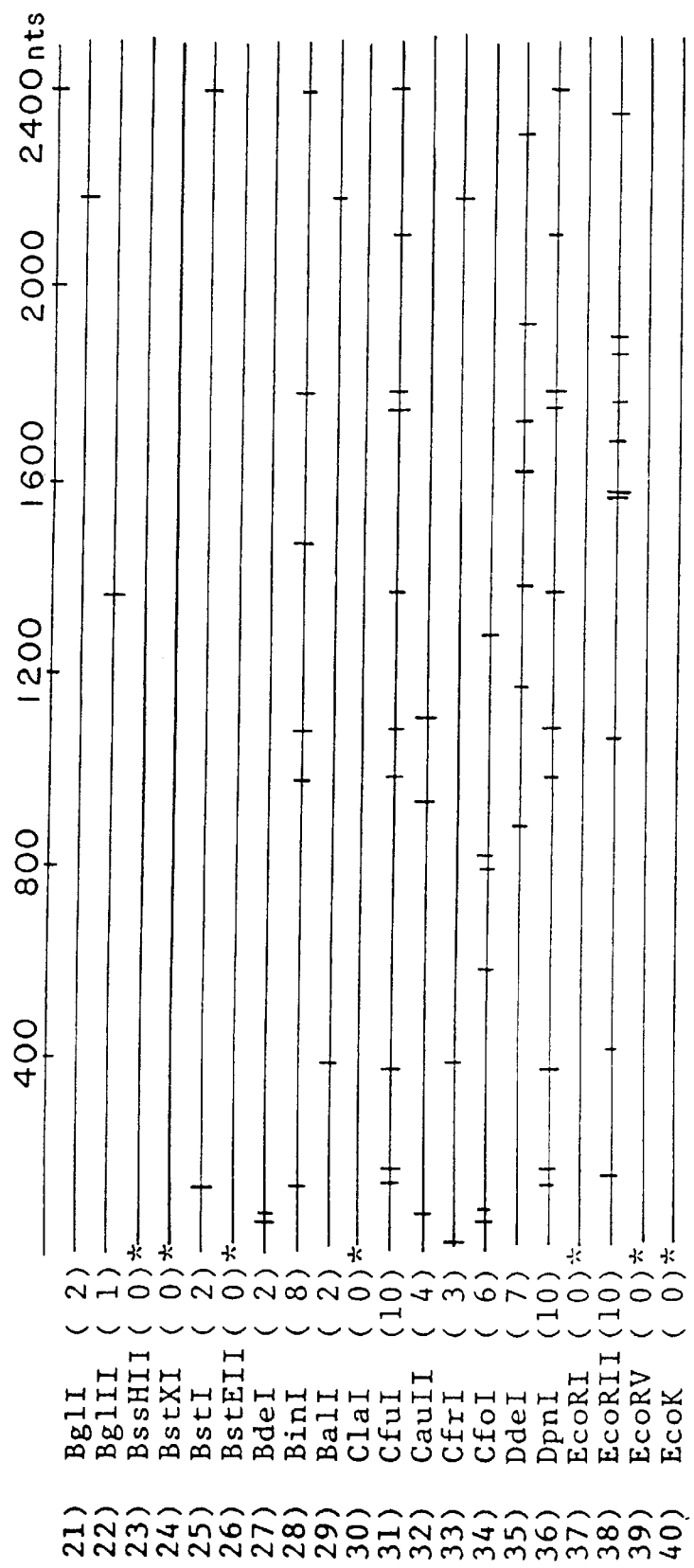
Figure 6C:
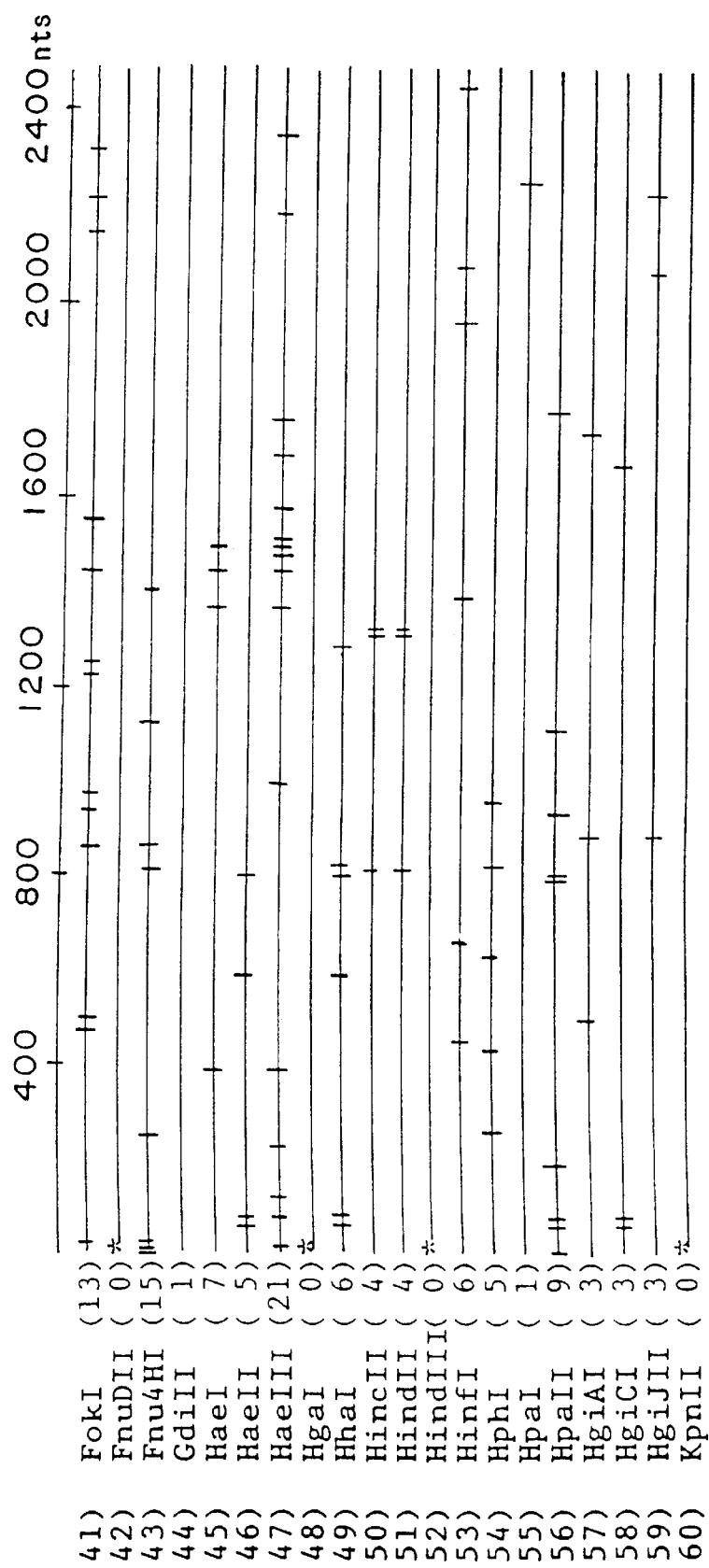
Figure 6D:
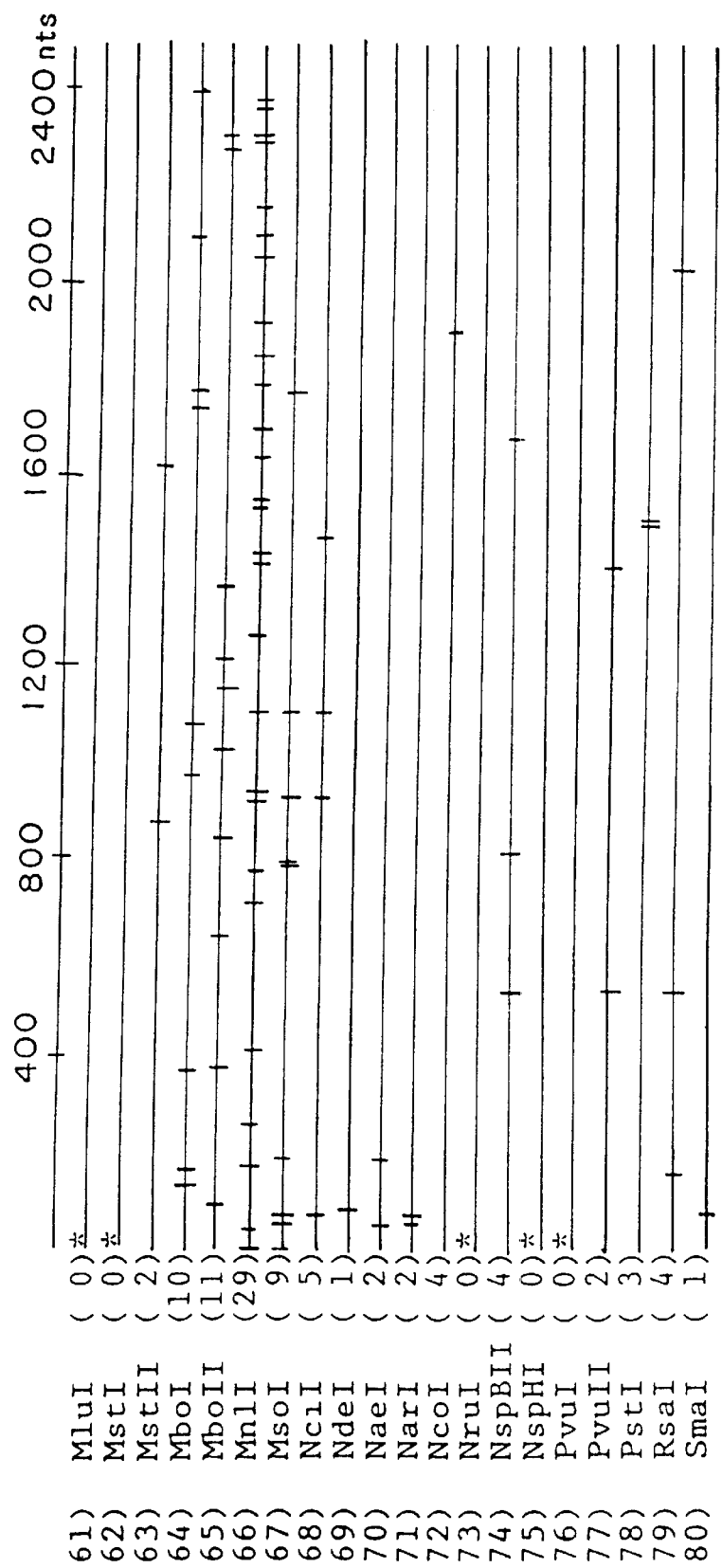
Figure 6E:
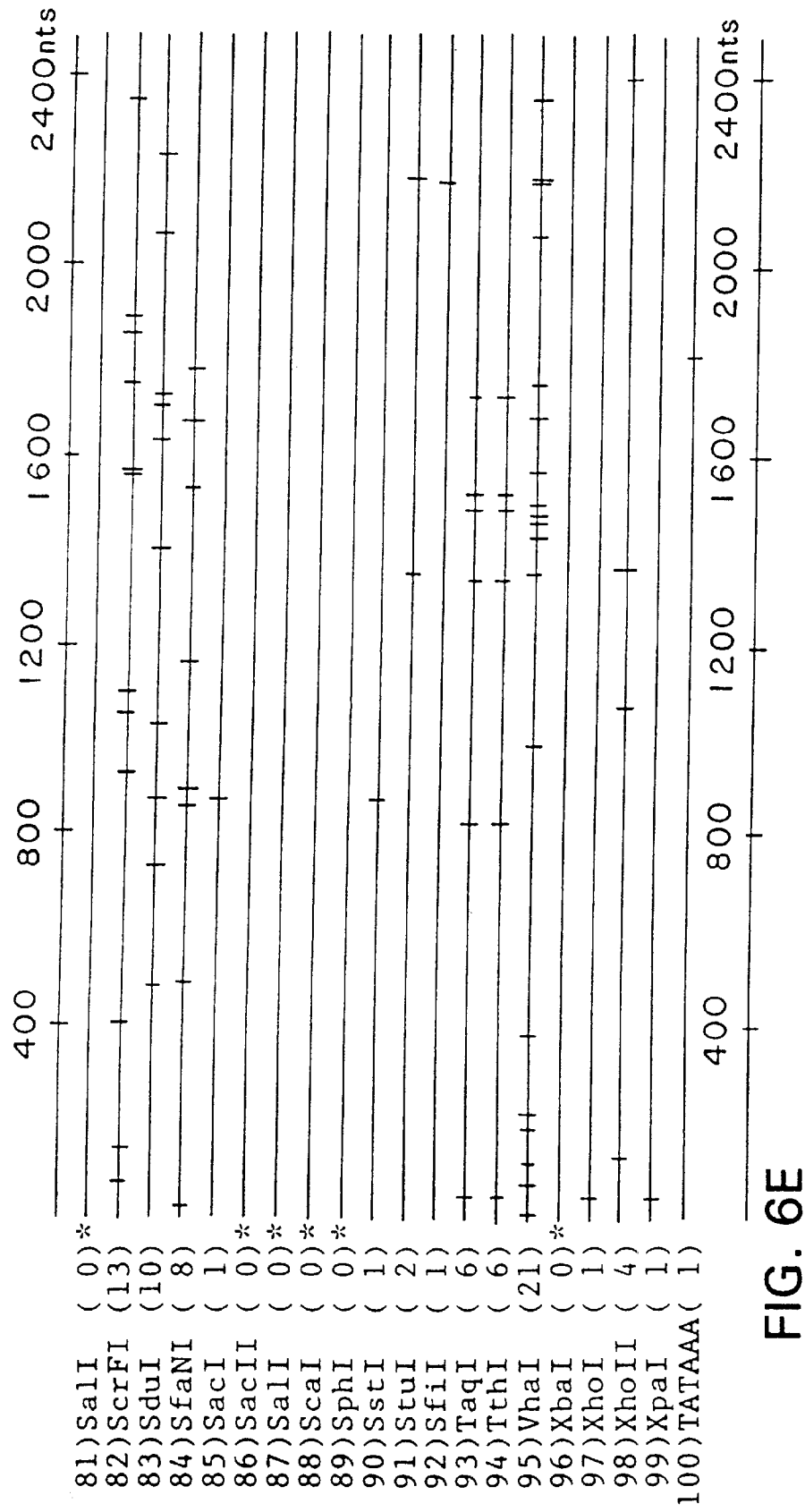

FIG. 5 shows (a) a hydrophobicity plot of the amino acid sequence shown in FIG. 1; and (b) a hydrophobicity plot of the amino acid sequence of the $\beta_2$-adrenergic receptor. The transmembrane regions are marked by the Roman numerals.

FIG. 6 shows a calculated restriction map of a 2477 base EcoRI fragment of the nucleic acid sequence shown in FIG. 1.

FIG. 7 shows a partial sequence of a human $D_2$ dopamine receptor, the middle amino acid sequence shown being the correct one.

Figure 8:
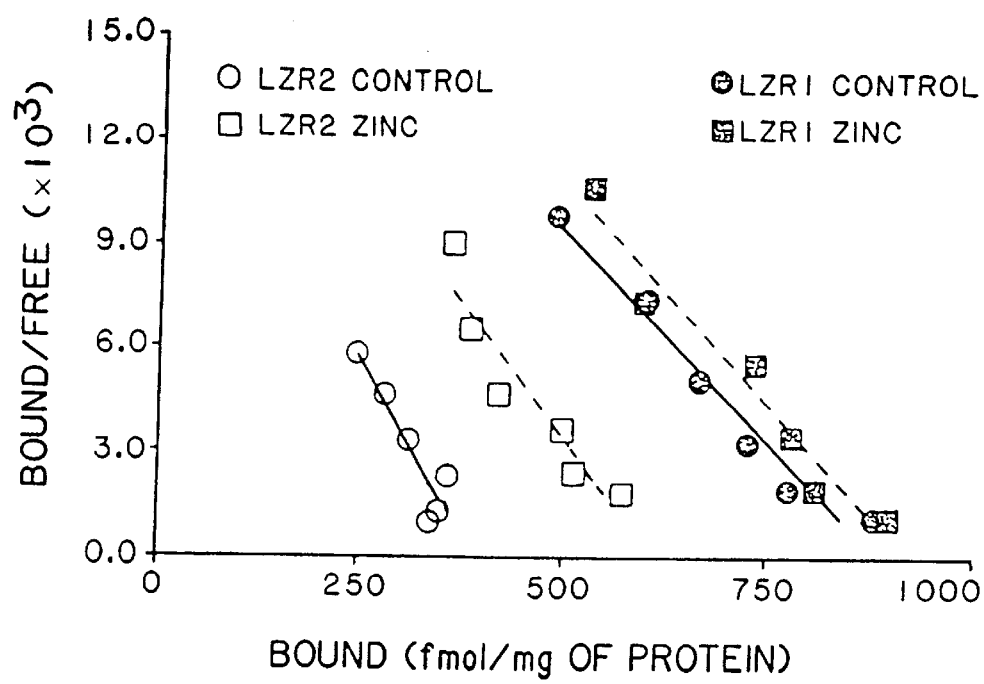

FIG. 8 shows a saturation analysis of specific [$^3$H] spiroperidol binding to LZR1 and LZR2 cells. Results shown are from representative experiments in which LZR1 and LZR2 cells were grown in control growth medium or medium to which zinc sulfate had been added, as indicated. Data are plotted as specifically bound radioligand divided by the corrected free concentration of radioligand (total added minus total bound), versus specifically bound radioligand. For zinc treatments, 100 μM zinc sulfate was added to growth medium for 16 hours. Both control and zinc-treated cells were then washed and grown in control medium for one day before harvesting. In the experiments shown, $B_{max}$ values determined by nonlinear regressions analysis were 876 and 914 fmol/mg of protein for control LZR1 cells or LZR1 cells treated with zinc, respectively. $B_{max}$ values for control or zinc-treated LZR2 cells were 385 and 593 fmol/gm of protein, respectively.

FIG. 9 shows the inhibition of radioligand binding by agonists. Results are plotted as specific binding, expressed as a percentage of specific binding in the absence of competing drug, versus the log of the concentration of competiting drug. Membranes were prepared from LZR1 cells as described in the text.

A. Curves from a single experiment are shown for inhibition of the binding of [$^3$H]spiroperidol by agonists. Each drug was tested twice. In this experiment, the free concentration of [$^3$H]spiroperidol was 230 pM, and the $K_D$ value for [$^3$H]spiroperidol was 60 pM. $K_I$ values and Hill coefficients in this experiment were 5 nM and 1.05 for bromocriptine, respectively, 790 nM and 0.89 for (−)3-PPP, 8 μM and 1.0 for quinpirole, 31 μM and 1.05 for (+)3-PPP, and 0.3 mM and 0.72 for LY181990.

B. Results are shown from one of four independent experiments in which the effect of GTP and NaCl on the inhibition of [$^3$H]spiroperidol binding by DA was determined. Concentrations of [$^3$H]spiroperidol ranged from 323 to 498 pM. In this experiment, the concentration of radioligand was 323 pM. Open circles represent inhibition by DA in the presence of 0.1 mM GTP and 120 mM NaCl, whereas closed circles represent inhibition in the absence of added GTP and NaCl. $IC_{50}$ values and Hill coefficients in this experiment were 29 μM and 0.65, respectively, in the absence and 115 μM and 1.03 in the presence of GTP and NaCl.

Figure 10A:
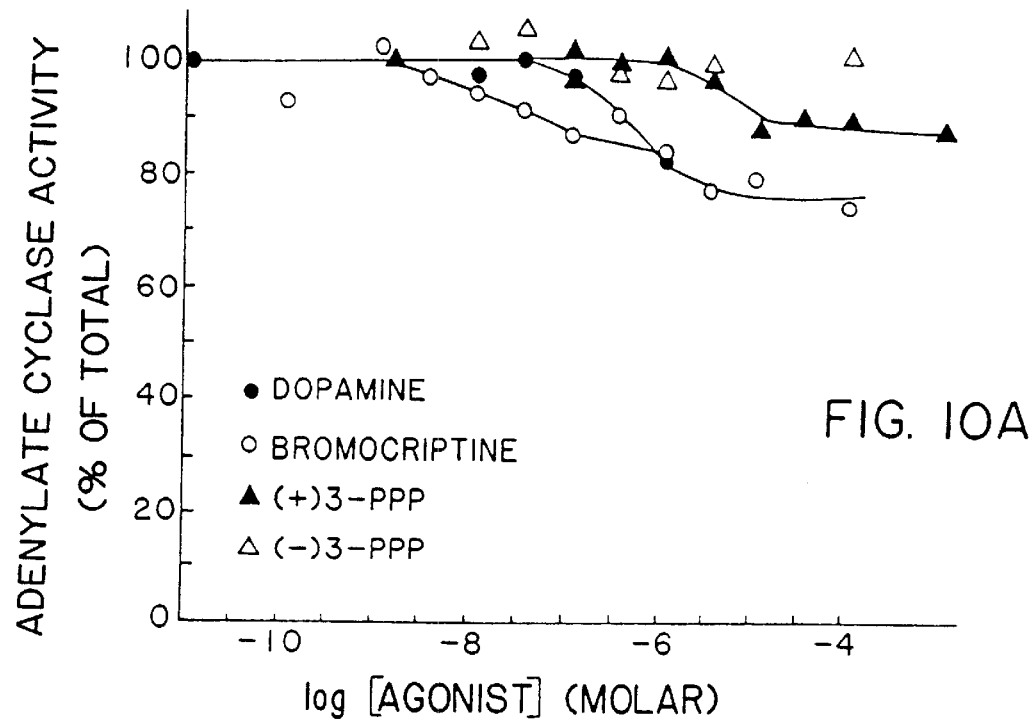
Figure 10B:
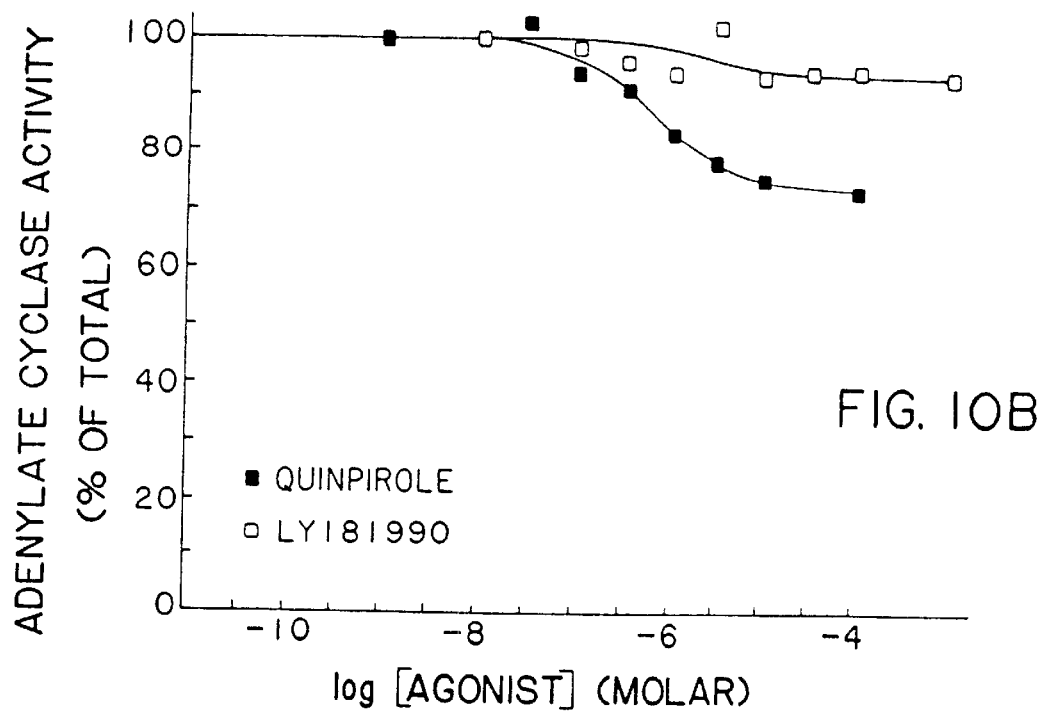

FIG. 10 shows the inhibition of adenylate cyclase activity in LZR1 cells. Agonists were tested for inhibition of adenylate cyclase activity in membranes prepared from LZR1 cells. Approximately 50 to 100 μg of protein was used in each assay. Results are shown as [$^{32}$P]cAMP/mg of protein/ min., expressed as a percentage of total activity in the presence of 10 μM forskolin. Representative dose-response curves are shown for six drugs, each tested at least three times. Data are plotted as enzyme activity versus the log of the concentration of drug. No curve is plotted for the data for (−)3-PPP, since no inhibition was observed. In the experiments shown in this figure, basal and forskolin-stimulated activity ranged from approximately 0.8 to 1.5 and 8.5 to 15.8 pmol/mg of protein/min., respectively.

Figure 11:
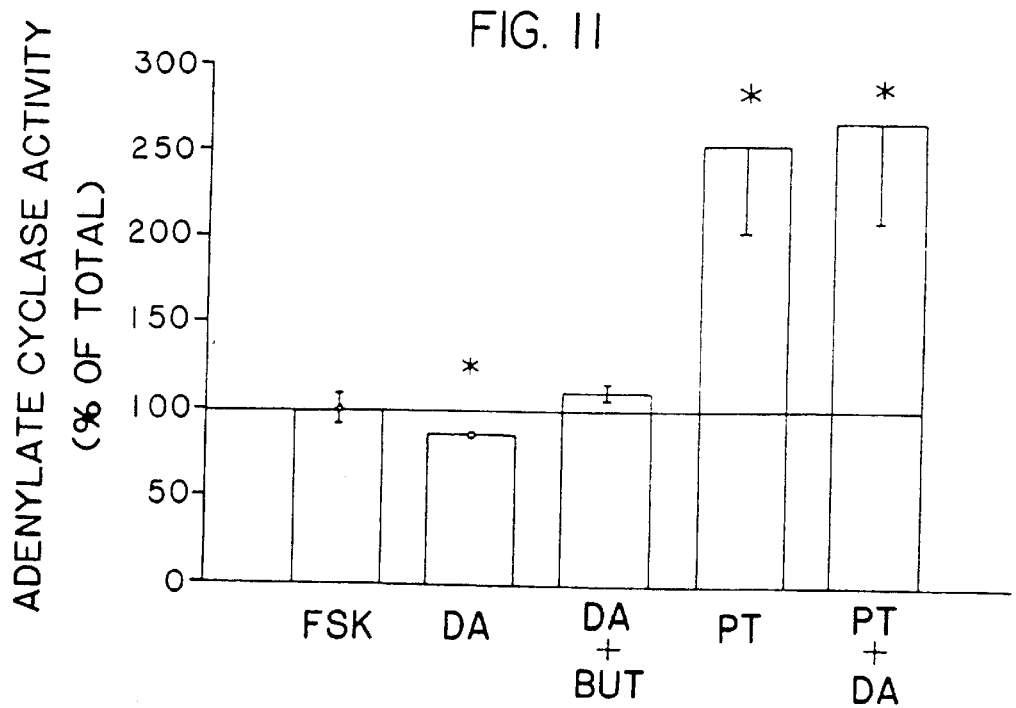

FIG. 11 shows the blockade of DA-sensitive adenylate cyclase. Results shown are means of three experiments ±SE, plotted as the percentage of total activity in the presence of 10 μM forskolin. Forskolin (FSK) was present in all the experiments shown, together with 10 μM dopamine (DA) or DA and 10 μM (+)-butaclamol (BUT) as indicated. Some cells were treated with pertussins toxin (PT) before harvesting for determination of enzyme activity. Basal activity in control and PT-treated cells was 1.2±0.07 and 1.6±0.15 pmol/mg of protein/min., respectively. Total forskolin-stimulated activity in control cells (FSK) was 11.9±1.0 pmol/mg of protein/min. *$p<0.05$ compared to FSK in control cells, as determined by a t test for paired means.

FIG. 12 shows the reversal of dopamine inhibition by pertussis toxin pretreatment. Data presented for membrane adenylate cyclase activity represent means (x) with standard error (S.E.) and % inhibition (% Inh.) below. % Inhibition was calculated from the equation 100×[1-(S-B/I-$B_I$)] where B, S, and I are values of basal activity, activity in the presence of stimulator (S) or inhibitor (I), respectively and $B_I$ is basal activity in the presence of inhibitor. Results were obtained from parallel assays in controls and cells pretreated (16 h, 50 ng/ml) with pertussis toxin (indicated as +P.T.).

(A) Adenylate Cyclase. Membranes for cyclase assay were exposed acutely to 10 μM forskolin (FSK) or 100 μM dopamine (DA), and adenylate cyclase activity expressed as pmol/mg protein/min.

(B) Intracellular cAMP. Cells were treated acutely with VIP (200 nM) and dopamine (1 μM) and cAMP accumulation (expressed as pmol/dish) was measured in cell extracts.

(C) Extracellular cAMP. Media samples from the same dishes of cells were assayed for cAMP accumulation expressed as pmol/dish.

Figure 13:
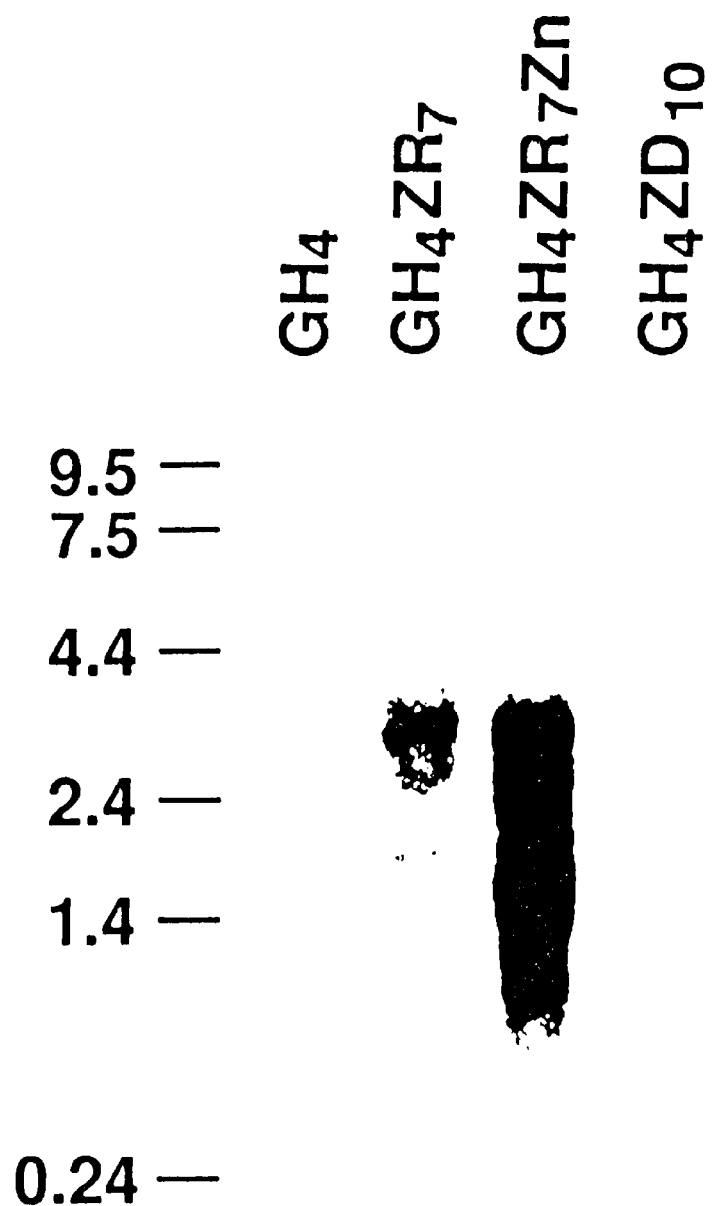

FIG. 13 shows the expression of specific dopamine-$D_2$ receptor mRNA and specific binding in $GH_4ZR_7$ transfectant cells.

(A) Northern blot analysis of $GH_4C_1$ cell total RNA' (20 μg/lane). Y-axis indicate the migration of RNA molecular weight standards (kb).

(B)(1) Specific binding of $^3H$-spiperone to membranes prepared from $GH_4ZR_7$ cells was characterized by saturation analysis (see "Experimental Procedures", Example 2). Data from one of four independent experiments are plotted as specifically bound radioligand (ordinate) versus corrected free radioligand concentration (total added minus total bound). Calculated $K_D$ and $B_{max}$ values for this experiment were 60 pM and 1165 fmol/mg protein.

(B)(2) Transformation of the data by the method of Scatchard which are plotted as specific bound/free (Y-axis) vs. specific bound concentrations of $^3H$-spiperone (X-axis).

(C) Displacement of specific $^3H$-spiperone binding by dopamine: effect of GTP/NaCl. $GH_4ZR_7$ cell membranes were incubated with $^3H$-spiperone (0.47 nM) and indicated concentrations of dopamine (X-axis) in the absence (o) or presence (·) of 100 AM GTP/120 mM NaCl. Results are shown for one of four experiments. Calculated $IC_{50}$ and Hill coefficient values for dopamine in the experiment shown were 16 μM and 0.61 in the absence of GTP/NaCl, and 56 μM and 0.85 in the presence of GTP/NaCl.

Figure 14A:
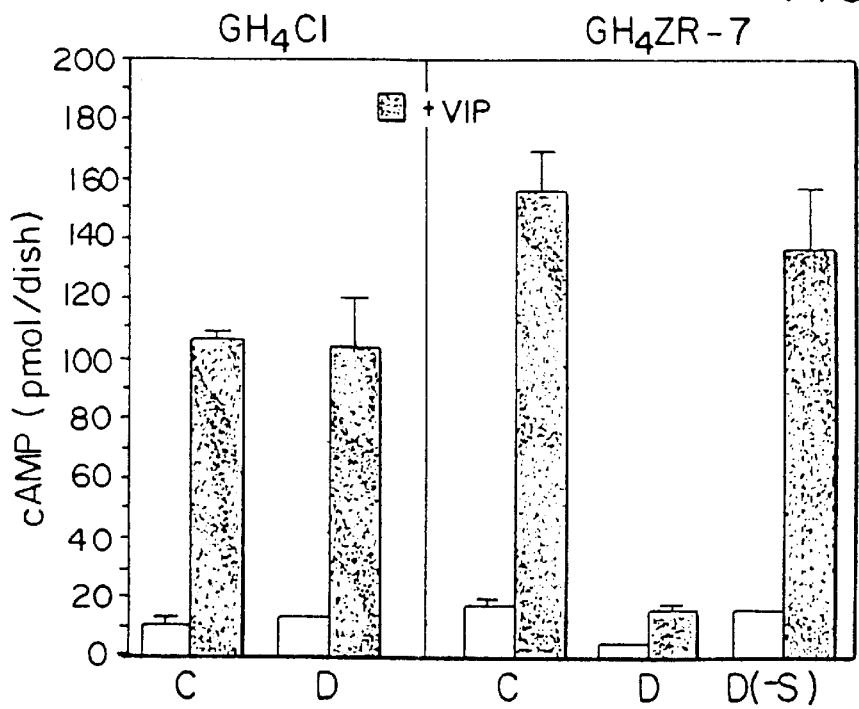

FIG. 14 shows the inhibition of cAMP accumulation and PRL release by dopamine in $GH_4ZR_7$ cells. Incubations were performed in triplicate as described in "Experimental Procedures", Example 2.

(A) Inhibition of extracellular cAMP accumulation by dopamine. Parallel dishes of $GH_4C_7$ and $GH_4ZR_7$ cells were incubated with concentrations of VIP, dopamine (D), and (−)-sulpiride (−S) of 250 nM, 10 μM and 5 μM, respectively. Untreated controls are denoted as "C". Media were collected and assayed for cAMP (ordinate) expressed as pmol/dish.

(B) Inhibition of intracellular cAMP accumulation by dopamine in $GH_4ZR_7$ cells. Cell extracts were assayed for cAMP, expressed on the ordinate. Drug concentrations were as in (A), except (+)-sulpiride (+S), 5 μM.

(C) Inhibition of stimulated PRL release by dopamine in $GH_4ZR_7$ cells. Media samples were assayed for PRL (ordinate) after the indicated treatments. The concentrations of VIP, TRH, dopamine (D), and (−)-sulpiride (−S) were 200 nM, 200 nM, 100 nM, and 2 μM, respectively.

Figure 15A:
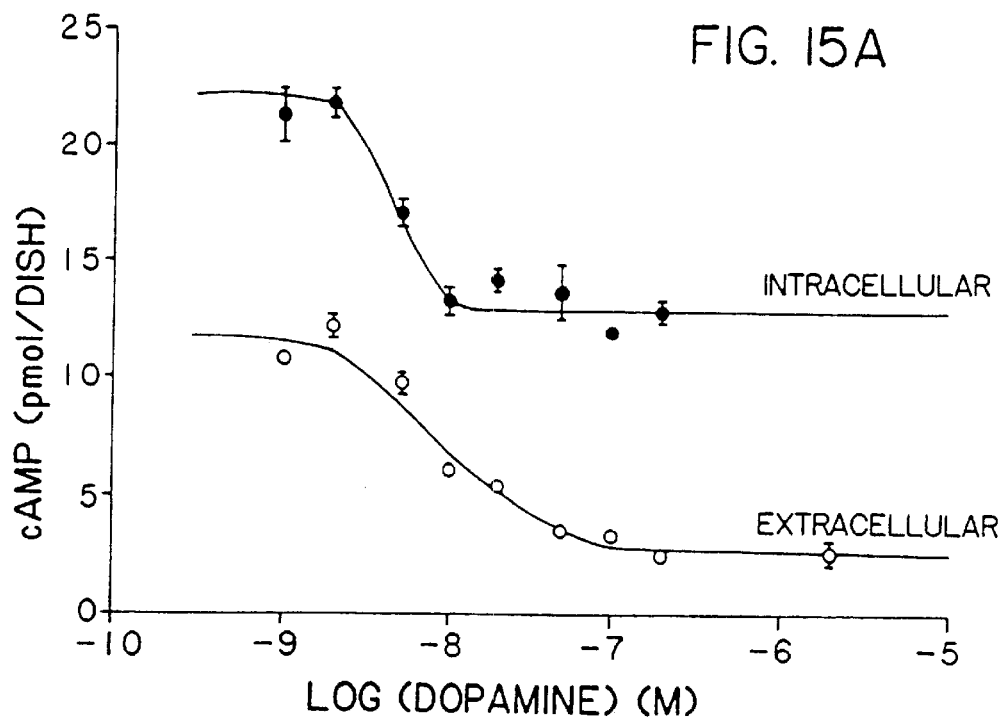
Figure 15B:
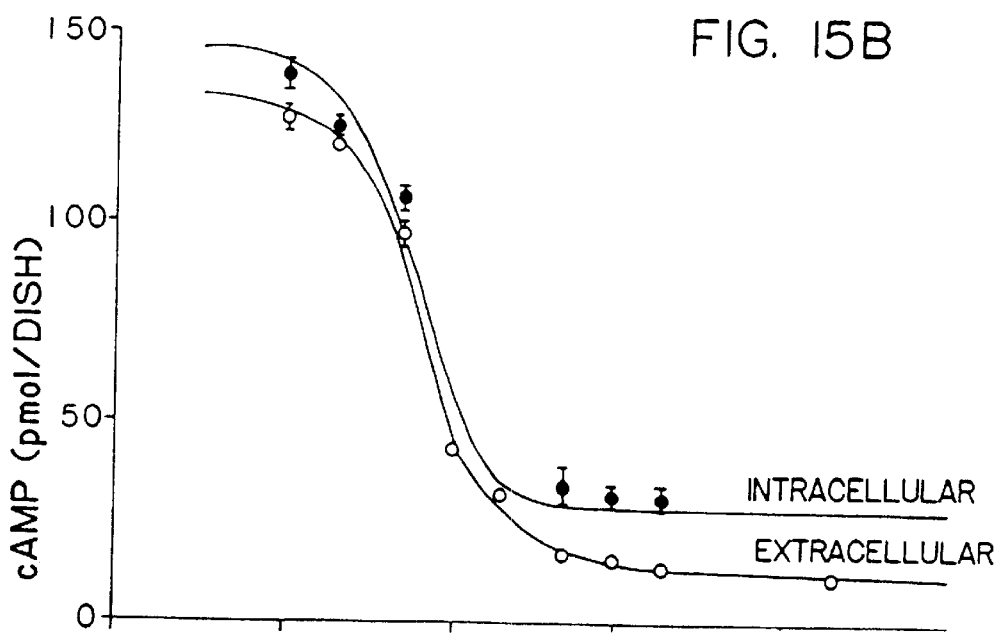

FIG. 15 shows dose-response relations for dopamine inhibition of basal and VIP-enhanced cAMP accumulation in $GH_4ZR_7$ cells.

(A) Basal intra- (·) and extracellular (o) cAMP accumulation in the presence of indicated concentrations of dopamine. Basal cAMP levels in the absence of dopamine were 22±6 pmol/dish (intracellular) and 12.4±0.6 pmol/dish (extracellular). $EC_{50}$ values for dopamine actions were 4.9 nM (intracellular) and 8.5 nM (extracellular).

(B) VIP-enhanced intra- (·) and extracellular (o) cAMP accumulation in the presence of indicated dopamine concentrations. VIP (250 nM)-enhanced levels of intra- and extracellular cAMP (in the absence of dopamine) were 145±1.2 pmol/dish and 146±2.8 pmol/dish, and basal cAMP levels were 35±1.6 pmol/dish and 15±0.2 pmol/dish, respectively. $EC_{50}$ values for dopamine inhibition were 5.5 nM (intracellular) and 5.8 nM (extracellular).

Figure 16:
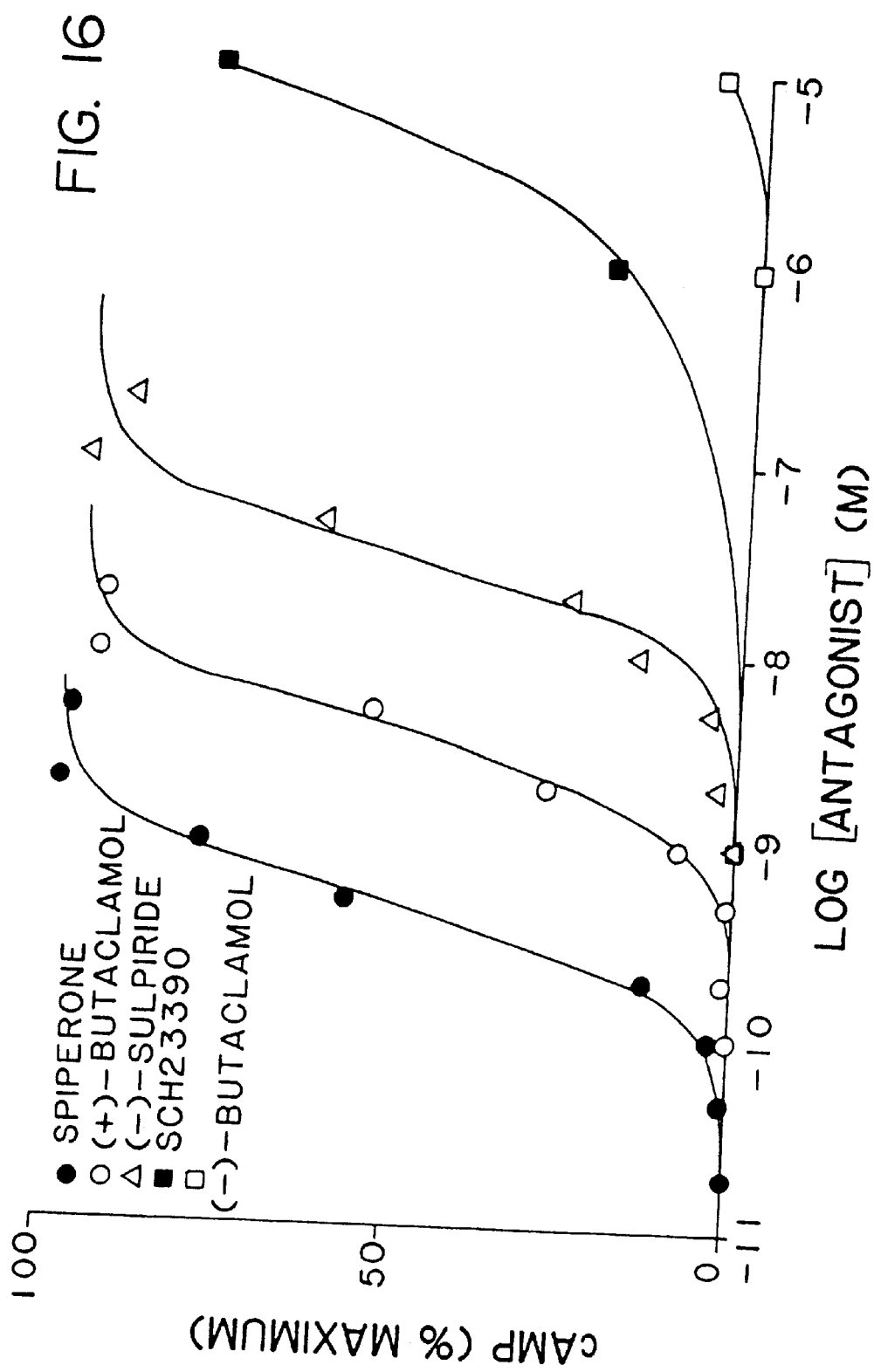

FIG. 16 shows the specific blockade of dopamine-induced inhibition of VIP-enhanced cAMP accumulation. $GH_4ZR_7$ cells were incubated in FAT medium (see "Methods", Example 2) in the presence of 250 nM VIP and 100 nM dopamine, and indicated concentrations of various dopamine antagonists, and extracellular levels of cAMP measured. Data are plotted as percent of maximal cAMP levels versus the logarithm of indicated concentrations of dopamine antagonists. The standard error of triplicate determinations was less than 8%. Basal and VIP-enhanced cAMP levels (in the absence of dopamine and antagonists) were 25.8±1.6 pmol/dish and 214±14 pmol/dish. $IC_{50}$ and estimated $K_i$ values for antagonism of dopamine actions were: spiperone, 0.56 nM and 30 pM; (+)-butaclamol, 4.5 nM and 0.2 nM; (−)-sulpiride 38 nM and 1.8 riM; SCH23390, >1 μM; (−)-butaclamol, >10 μM. Estimated $K_I$ were calculated from the equation $K_I$–$IC_{50}/(1+([DA]/EC_{50}))$, where [DA] is 100 nM and the $EC_{50}$ for dopamine is 6 nM. Spiperone, (+)-butaclamol and (−)-sulpiride alone did not alter basal cAMP levels.

FIG. 17 shows the inhibition of adenylate cyclase by dopamine-$D_2$ agonists. Inhibition of adenylate cyclase activity was assessed in the presence of 10 μM forskolin. Data are plotted as the mean of triplicate assays, with enzyme activity expressed as a percentage of total activity versus the logarithm of drug concentration. Average basal adenylate cyclase activity was 4.6±0.2 pmol/mg protein/min and total forskolin-stimulated activity was 63.8±0.2 pmol/mg protein/min. $EC_{50}$ values and maximal inhibition for the experiments shown were 79 nM and 57%, respectively, for dopamine, 200 nM and 49% for quinpirole, 5 nM and 23% for bromocriptine, and 600 μM and 40% for (+)-3-PPP.

FIG. 18 shows the nucleotide sequence of the human pituitary dopamine $D_2$ receptor cDNA. The deduced amino acid sequence is indicated above the human cDNA. Below is the nucleotide sequence of the cloned rat cDNA (see Reference 9, Example 3) and the amino acids which differ between the two clones. Boxed regions, numbered I-VII, represent the putative transmembrane domains. Triangles indicate the exon/intron splice junctions; a period is one missing base pair; asterisks identify potential N-linked glycosylation sites and targets of protein kinase A phosphorylation are underlined. The polyadenylation signal is double underlined.

Figure 19:
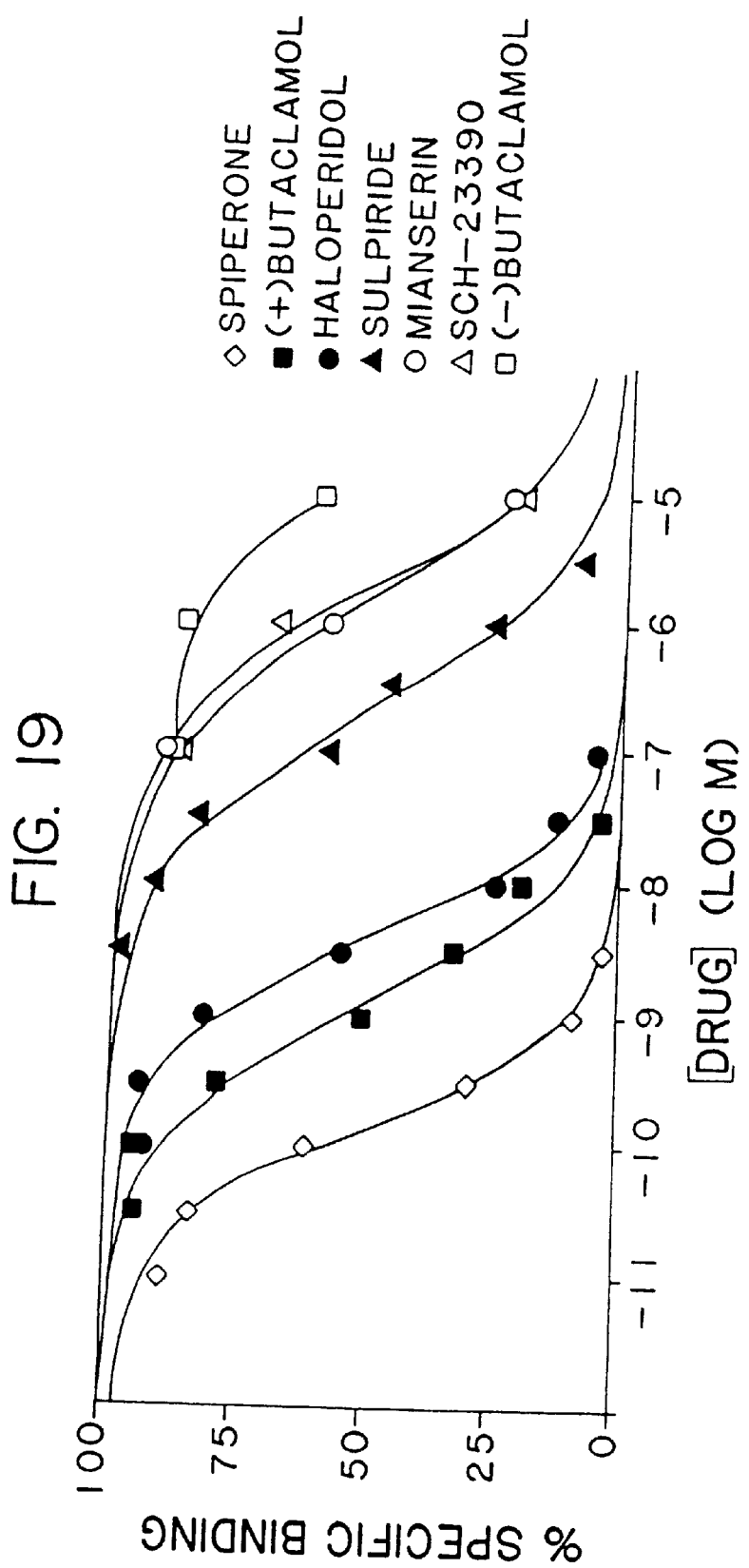

FIG. 19 shows competition curves of [$^3H$]-domperidone binding to L-hPitD$_2$Zem membranes. The radioligand was used at a concentration of 1 nM, and specific binding was defined using 1 μM (+) butaclamol. Data are shown for one of three experiments.

FIG. 20 shows Southern blot of human genomic DNA. The genomic BamHI 1.6-kb fragment containing exon 7 was prepared from λHD2G1 and used as probe (specific activity, 2×10$^8$ cpm). DNA was digested with BamHI (lane 1), BglII (lane 2), BamHI/BglII (lane 3), and HindIII (lane 4).

Figure 21:
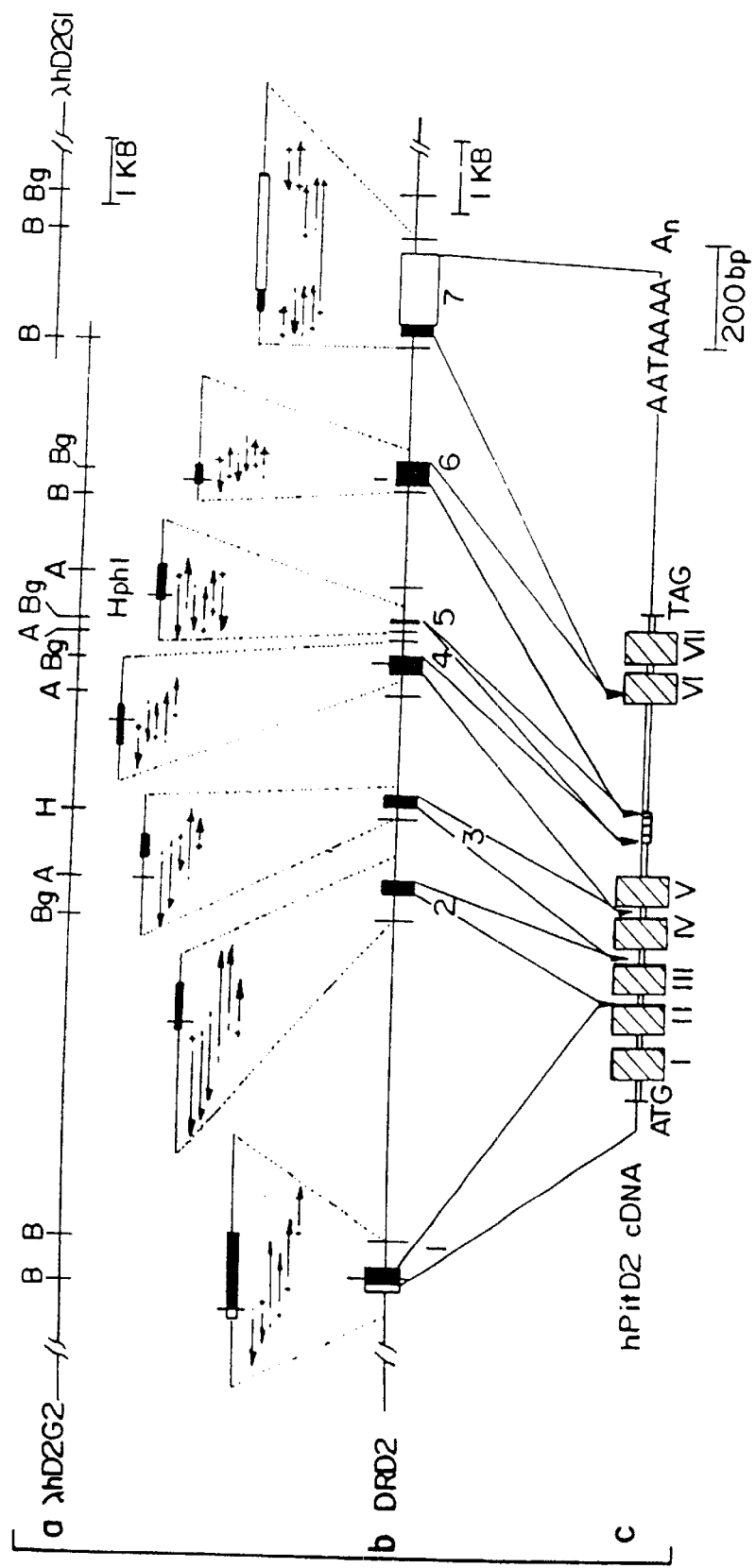

FIG. 21 is a schematic representation of the human dopamine $D_2$ receptor gene and pituitary cDNA.

(a) Restriction map of the two overlapping genomic phase, λhD2G1 and λhD2G2; A, ApaLI; B, BamHI; Bg, BglII; H, HindIII.

(b) Diagram of the human gene locus DRD2. Exons, indicated by the boxes, are numbered. The solid boxes indicate regions of coding sequence and open boxes, non-translated sequence. The genomic sequencing strategy is expanded above the gene. These regions are not drawn to scale. DNA sequences (+indicates sense and −, antisense sequence) were read from the bottom to the top of each ladder in the directions indicated by the arrows (pointing to the right, 5' to 3' and to the left, 3' to 5'). The 87-bp exon is No. 5. Intron sizes were determined by Southern blotting and restriction mapping and are accurate to within 10 percent, with one exception: intron 1 is accurate to within 20 percent.

(c) The structure of the human pituitary cDNA. Exon/intron splice junctions are indicated by triangles. Regions encoding transmembrane domains I-VII are enclosed by boxes containing wavy lines. The 87-bp sequence is striped. The sites for translation initiation (ATG) and termination (TAG) are indicated, as is the polyadenylation signal sequence (AATAAAA).

FIG. 22 shows a comparison of $IC_{50}$ values (nM) for L-hPitD2Zem, L-RGB2Zem1 and rat striatum.

FIG. 23 shows the exon/intron junctions in the human dopamine $D_2$ receptor gene.

DISCUSSION

This invention takes advantage in a unique way of nucleotide sequence similarities among members of a gene family coding for receptors that are coupled to G proteins. By using a unique hamster $\beta_2$-adrenergic receptor ($\beta_2AR$) gene as a hybridization probe, a cDNA encoding the rat $D_2$ dopamine receptor was identified and isolated. The receptor has been characterized on the basis of three criteria: 1) the deduced amino acid sequence which reveals that it is a member of the family of G protein-coupled receptors, 2) the tissue distribution of the corresponding mRNA which parallels that known for the $D_2$ dopamine receptor, and 3) the pharmacological profile of Ltk- cells transformed with the cDNA.

A rat genomic library was screened under low-stringency hybridization conditions with a nick-translated 1.3 kb HindIII fragment containing most of the coding region of the hamster $\beta_2AR$ gene. The hamster $\beta_2AR$ receptor gene was cloned from a partial hamster lung λgt10 genomic DNA library (constructed from size fractionated (5–7 kb) EcoRI digested DNA) with two oligonucleotide probes (30-mer, TCTGCTTTCAATCCCCTCATCTACTGTCGG; 40-mer, CTATCTTCTGGAGCTGCCTTTTGGCCACCTGGAAG-ACCCT) designed from the sequence of Dixon et al. (9). The 1.3 kb HindIII fragment of the hamster $\beta_2AR$ gene which contains most of the coding sequence of that gene was labeled by nick translation and used to probe a rat genomic DNA library in the commercially available phage EMBL3. The library was transferred to Colony Plaque Screen filters (NEN) and screened with the $^{32}p$ labeled probe using the following hybridization conditions: 25% formamide, 5×SSC, 5×Denhardts, 0.1% sodium pyrophosphate, 1% SDS and salmon sperm DNA (100 μg/ml) at 37° C. Filters were washed in 2×SSC and 0.1% SDS at 55° C.

Several clones were found to hybridize to the hamster probe using these conditions. One clone, called RGB-2, was found to have a 0.8 kb EcoRI-PstI fragment that hybridized to the hamster $\beta_2AR$ probe in Southern blot analysis. This fragment was sequenced and shown to have a stretch of nucleotides with a high degree of identity (32 out of 40 bases) to the nucleotide sequence of transmembrane domain VII of the hamster $\beta_2AR$. One of the possible reading frames demonstrated a significant similarity to the amino acid sequence of transmembrane domains VI and VII of the hamster $\beta_2AR$. Within this genomic fragment there is also a 3' intron splice site (10) and 400 bp of putative intronic sequence.

The 0.8 kb EcoRI-PstI fragment (nick translated) was used to probe a rat brain cDNA library in λgt10 with the same hybridization conditions as above except that 50% formamide was used. Washing of the filters was performed in 0.2×SSC and 0.1% SDS at 65° C. Under these high stringency hybridization conditions, two positive clones of about 2.5 kb in size were identified from a library of 500,000 clones. DNA sequence was obtained from both strands by the Sanger dideoxy chain determination method using Sequenase (U.S. Biochemical) (26). Sequence and restriction analysis indicated that the two clones were replicas of a single clone and contained the sequence of the genomic fragment that had been used as a probe. When the RGB-2 cDNA was used as a hybridization probe in Northern blot analysis of mRNA isolated from rat brain, a band of approximately 2.5 kb was detected. This finding indicated that the RGB-2 clone was nearly full length.

FIG. 1 shows the nucleotide sequence of 2455 bases for the RGB-2 cDNA. The longest open reading frame in this cDNA codes for a 415 amino acid protein (relative molecular weight (Mr=47,064)) also shown in the-figure. This molecular weight is similar to that reported for the deglycosylated form of the $D_2$ dopamine receptor as determined by SDS polyacrylamide gel electrophoresis (11). An in-frame dipeptide which is 36 bases upstream from the putative initiation site is found in the 5' untranslated region of the RGB-2 cDNA. A small open reading frame has been observed in the 5' untranslated sequence of the $\beta_2AR$ mRNA (9).

Figures 2, 4A:
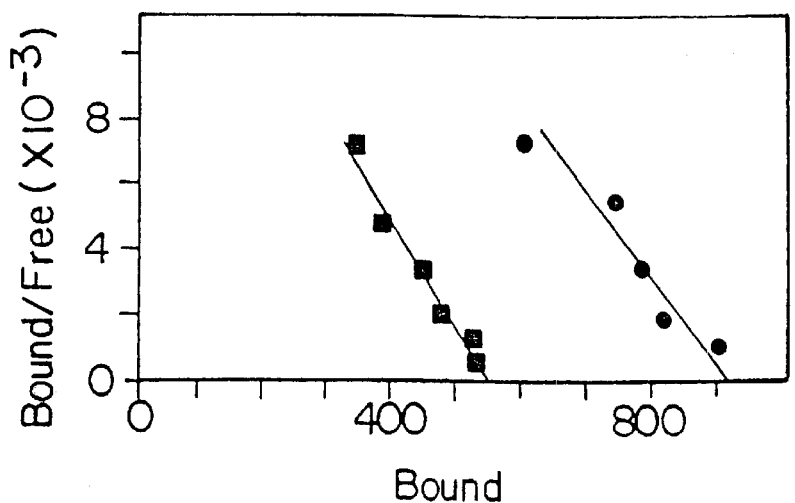
FIG. 2 shows the alignment of the amino acid sequences of the rat $D_2$ dopamine receptor, the hamster $\beta_2$-adrenergic receptor, the human $\alpha_2$-adrenergic receptor, the human G-21 (serotonin 1a) receptor, the porcine muscarinic M receptor and the bovine substance K receptor. Amino acids enclosed in solid lines and shaded represent residues that are identical in at least two other Sequences when compared to the $D_2$ dopamine receptor. The putative transmembrane domains are indicated by brackets labeled by Roman numerals. The numbers of residues in the variable third cytoplasmic loop and at the C-terminus are in parentheses.

Several structural features of the protein deduced from the RGB-2 cDNA demonstrate that it belongs to the family of G protein-coupled receptors. The hydrophobicity plot of the protein sequence (FIG. 5) shows the existence of seven stretches of hydrophobic amino acids which could represent seven transmembrane domains (8). Moreover, the primary amino acid sequence of RGB-2 shows a high degree of similarity with other G protein-coupled receptors (FIG. 2). The regions of greatest amino acid identity are clustered within the putative transmembrane domains. Within these domains the RGB-2 protein has a sequence identity of 50% with the human $\alpha_2$-adrenergic receptor (12), 42% with the human G-21 receptor (13), 38% with the hamster $\beta_2AR$-adrenergic receptor (9), 27% with the porcine $M_1$ receptor (14), and 25% with the bovine substance K-receptor (15).

Thirdly, RGB-2 has several structural characteristics common to the members of the family of G protein-coupled receptors. There are three consensus sequences for N-linked glycosylation in the N-terminus with no signal sequence. The Asp 80 found in transmembrane domain II is conserved in all known G protein-coupled receptors. In transmembrane domain III there is Asp 114 for which a corresponding Asp residue is found only in receptors that bind cationic amines (16). Phosphorylation has been proposed as a means of regulating receptor function (17). A potential site for phosphorylation by protein kinase A exists at Ser 228 in the third. cytoplasmic loop. In the C-terminal portion of the rhodopsins and α-adrenergic receptors are found many Ser and Thr residues which are potential substrates for receptor kinases (18). In contrast, the short C-terminus of RGB-2 has no Ser and Thr residues. However, as is the case for the $\alpha_2$-adrenergic receptor, RGB-2 has many Ser and Thr residues (22 residues) in the third cytoplasmic loop which could serve as phosphorylation substrates. RGB-2 contains a large cytoplasmic loop (135 amino acids) between transmembrane domains V and VI with a short C-terminus (14 amino acids). This structural organization is similar to other receptors which are coupled by $G_i$ (inhibitory G protein) such as the $_2$-adrenergic receptor and the $M_2$ muscarinic receptor. Unlike the members of the adrenergic and muscarinic receptor families, the RGB-2 gene has at least one intron in its coding sequence which is located in transmembrane domain VI.

Figure 3:
FIG. 3 shows a Northern blot analysis of RGB-2 transcripts in rat brain and pituitary. Each lane contained 20 μg of total RNA. Numbers on the right indicate molecular weight as determined from RNA size markers (BRL). A: olfactory bulb; B: hippocampus; C: cerebellum; D: posterior cortex; E: anterior cortex; F: thalamus; G: hypothalamus; H: medulla; I: amygdala; J: mesencephalon; K: septum; L: posterior basal ganglia; M: anterior basal ganglia; N: neurointermediate lobe of pituitary; O: anterior lobe of the pituitary.

As a first step towards determining the identity of RGB-2, the tissue distribution of the RGB-2 mRNA was examined by Northern blot analysis (FIG. 3).

Brain tissue was dissected from male Sprague Dawley rats and RNA isolated according to Chirgwin et al. (27) and Ullrich et al. (28). For Northern blotting, RNA was denatured using glyoxal and DMSO and run on 1.2% agarose gels. After electrophoresis, RNA was blotted onto a nylon membrane (N-Bond, Amersham) and baked for 2 hours at 80° C. The membranes were prehybridized in 50% formamide, 0.2% PVP (M.W. 40,000), 0.2% ficoll (M.W. 400,000), 0.05 M Tris pH 7.5, 1M NaCl, 0.1% PPi, 1% SDS and denatured salmon sperm DNA (100 µg/ml) for 16 hrs at 42° C. A random primed $^{32}$P-labeled fragment (1–2 10$^8$ dpm/µg) from the 1.6 kb BamHI-BglII fragment of RGB-2 which contains the coding region of this clone was used at $10^7$ dpm/ml in the hybridization solution from above to probe the filters overnight at 42° C. The blots were washed twice in 2×SSC and 0.1% SDS at 65° C. for 10 min. twice in 0.5×SSC and 0.1% SDS at RT for 15 min. and once in 0.1×SSC and 0.1% SDS at 65° C. for 15 min. Blots were exposed overnight at −70° C. to X-ray film with an intensifying screen.

The RGB-2 mRNA is expressed at different levels in various regions of the rat brain with the basal ganglia showing the highest concentration. Furthermore, the RGB-2 mRNA was found in high amounts in the neurointermediate lobe of the pituitary gland of the rat and to a lesser degree in the anterior lobe of this gland. The expression pattern of the RGB-2 mRNA is strikingly similar to the distribution of the $D_2$ dopamine receptor as determined by receptor autoradiography and binding studies of tissue preparations (19).

In order to study the pharmacological characteristics of the receptor encoded by RGB-2, the cDNA was expressed in eucaryotic cells. The full RGB-2 cDNA was cloned into the eucaryotic expression vector pZem3 (20) which initiates transcription from the mouse metallothionein promoter (21). This plasmid was cotransfected with the selectable neomycin phosphotransferase gene (pRSVneo) into the Ltk− mouse fibroblast cell line by the standard CaPO$_4$ precipitation technique (21). Cells were selected in 350 µg/ml of G418. Transfectants were isolated and checked for expression of RGB-2 mRNA by Northern blot analysis. A cell line expressing RGB-2 designated L-RGB2Zem-1 was isolated. The RGB-2 mRNA was not detectable in the parent Ltk- cell line.

Since the RGB-2 mRNA displayed the tissue distribution expected of the $D_2$ dopamine receptor, a pharmacological study was performed of the L-RGB2Zem-l cell line, native Ltk− cells and rat striatum using the $D_2$ ligand $^3$H-spiperone.

Membranes were prepared by homogenizing cells with a Dounce homogenizer at 4° C. in 0.25 M sucrose, 25 mM Tris pH 7.4, 6 mM MgCl$_2$, 1 mM EDTA. The homogenizing solution was centrifuged at 800×g for 10 min. and the pellet was subjected to a second homogenization and centrifugation as before. The supernatants were pooled and centrifuged at 200,000×g for 1 hour. The pellet of this centrifugation was resuspended in 25 mM Tris pH 7.4, 6 mM MgCl$_2$, 1 mM EDTA at approximately 250 µg protein/ml and stored in small aliquots at −70° C. Radioligand binding assays were carried out in duplicate in a volume of 2 ml (saturation analyses) or 1 ml (inhibition curves) containing (final concentration): 50 mM Tris, pH 7.4, 0.9% NaCl, 0.025% ascorbic acid, 0.001% bovine serum albumin, $^3$H-spiperone (Amersham, 95 Ci/mmol) and appropriate drugs. In some experiments 100 uM guanosine 5'-triphosphate was included. (+)-Butaclamol (2 uM) was used to define non-specific binding. Incubations were initiated by the addition of 15–40 µg of protein, carried out at 37° C. for 50 minutes, and stopped by the addition of 10 ml of ice-cold wash buffer (10 mM Tris, pH=7.4, and 0.9% NaCl) to each assay. The samples were filtered through glass-fiber filters (Schleicher and Schuell No. 30) and washed with an additional 10 ml of wash buffer. The radioactivity retained on the filter was counted using a Beckman LS 1701 scintillation counter. Data were analyzed as previously described (29) except that curves were drawn using the data analysis program Enzfitter. The resulting IC$_{50}$ values were converted to K$_i$ values by the method of Cheng and Prusoff (30).

Membranes prepared from control Ltk− cells showed no (+)-butaclamol- or sulpiride-displaceable binding of $^3$H-spiperone. Binding of $^3$H-spiperone to membranes prepared from L-RGB2Zem-1 cells was saturable with a Kd value of 48 pM (FIG. 4a). This value agrees with that observed for binding of $^3$H-spiperone to rat striatal membranes in parallel experiments (52 pM). In the experiment shown in FIG. 4a, Kd and Bmax values for membranes prepared from L-RGB2Zem-1 were 40 pm and 876 fmol/mg of protein, whereas the corresponding values in striatal membranes were 37 pm and 547 fmol/mg of protein. The density of binding sites as determined in four experiments was 945 fmol/mg of protein in L-RGB2Zem-1 membranes and 454 fmol/mg of protein in rat striatal membranes.

Figure 4B:
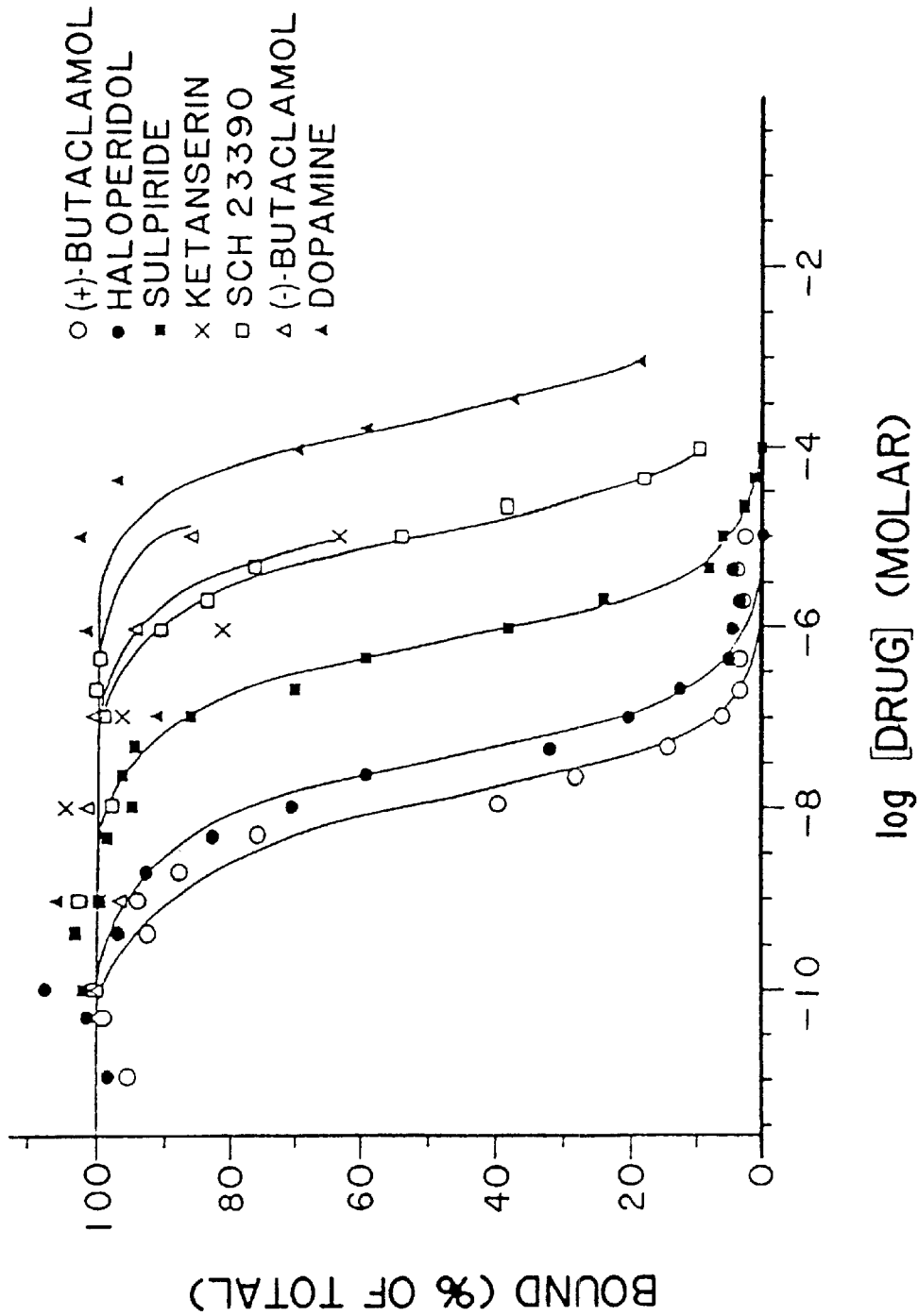
FIG. 4 illustrates the binding of $^3$H-spiperone to membranes from L-RGB2Zem-1 cells.

The binding of $^3$H-spiperone to membranes from L-RGB2Zem-1 cells was inhibited by a number of drugs and the resulting K$_i$ values closely matched those obtained using striatal membranes (FIGS. 4b, 4c). The $D_2$ antagonists (+)-butaclamol and haloperidol were the most potent inhibitors, followed by sulpiride. The $D_1$ dopamine antagonist SCH 23390 and the serotonin 5HT$_2$ antagonist ketanserin were much less potent at blocking $^3$H-spiperone binding. The binding appeared to be stereoselective as (+)-butaclamol was much more potent than (−)-butaclamol at inhibiting binding. In these experiments the absolute affinities of dopaminergic antagonists and the rank order of potency of the drugs (spiperone>(+)-butaclamol>haloperidol>sulpiride>>(−)-butaclamol) agree closely with previously published values for the $D_2$ dopamine receptor (2).

All binding data for L-RGB2Zem-1 membranes were fit best by assuming the presence of only one class of binding sites. On the other hand, inhibition by several drugs of $^3$H-spiperone binding to rat striatal membranes was fit best by assuming the presence of two classes of binding sites. Thus, SCH 23390 and ketanserin inhibited 10–20% of $^3$H-spiperone binding to rat striatal membranes with high affinity (FIG. 4c). In rat striatal membranes, inhibition of radioligand binding by sulpiride was fit best by one class of binding sites, but 10–15% of the (+)-butaclamol-displaceable binding was not inhibited by sulpiride at the concentrations used. It seems likely that the binding sites with high affinity for ketanserin and SCH 23390 and which are not displaced by sulpiride represent binding of $^3$H-spiperone to 5HT$_2$ serotonin receptors in rat striatal membranes. Binding of SCH 23390 to 5HT$_2$ receptors has been described previously (22). In rat striatal membranes, the apparent affinity of drugs for $D_2$ dopamine receptors, the class of binding sites comprising 80–90% of $^3$H-spiperone binding, was indistinguishable from the apparent affinity of drugs to membranes prepared from L-RGB2Zem-1 cells (FIG. 4c).

The physiological effects of stimulation of $D_2$ dopamine receptors appear to be mediated by $G_i$ (6). Inhibition of agonist binding to $D_2$ dopamine receptors by GTP is thought to be due to GTP-induced dissociation of a receptor-$G_i$ complex which has a high affinity for agonist (23,24). Although $^3$H-spiperone binding was inhibited by the agonist dopamine with a $K_i$ of 17 um in the L-RGB2Zem-1 membranes, this dopamine binding was not responsive to the addition of GTP. However, this finding is consistent with the reported lack of $G_i$ in L cells (25). The pharmacological data presented here proves that the binding profile of the $D_2$ dopamine receptor is found in Ltk- cells expressing the RGB-2 cDNA.

The foregoing data show that, when transfected into eucaryotic cells, the RGB-2 cDNA directs the expression of a $D_2$ dopamine binding protein. Since the mRNA corresponding to this cDNA is localized in tissues where the $D_2$ dopamine receptor is known to be present and since this mRNA codes for a protein which has all the expected characteristics of a G protein-coupled receptor, inter alia, RGB-2 is a clone for the rat $D_2$ dopamine receptor.

The nucleic acid sequence shown in FIG. 1 can be inserted into a wide variety of conventional and preferably commercially available plasmids, e.g., using EcoRI sites or other appropriate sites. See, e.g., FIG. 6 for a restriction map of the sequence of FIG. 1.

Dopamine receptor genes of this invention, particularly mammalian $D_2$ dopamine receptor genes, based on this disclosure, can now be routinely made, isolated and/or cloned, using many conventional techniques. For example, the procedure disclosed herein can be substahtially reproduced for libraries containing dopamine receptor DNA sequences. Alternatively, oligonucleotide probes can be routinely designed, e.g., from the sequences of FIG. 1 and/or the omitted introns, which are selective for dopamine receptor genes, especially for mammalian dopamine $D_2$ receptor genes. These can be used to screen nucleic acid libraries containing dopamine receptor nucleic acid sequences. Sequences in these libraries hybridizing to the probes, especially to all of a plurality of such probes (e.g. 2 or 3), will be DNA sequences of this invention with high probability. Of course, it is also possible to synthesize the sequence of FIG. 1 or any fragment thereof using conventional methods.

This invention also enables the production of a wide variety of useful products and the employment of a wide variety of useful methods, as well as providing basic tools for the study of the regulation and function of dopamine receptors.

These products and methods can be produced and carried out, respectively, using the well known recombinant DNA, immunochemical and other methodologies of the biotech industry. See, e.g., U.S. Pat No. 4,237,224; U.S. Pat. No. 4,264,731; U.S. Pat No. 4,273,875; U.S. Pat. No. 4,293,652; EP 093,619; Davis et al "A Manual for Genetic Engineering, Advanced Bacterial Genetics," Cold Spring Harbor Laboratory, Cold Spring Harbor, N.Y. (1980); Maniatis et al., *Molecular Cloning*, Cold Spring Harbor Laboratory, Cold Spring Harbor, N.Y.; Davis et al., *Basic Methods in Molecular Biology*, Elsevier, N.Y. (1986); *Methods in Enzymology*, Berger & Kimmel (Eds.), (1987).

This invention provides, for the first time, purified and isolated polypeptide products having all or part of the primary amino acid sequence of the dopamine $D_2$ receptor as well as its biological properties, including: all sites for covalent modification, such as phosphorylation and glycosylation; all primary sequence that determines the secondary, tertiary and quaternary structure of the functional protein; all parts of the molecule that provide antigenicity and antibody binding sites; all parts of the protein that provide for noncovalent interactions with other biological molecules, such as lipids, carbohydrates, and proteins, such as guanine nucleotide-binding regulatory proteins; all parts of the protein that make up the binding sites for ligands, including agonists, partial agonists and antagonists; all parts of the protein that are required for functional conformational changes involved in normal biological activities, such as desensitization; and all proteins that might arise as a result of alternative splicing of the gene for this receptor.

These polypeptides can be expressed from the nucleic acids of this invention by procaryotic or eucaryotic hosts, e.g., bacterial, yeast or mammalian cells in culture, using fully conventional transformation or transfection (e.g., via calcium phosphate for mammalian cells) techniques. The products of such expression in vertebrate (e.g., mammalian and avian) cells are especially advantageous in that they are produced free from association with other human proteins or contaminants with which they may be associated in natural form. Preferred hosts for expression are mammalian and include for example mouse Ltk$^-$ cells, hamster CHO cells, mouse $GH_4$ cells, mouse $C_6$ cells, mouse/rat NG108-15 cells and mouse AtT20 cells. For example, when the gene of FIG. 1 is transfected into the commercially available growth hormone $GH_4$ cells, modulation of the cAMP second messenger system has been observed. Preferred vectors include pzem or PRSV or viral vectors such as vaccinia virus and retroviruses.

The polypeptides of this invention include all possible variants, e.g., both the glycosylated and non-glycosylated forms. The particular carbohydrates involved will depend on the mammalian or other eucaryotic cells used for the expression. The polypeptides of the invention can also include an initial methionine amino acid residue.

Also included in this invention are polypeptides, synthetic or otherwise, duplicating the amino acid sequence of FIG. 1 and/or of the dopamine receptors per se of this invention, or only partially duplicating the same. These wholly or partially duplicative polypeptides will preferably also retain the biological and/or immunological activity of the dopamine receptor per se. Also included within the scope of this invention are the monoclonal and polyclonal antibodies (generatable by conventional techniques and preferably labelled) which are immunoreactive with such polypeptides.

Preferred partial polypeptides (fragments) are those including at least a portion of the sequences located in the hydrophobic transmembrane domains V, VI and VII, shown in FIG. 2. These are the likely locations of the ligand binding site(s), particularly domain VII. The third cytoplasmic loop is also an important fragment area; e.g., G-protein binding requires this location as well as domains V and VI. Where it is desired to have an antibody highly specific to a particular dopamine receptor, a fragment generating such an antibody will be selected from the highly unique region between transmembrane regions V and VI, i.e., the third cytoplasmic loop, or the C-terminal domain, both of which have low homology with other receptors, and/or the antibodies will be selected to be specific to an epitope in these regions. Another receptor/gene specific region is that of the intron sequences, e.g., those for RGB-2, mentioned above. Particularly preferred peptides which have been synthesized are (referring to the amino acid numbers of FIG. 1): (A) 2–13; (B) 182–192; (C) 264–277; (D) 287–298; and (E) 404–414. These are selected based on the following principles: the known antigenicity of peptides containing a large number of Pro residuds (B/C/D); coverage of the N and C termini (A) and (E); the ability to direct antibodies towards an extracellular domain (receptor reaction region) which will be effective to block the receptor reaction (A/C/D). Antibodies to these fragments are raised conventionally, e.g., monoclonals by fully conventional hybridoma techniques.

This invention also relates to DNA sequences encoding the full dopamine receptor or fragments thereof, as well as expression vectors (e.g., viral and circular plasmid vectors) containing such whole or partial sequences. Similarly, hosts (e.g., bacterial, yeast and mammalian) or cells transformed or transfected with such vectors are also included. The corresponding methods of expressing the polypeptides corresponding to the sequences in such vectors are also included, e.g., comprising culturing the transformed or transfected cells under appropriate conditions for large scale expression of the exogenous sequences and for the isolation of the polypeptides as usual, e.g., from the growth medium, cellular lysates or cellular membrane fractions.

DNA sequences of this invention also include those coding for polypeptide variants, mutants or analogues which differ from the natural sequence described herein. Such differences can be derived from deletion of one or more amino acid residues from the natural sequence, by substitution of a given such residue by another residue and/or by additions wherein one or more amino acid residues are added to the natural sequence. Preferably, the resultant modified polypeptide will retain at least one of the biological or immunological activities of the dopamine receptor.

Mutations likely to affect dopamine affinity activity will be those in transmembrane domains V, VI or VII or in the third cytoplasmic loop. In addition, the DNA sequences also include sequences complementary to any of the other DNA strands mentioned herein and, most notably, those shown in the Figures; DNA sequences which hybridize to the DNA sequences described herein, typically under the hybridization conditions mentioned herein or under more stringent conditions, or which hybridize to fragments of such DNA sequences; and DNA sequences which differ from those shown herein by the degeneracy of the genetic code. Thus, this invention includes all DNA sequences which encode a dopamine receptor and hybridize to one or more of the sequences shown herein. These include allelic variants as well as dopamine receptors from mammalian species other than the species mentioned in the experimental descriptions herein.

Modifications of the cDNA or genomic dopamine receptor DNA may be readily accomplished by any of the well known techniques, including site-directed mutagenesis techniques. Such modified DNA sequences can include deletions, additions and/or substitutions made in selected regions, e.g., not in transmembrane domains V, VI or VII or in the third cytoplasmic loop, where retention of the underlying biological activity of the dopamine receptor is desired.

Modified proteins which do not retain the mentioned biological activity and/or the corresponding DNA sequences will also be useful, e.g., in various assays of this invention. In a particularly preferred such modification, the transmembrane domain V, VI, or VII or the third cytoplasmic loop will be deleted or rendered inactive, e.g., by sequence modification. Deletion of the glycosylation sites shown in FIG. 1 is also a useful variant for expression of the polypeptide, e.g., in yeast cells.

As mentioned above, it is well established that significant portions of the DNA sequence encoding a dopamine receptor are conserved in various mammalian species. Consequently, using only routine experimentation, a skilled worker can readily screen a DNA genomic library or, preferably, a cDNA library, e.g., from the brain of a given mammal, for the presence of other dopamine receptor genes, especially $D_2$ dopamine receptor genes, using probes manufactured in accordance with the details of the sequences shown herein, including the 5' flanking, the intronic and the structural gene sequences shown in FIG. 1 and the human sequence of FIG. 7. Probes will preferably be selected from the seven highly conserved transmembrane domains shown in FIG. 2, preferably domains VI and VII. Such a routine screening will identify clones which hybridize with the probes.

From these, dopamine receptors can routinely be selected, e.g., using the techniques described herein. With respect to human $D_2$ dopamine receptors, particularly useful sources include, for cDNA, striatum, pituitary, neuroblastoma, kidney, placenta cells, etc., and, for genomic DNA, liver, placenta cells, etc. For primates, e.g., rhesus monkeys, particularly useful genomic DNA or cDNA libraries include brain, kidney and placenta cells.

With respect to human $D_2$ dopamine receptor genes, the partial sequence shown in FIG. 7 has been identified by conventionally screening, under the stringent hybridization conditions described above for the probing by the 0.8 kb EcoRI-PstI fragment of rat brain cDNA in $\lambda$gt10, a pituitary cDNA library using a probe which is the full length rat cDNA, RGB-2. The cDNA libraries mentioned herein were prepared by fully conventional methods, e.g., as described in the references cited above, e.g., Davis et al. This sequence or fragments thereof can also be useful as a probe, for example, to screen conventional libraries as mentioned above for human dopamine receptor genes in accordance with the foregoing and other fully conventional procedures. As can be seen by comparing the sequence of FIG. 7 with the sequences shown in FIGS. 1 and 2 above, the partial human sequence of FIG. 7 has high homology with RGB-2 beginning at amino acid no. 259 of FIG. 1.

Similarly, this invention more generally includes mammalian $D_2$ dopamine receptor genes in the broadest sense, e.g., both regulatory and structural such genes, alone or in combination, e.g., in reading frame. For example, using the routine methods discussed herein, such genes have been and can be cloned from mammalian DNA libraries. As well, this invention includes biologically active fragments of such genes, e.g., fragments encoding polypeptides having the biological activity of a mammalian $D_2$ dopamine receptor, or fragments useful in controlling expression of such encoding fragments, or fragments useful as probes for any such gene or fragment, e.g., by hybridizing therewith.

The various polypeptides and sequences of this invention may be conventionally labeled with detectable marker substances, typically by covalent association, and further typically by radiolabeling, or in the case of DNA, with non-isotopic labels such as biotin. The polypeptide products (e.g., labelled antibodies) can be used conventionally to detect and quantitate the presence of dopamine receptors in various samples; the DNA-labeled products can be conventionally employed in the usual hybridization methods (e.g., Northern blots, Southern blots, spot assays, etc.) to detect and quantitate the presence of associated nucleic acids (DNA, RNA) in samples, e.g., to locate the dopamine gene positions in various mammalian chromosomal maps, to determine whether mRNA or receptor concentrations are abnormally high or low in comparison to standard levels, etc. They will also be useful, again using fully conventional procedures, to identify dopamine receptor gene disorders (defective or aberrant genes) in in vitro diagnostic procedures on DNA samples from given patients, e.g., to detect chromosomal defects, e.g., using RFLP analyses (see, e.g., Genes III, Levin, John Wiley and Sons (1987). For example, since dopamine receptors have been implicated in schizophrenia, products and methods of this invention can be used to characterize nucleic acids, e.g., In size fractionated form, from schizophrenia patients and, inter alia, classify patients according to schizophrenia subgroups, make diagnoses based on comparisons to standard DNA fractionation arrays, etc. Of course, they can also be used, e.g., in the mapping of the human or other mammalian genome, as gene markers to identify accompanying genes, e.g., in RFLP analyses, and, where applicable, other disorders. The gene-unique regions discussed above, e.g., the intron regions, the third cytoplasmic loop, etc., will be especially useful in this regard.

Typical assays in which the polypeptides of this invention can be utilized include any of the well known immunoassay techniques such as RIA, ELISA, etc., both of in vitro and in vivo nature. Various fragments of the polypeptide sequence of the dopamine receptor can also be utilized conventionally for producing corresponding polyclonal antibodies or preferably monoclonal antibodies (e.g., by conventional preparation and expression of corresponding hybridomas) for epitopes within the given fragment. The antibodies will often be conventionally labelled, e.g., radio- or enzymatically labelled. In a preferred aspect, the resultant polyclonal or monoclonal antibodies will also be immunospecific with respect to not only the mentioned fragment, but also the full protein. Such antibodies will be conventionally employable, for example, in the detection and affinity purification or chromatography of dopamine receptor and related products.

Of course, the polypeptides of this invention include those expressed in accordance with conventional procedures from cells as mentioned above, as well as those which are synthetically prepared also using conventional procedures. This invention enables for the first time non-natural preparation of mammalian dopamine receptors substantially free of constituents of their natural environment. It is in this sense the term "substantially pure" is used herein, i.e., substantially free of these natural constituents. The invention also incaudes DNA sequences which can be isolated from the various sources mentioned above or synthetically prepared using fully conventional methods.

Also included within the scope of this invention are pharmaceutical compositions comprising effective amounts of one or more of the polypeptide products of this invention or one or more of the nucleic acid sequences of this invention, in admixture with suitable conventional diluents, adjuvants and/or carriers well known in the pharmaceutical industry. These can be utilized for in vitro uses, e.g., for detection of the presence of a dopamine receptor in a sample or of the presence of a gene or an abnormal gene in a sample or for increasing the concentration of receptor or its gene in a sample, or for in vivo uses such as gene therapy (e.g., to render a defective gene or gene product inactive, e.g., block it by an appropriate monoclonal antibody) and/or to provide new functional genes (e.g., using retroviral vectors)), or to provide an increased concentration of dopamine receptor in a given location, or to modulate receptor expression and/or activity, e.g., by administration of antisense oligosequences, all in mammals including humans. Thus, these compositions will be useful to treat disease conditions, inter alia, those associated with abnormalities in the structure, expression or concentration of the dopamine receptor or its gene, such as those mentioned in the foregoing. Specific effective dosages for a given condition in a given patient will vary, as is well known, with the usual conditions, including the overall condition of the patient, body weight, the identity and severity of the particular dopamine-deficiency disease state, etc.

The polypeptides of this invention can also be used in, e.g., competitive binding assays, to test for the affinity thereto of candidate chemical substances such as drugs, e.g., affinity (e.g., agonistic or antagonistic) to $D_2$ dopamine receptors. Such procedures can be carried out, e.g., as pharmaceutical screening tests, using fully conventional procedures, analogous to those described herein and/or to known protocols based on natural sources of dopamine receptors, e.g., analogous to known tests for inhibition of the binding of tritiated dopamine agonists and antagonists to striatal receptors per the methods of Schwarcz et al., J. Neurochemistry, 34 (1980), 772–778 and Creese et al., European J. Pharmacol., 46 (1977), 377–381, and to those for other receptors. It is also possible to screen substances for ability to modify or initiate a response which is triggered by ligand bonding to a dopamine receptor, e.g., cellular responses such as modulation of second messenger systems. Such analyses can utilize cells of this invention transformed with nucleic acid sequences of this invention.

Antibodies of this invention to the dopamine receptors or other regions of dopamine receptor genes, especially the $D_2$ receptor, can also be used in diagnostic imaging techniques, e.g., by radiodiagnostic, MRI or positron imaging. Radio-, paramagnetic- or positron-labels can be conventionally attached to the antibodies (preferably monoclonal in nature), e.g., via covalent bonding to chelating groups for a positron emitting, radionucleotide or paramagnetic metal. MRI, radiosensitive or positron imaging can then be effected with these agents using conventional methods. See, e.g., Maziere et al., Life Sci., 35, 1349 (1984).

Suitable pharmaceutical carriers include water, saline, human serum albumin, etc. The compositions can also include other active ingredients suitable for amelioration of the particular disease state involved, e.g., conventional dopamine agonists, dopamine antagonists, etc. The components of this invention can be provided in conventional kit form containing, e.g., an antibody or a DNA probe (e.g., able to detect gene homologies or anomalies) along with detection method-specific reagents such as enzymes, substrates, materials for analyzing DNA restriction fragments, etc.

The DNA sequences of this invention are also useful to prepare the corresponding transgenic animals, in particular nonhuman mammals, e.g., rats, monkeys, etc., using known methods, e.g., analogous to those described in U.S. Pat. No. 4,736,866. Such animals, e.g., are particularly useful for commercial research purposes. The DNA sequences or the corresponding mRNA can also be used conventionally to inject oocytes, e.g., from frogs, which can then be conventionally used in binding or second messenger analyses. Moreover, the availability of the primary amino acid sequence itself enables experimental and computational modeling and understanding of the secondary and tertiary structures of the dopamine receptor. This three-dimensional information provides a basis for modeling and understanding the details of the receptor function, e.g., interaction with the cell membrane, its ligand (binding pocket), associated proteins, messenger systems, etc. Such analyses enable rational drug design whereby, e.g., new dopamine receptor affecting chemical agents can be designed in accordance with the details of this interaction.

NUMBERED REFERENCES FOR BACKGRUOND, SUMMARY, FIGS. 1–7, AND DISCUSSION (Excluding Examples)

1. Creese, I., Sibley, D. R., Hamblin, M. W. & Leff, S. E. *Ann. Rev. Neurosci.* 6, 43–71 (1983).
2. Seeman, P. *Pharmacol. Rev.* 32, 229–313 (1980).
3. Lee, T. et al. *Nature* 273, 59–61 (1984).
4. Seeman, P. et al. *Science* 225, 728–731 (1984).
5. Barnes, D. M. Science 241, 415=417 (1988).
6. Cote, T. E., Frey, E. A., Grewe, C. W., & Kebabian, J. W. *J. Neural. Trans. Suppl.* 18, 139–147 (1983).
7. Senogles, S. E. et al. *J. Biol. Chem.* 262, 4860–4867 (1987).
8. Dohlman, H. G., Caron, M. G. & Lefkowitz, R. J. *Biochemistry* 26, 2657–2664 (1987).
9. Dixon, R. A. F., et al. *Nature* 321, 75–79 (1986).
10. Mount, S. M. *Nucleic Acids Res.* 10, 459–472 (1982).
11. Grigoriadis, D. E., Niznik, H. B., Jarvie, K. R. & Seeman, P. *FEBS Let.* 227, 220–224 (1988).
12. Kobilka, B. K., et al. *Science* 238, 650–656 (1987).
13. Kobilka, B. K., et al. *Nature* 329, 75–79 (1987).
14. Kubo, T., et al. *Nature* 323, 411–416 (1986).
15. Kubo, Y., et al. *Nature* 329, 836–838 (1986).
16. Strader, C. D., et al. *J. Biol. Chem.* 263, 10267–10271 (1988).
17. Sibley, D. R., Benovic, J. L., Caron, M. G. & Lefkowitz, R. J. *Cell* 48, 913–922 (1987).
18. Bouvier, M., et al. *Nature* 333, 370–373 (1988).
19. Boyson, S. J., McGonigle, P. & Molinoff, P. B. *J. Neurosci.* 6, 3177–3188 (1986).
20. Uhler, M. & McKnight, G. S. *J. Biol. Chem.* 262, 15202–15207 (1987).
21. Gorman, C., Padmanabhan, R. & Howard, B. H. *Science* 221, 551–553 (1983).
22. Hyttel, J. *Eur. J. Pharmacol.* 91, 153–154 (1983).
23. Hamblin, M. W., Leff, S. E. & Creese, I. *Biochem. Pharmacol.* 33, 872–877 (1984).
24. Dolphin, A. C. *Trends in Neurosci.* 10, 53–57 (1987).
25. Jones, S. V. P., et al. *Proc. Nat. Acad. Sci. U.S.A.* 85, 4056–4060 (1988).
26. Sanger, F., Nicklen, S. & Coulson, A. R. *Proc. Nat. Acad. Sci. U.S.A.* 74, 5463–5467 (1977).
27. Chirgwin, J. M., Przybyla, A. E., McDonald, R. J. & Rutter, W. J. *Biochemistry* 18, 5294–5299 (1979).
28. Ullrich, A., et al. *Science* 196, 1313–1319 (1977).
29. Neve, K. A. & Molinoff, P. B. *Mol. Pharmacol.* 30, 104–111 (1986).
30. Cheng, Y. C. & Prusoff, W. H. *Biochem. Pharmacol.* 22, 3099–3108 (1973).

Without further elaboration, it is believed that one skilled in the art can, using the preceding description, utilize the present invention to its fullest extent. The mentioned embodiments are, therefore, to be construed as merely illustrative and not limitative of the remainder of the disclosure in any way whatsoever.

From the foregoing description, one skilled in the art can easily ascertain the essential characteristics of this invention and, without departing from the spirit and scope thereof, can make various changes and modifications of the invention to adapt it to various usages and conditions.

The entire texts of all applications, patents and publications cited above are hereby incorporated by reference.

EXAMPLES

Example 1

Summary

We recently cloned a complementary DNA for the rat dopamine D-2 receptor, making it possible to create cell lines expressing this receptor. A cell line (LZR1) was created by transfecting the D-2 cDNA (RGB-2) into mouse fibroblast Ltk⁻ cells. LZR1 cells, previously described as L-RGB2Zem-1 cells (1), expressed a high density of D-2 receptors, whereas the wild-type cells did not. Although transcription of the RGB-2 cDNA is regulated by the zinc-inducible mouse metallothionein promoter, the density of D-2 receptors on membranes prepared from LZR1 cells was not increased after the cells were treated with zinc. A second cell line derived from Ltk⁻ cells, designated LZR2, had a lower density of D-2 receptors in the uninduced state, and treatment with zinc induced a 50% increase in the receptor density. A number of agonists competitively and stereoselectively inhibited the binding of [$^3$H]spiroperidol to the expressed D-2 receptors. In LZR1 cells, dopamine was a more potent inhibitor of radioligand binding in the absence than in the presence of GTP and NaCl. Dopamine reduced forskolin-stimulated adenylate cyclase activity by 27% in membranes prepared from LZR1 cells. Inhibition by dopamine was blocked by (+)-butaclamol or prior treatment of intact cells with pertussis toxin. These data indicate that the RGB-2 cDNA directs the expression of a dopamine D-2 receptor capable of interacting with guanine nucleotide-binding proteins and inhibiting adenylate cyclase activity. Furthermore, the RGB-2 cDNA provides a means of creating many cell lines that will be useful tools for the biochemical and pharmacological characterization of dopamine D-2 receptors.

Introduction

Dopamine (DA) receptors have been classified into two subtypes based on functional and pharmacological profiles (2). DA D-2 receptors are characterized functionally by their ability to inhibit adenylate cyclase activity (3). Activation of D-2 receptors also inhibits calcium channels (4,5), increases potassium conductance (6), and may inhibit accumulation of inositol phosphates (7,8). One factor that has impeded research on the regulation and functional characteristics of DA receptors has been the lack of cell lines that express the receptors. One cell line, derived from a prolactin-secreting tumor, has recently been described in which DA inhibits adenylate cyclase activity and prolactin secretion (9).

We recently cloned a rat brain complementary DNA (cDNA), designated RGB-2, that has significant homology with $\beta_2$-adrenergic receptors and other receptors that interact with guanine nucleotide-binding proteins. Three lines of evidence indicate that the RGB-2 cDNA encodes the DA D-2 receptor: (1) The deduced amino acid-sequence of the protein suggests the existence of the seven membrane-spanning domains typical of receptors coupled to guanine nucleotide-binding proteins (10); (2) the distribution of messenger RNA that hybridizes with the cDNA parallels the distribution of the D-2 receptor; and (3) when the RGB-2 cDNA is transfected into cells that lack high affinity binding of the D-2 selective ligand [$^3$H]spiroperidol, the cells express binding sites for the radioligand with a pharmacological profile characteristic of D-2 receptors (1).

The cloning of a D-2 receptor cDNA makes it possible to express DA receptors in cell lines in which the effects of receptor activation can readily be determined. We previously described the binding of [$^3$H]spiroperidol and other D-2 antagonists to a line of cells derived by transfection of mouse L cells with the RGB-2 cDNA under the control of a zinc-inducible mouse metallothionein promoter (1). We also reported that, under the assay conditions used previously, the binding of DA to LZR1 membranes was not responsive to GTP. We now demonstrate that the D-2 receptor encoded by the RGB-2 cDNA is functional with respect to the guanine nucleotide sensitivity of the binding of agonists and the ability of agonists to inhibit adenylate cyclase activity.

Methods

Materials: [$\alpha$-$^{32}$P]Adenosine 5'-triphosphate (ATP, 10–50 Ci/mmol) and [$^3$H]cyclic AMP (31.9 Ci/mmol) were purchased from New England Nuclear (Boston, Mass.), and [$^3$H]spiroperidol (95 Ci/mmol) was purchased from Amersham (Arlingtton Heights, Ill.). Guanosine 5'-triphosphate (GTP), DA, cyclic AMP, 3-isobutyl-1-methyl-xanthine, ATP, and forskolin were purchased from Sigma Chemical Company (St. Louis, Mo.). Quinpirole, LY181990 (Lilly Laboratories), bromocriptine (Sandoz Research Institute), and (+) and (−)3-PPP (Astra) were generous donations.

Transfection: The full RGB-2 cDNA was cloned into the plasmid pzem3 (11). The cDNA and the vector were made compatible by partially filling in the BglII site on the vector and a SalI site on the cDNA adaptor. This plasmid was co-transfected with the plasmid pRSVneo into mouse Ltk$^-$ cells by a CaPO$_4$ precipitation technique (12). Transfectants were selected in 350 $\mu$g/ml of G418, isolated, and screened for expression of RGB-2 mRNA by Northern blot analysis. The subclone LZR1, selected on the basis of high expression of RGB-2 mRNA, was partially characterized previously as L-RGB2Zem-1 (1). A second cell line, LZR2, was isolated in the same way.

Tissue culture: Cells were plated at a density of 20,000 cells/cm$^2$ in 150 mm diameter Falcon tissue culture plates (Beckton Dickinson, Lincoln Park, N.J.), subcultured by replacing the growth medium with trypsin-EDTA (0.1% trypsin, 0.02% EDTA in phosphate-buffered saline) or fed on day 3, and harvested on day 5 or 6. Cells were grown in Dulbecco's modified Eagles' medium (Sigma), supplemented with 5% fetal bovine serum and 5% iron-supplemented calf bovine serum (Hyclone, Logan, UT), in an atmosphere of 10% CO$_2$/90% air at 37°. Cells were lysed by replacing the growth medium with ice-cold hypotonic buffer (1 mM Na$^+$-HEPES, pH 7.4, 2 mM EDTA). After swelling for 10–15 min, the cells were scraped from the plate and centrifuged at 24.000×g for 20 min. The resulting crude membrane fraction was resuspended with a Brinkmann Polytron homogenizer at setting 6 for 10 sec in Tris-isosaline (50 mM Tris-HCl, pH 7.4, and 0.9% NaCl) and stored at −70° for receptor binding experiments or resuspended in Tris-isosaline, centrifuged again at 24,000×g for 20 min., and resuspended in Tris-isosaline for immediate use in adenylate cyclase experiments.

Receptor binding assay: The membrane preparation was thawed, centrifuged at 24,000×g for 20 min., and resuspended in Tris-isosaline except where indicated. Aliquots of the membrane preparation were added to assay tubes containing (final concentrations) 50 mM Tris-HCl, pH 7.4, 0.9% NaCl, 0.025% ascorbic acid, 0.001% bovine serum albumin, [$^3$H]spiroperidol, and appropriate drugs. (+)-Butaclamol (2 $\mu$M) was used to define nonspecific binding, which was typically less than 10% of total binding at concentrations of radioligand near the K$_D$ value. Assays were carried out in duplicate in a volume of 2 ml for saturation analyses or 1 ml for inhibition analyses. Incubations were initiated by the addition of 15–50 $\mu$g of protein, carried out at 37° for 50 min., and stopped by the addition of 10 ml of ice-cold wash buffer (10 mM Tris, pH 7.4, and 0.9% NaCl) to each assay. The samples were filtered through glass-fibre filters (Schleicher & Schuell No. 30) and washed with an additional 10 ml of wash buffer. The radioactivity retained on the filters was counted using a Beckman LS 1701 scintillation counter. Data were analyzed by nonlinear regression using the data analysis program Enzfitter (Elsevier-Biosoft). In competition experiments, K$_I$ values were calculated from experimentally determined IC$_{50}$ values by the method of Cheng and Prusoff (13). Averages for K$_I$ and K$_D$ values are the geometric means. In experiments designed to assess the effect of GTP and NaCl on the binding of DA, fresh tissue was used. Cells were harvested, centrifuged, and Mg$^{2+}$ resuspended in Tris-Mg$^{2+}$ (50 mM Tris, pH 7.4, and 4 mM MgCl$_2$). Tissue was incubated for 15 min. at 37° in this buffer before re-centrifugation. The resuspended protein was added to assays containing Tris-Mg$^{2+}$ with no added NaCl or GTP, or Tris-Mg $^{2+}$ with 120 mM NaCl and 100 $\mu$M GTP.

Adenylate cyclase assay: The conversion of [$\alpha^{32}$P]ATP to [$^{32}$P]cAMP was determined essentially as described by Salomon et al. (14). Membranes (50–100 $\mu$g of protein) resuspended in Tris-isosaline were added in a volume of 0.1 ml to an assay of 0.2 ml containing 50 mM Tris-HCl, pH 7.4, 5 mM cAMP, 1 mM 3-isobutyl-1-methylxanthine 1 mM MgCl$_2$, 0.5 mM EGTA, 0.25 mM ATP, 30 $\mu$M GTP, approximately 2×10$^6$ cpm of [$\alpha$-$^{32}$P]ATP, and various drugs. Assays were initiated by warming to 25° and terminated after 20 minutes by cooling to 0°, then adding trichloroacetic acid (100 $\mu$l of a 30% solution) to each assay. [$^3$H]Cyclic AMP (approximately 30,000 cpm) was added to each assay as an internal standard. The assay volume was brought up to 1 ml with water, and tubes were centrifuged for 10 min. at 2000×g. Cyclic AMP in the supernatant was isolated by sequential chromatography on columns containing Dowex AG50W-X4 resin and neutral alumina. The 2-ml eluate from each column of alumina was dissolved in 10 ml of Bio-Safe II (RPI, Mount Prospect, Ill.) for liquid scintillation counting. Dose-response curves for inhibition of adenylate cyclase activity by agonists were analyzed by nonlinear regression using the program Enzfitter. The data were fit to the equation:

$$E=(100-E_{max})/(1+(A/EC_{50})^N)+E_{max}$$

where E is the amount of enzyme activity, expressed as percentage of total stimulated activity, A is the concentration of agonists, EC$_{50}$ is the concentration of agonist causing half-maximal inhibition of enzyme activity, E$_{max}$ is the enzyme activity observed in the presence of maximally inhibiting concentrations of agonist, expressed as the percentage of total stimulated activity, and N is a slope factor. Averages of EC$_{50}$ values are the geometric means. Protein concentration was determined by the method of Peterson (15).

Results

Saturation analysis of the binding of [$^3$H]spiroperidol: The density of D-2 receptors on membranes prepared from LZR1 cells was determined by saturation analysis of the binding of [$^3$H]spiroperidol (FIG. 8). Since the RGB-2 cDNA is under the control of the zinc-inducible mouse metallothionein promoter, the effect of prior treatment of cells with 100 μM zinc sulfate on the binding of [$^3$H]spiroperidol was also determined. The density of binding sites was 736±140 fmol/mg of protein in control LZR1 cells, and 759±155 fmol/mg of protein in LZR1 cells treated with zinc (n=2). A second cell line, designated LZR2, had a lower density of D-2 receptors (mean $B_{max}$±SE, 435±71 fmol/mg of protein). In contrast to LZR1 cells, the density of binding sites on LZR2 cells was increased 50% by zinc treatment to 630±52 fmol/mg of protein. The mean $K_D$ value of 42 pM for control LZR1 and LZR2 cells ($pK_D$±SE, 10.37±0.15, n=4) did not differ significantly from the mean $K_D$ value of 47 pM for zinc-treated cells (10.33±0.17). Scatchard transformation of saturation analyses from all experiments yielded straight lines. Wild-type Ltk$^-$ cells had no detectable displaceable binding of [$^3$H]spiroperidol (data not shown). Since LZR1 cells had the higher density of D-2 receptors, these cells were used in all subsequent experiments.

Figure 9A:
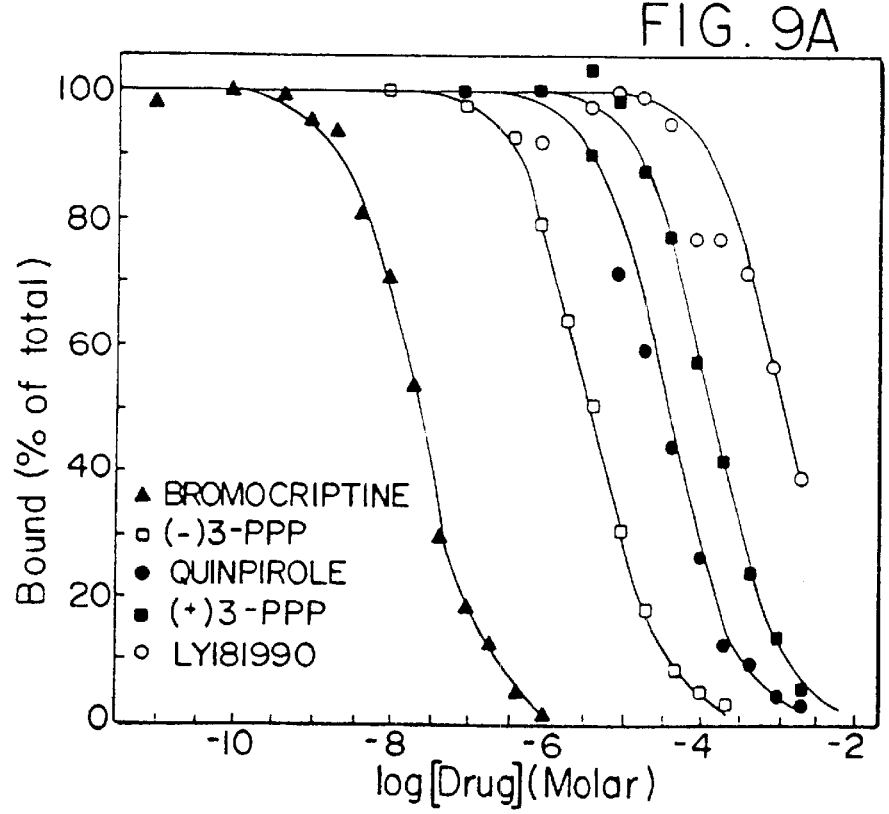

Inhibition of radioligand binding by agonists: The apparent affinity of D-2 receptors for several agonists and related compounds was determined in two experiments (FIG. 9A, Table 1). Of the six compounds tested, bromocriptine was the most potent with a mean $K_I$ value of 2 nM, whereas LY181990, the inactive enantiomer of the D-2-selective agonist quinpirole, was the least potent. All assays were carried out in the presence of 0.1 mM GTP and 120 mM NaCl, using membranes prepared from LZR1 cells.

Figure 9B:
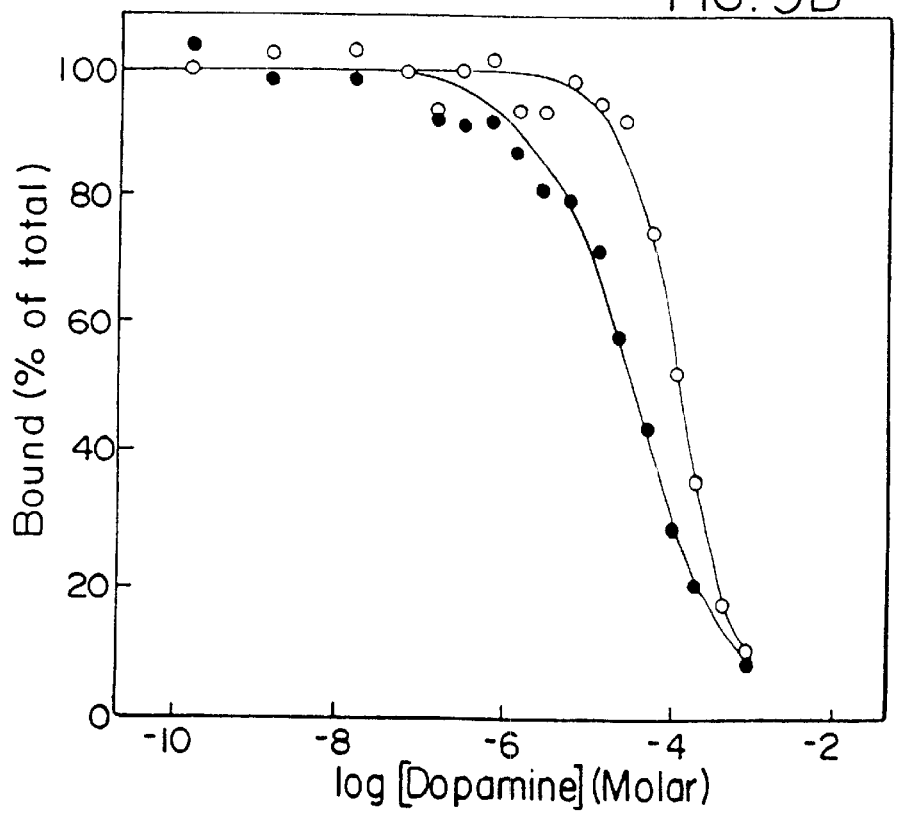

In other experiments, the effect of GTP and NaCl on inhibition of radioligand binding by DA was determined (FIG. 9B). Freshly prepared membranes were used for these experiments, and 4 mM MgCl$_2$ was added to the homogenization and assay buffers. In the absence of GTP and NaCl, the mean IC$_{50}$ was 25 μM [mean—log(IC$_{50}$)±SE=4.6±0.3]. Addition of GTP and NaCl to the assay buffer increased the mean IC$_{50}$ value to 167 μM (3.8±0.3, n=4), without altering the binding of [$^3$H]spiroperidol. Hill coefficients in the absence of GTP and NaCl ranged from 0.56 to 0.68 (mean=0.64) whereas in the presence of GTP and NaCl values ranged from 0.77 to 1.1 (mean=0.94). In the absence of GTP and NaCl, inhibition curves for DA could be fit best by assuming the presence of two classes of binding sites. One class of high affinity sites, representing 48±14% of the total number of receptors, had a mean $K_I$ for DA of 0.3 μM. The second class, representing 52±13% of the total number of receptors had a mean $K_I$ value of 24 μM.

Inhibition of adenylate cyclase activity by agonists: In freshly prepared membranes from LZR1 cells, but not in membranes from wild-type Ltk$^-$ cells, DA caused a concentration-dependent attenuation of forskolin-stimulated adenylate cyclase activity. Maximal inhibition was 27% of total activity, with an EC$_{50}$ value of 624 nM (FIG. 10A; Table 1). Quinpirole was approximately as efficacious as dopamine; that is, the maximal inhibition induced by quinpirole was similar to that induced by DA. LY181990 was less potent and less efficacious than its active isomer (FIG. 10B; Table 1), indicating that D-2 receptor-mediated inhibition of adenylate cyclase activity was stereoselective. The finding that LY181990 caused measurable inhibition of enzyme activity in only 2 out of 3 experiments (Table 1) suggests that the compound has little or no agonist activity. Similarly, (−)3-PPP did not have detectable agonist activity. Bromocriptine, with an EC$_{50}$ value of 45 nM, was the most potent agonist. Bromocriptine and (+)3-PPP were less efficacious than DA; thus, the drugs appeared to be partial agonists.

Inhibition of adenylate cyclase activity in LZR1 cells by 10 μM DA was prevented by including 10 μM (+)-butaclamol in the assay (FIG. 11), indicating that inhibition of DA is receptor-mediated. Also, treatment of LZR1 cells with pertussis toxin (50 ng/ml of growth medium for 16 hours) blocked DA-inhibited enzyme activity in membranes prepared from the cells (FIG. 10C), suggesting that $G_i$ mediates inhibition of enzyme activity by DA. Interestingly, forskolin-stimulated adenylate cyclase activity in membranes from pertussis toxin-treated cells was approximately 2.5-fold greater than activity in control membranes.

TABLE 1

Inhibition of Radioligand Binding and Adenylate Cyclase Activity by Agonists

The apparent affinity ($K_I$) of 6 drugs for D-2 receptors on membranes prepared from LZR1 cells, determined by inhibition of the binding of [$^3$H]spiroperidol (0.2 nM), is shown, as well as the concentration of each drug that caused half-maximal inhibition of forskolin-stimulated adenylate cyclase activity (EC$_{50}$). Values for drug concentrations, expressed as μM, are the geometric means of results from 3 experiments (EC$_{50}$, quinpirole and (+)3-PPP), 4 experiments (EC$_{50}$-DA) or 2 ($K_I$, all drugs; EC$_{50}$, bromocriptine) experiments. The maximal inhibition of adenylate cyclase activity observed (Max) is expressed as the mean±SEM of the percent inhibition of total activity in the presence of 10 μM forskolin. For LY181990, the results shown are from two experiments in which inhibition of enzyme was observed. There was no inhibition in a third experiment.

| Drug | $K_I$ | EC$_{50}$ | Max |
|---|---|---|---|
| Dopamine | 17 | 0.6 | 27 ± 3% |
| Quinpirole | 9 | 0.7 | 28 ± 2% |
| LY181990 | 277 | 5.0 | 10 ± 2% |
| Bromocriptine | 0.0024 | 0.04 | 17 ± 1% |
| (+)3-PPP | 33 | 4.0 | 16 ± 3% |
| (−)3-PPP | 0.87 | — | — |

Discussion

As reported previously, Ltk$^-$ cells transfected with a rat D-2 receptor cDNA express a high density of DA D-2 receptors (1). We have characterized one subclone of these cells, designated LZR1, that stably expresses D-2 receptors at a density of 750 to 1000 fmol/mg of protein (present results; ref. 1).

As the D-2 cDNA is contained in the plasmid pZem3, under the regulation of a zinc-inducible promoter, the effect of zinc treatment on the properties of radioligand binding was determined. D-2 receptors on LZR1 cells appear to be maximally expressed in the absence of zinc, so that zinc treatment caused no increase in the density of receptors. The lack of responsiveness to zinc is not a characteristic of the LtK$^-$ cell line, since we have isolated a second transfected line of Ltk$^-$ cells, LZR2, in which the density of D-2 receptors is elevated approximately 50% by treatment with zinc, from 435 to 630 fmol/mg of protein. The affinity of D-2 receptors for [$^3$H]spiroperidol was not significantly altered by zinc treatment.

The apparent affinity of D-2 receptors on LZR1 cells for several agonists and related drugs was determined by inhibiting the specific binding of [$^3$H]spiroperidol with the drugs in the presence of GTP. Bromocriptine was an extremely potent agonist, with a $K_I$ value of 2 nM. The potency of quinpirole, like that of DA, was approximately 10 μM. The binding of agonists was stereoselective, since LY181990 was much less potent than its active enantiomer, quinpirole, and (−)3-PPP was more potent than (+)3-PPP. These data extend our previous investigation of the binding of antagonists to D-2 receptors on LZR1 cells (1).

Physiological effects of stimulation of D-2 receptors appear to be mediated by a guanine nucleotide-binding protein, $G_i$, that inhibits adenylate cyclase activity (16). High affinity binding of agonists is thought to represent a ternary complex composed of agonist, receptor, and the α-subunit of $G_I$ ($G_{i\alpha}$), and inhibition of agonist binding to D-2 receptors by GTP represents GTP-induced uncoupling of D-2 receptors from $G_{i\alpha}$. To evaluate the ability of D-2 receptors encoded by the RGB-2 cDNA to couple to G proteins, the effect of GTP on the potency of DA for inhibition of radioligand binding was determined. In preliminary studies using LZR1 cells, we found that in our standard assay buffer containing 120 EM NaCl and no added $Mg^{2+}$, the binding of DA was not sensitive to GTP (1), although under the same conditions the binding of DA to rat striatal membranes is inhibited by GTP (data not shown). There were three possible explanations for the lack of sensitivity to GTP in LZR1 membranes: (1) LZR1 cells, derived from Ltk⁻ cells, could lack the appropriate G-protein. (2) The RGB-2 cDNA could encode only a binding subunit of the D-2 receptor. This possibility seemed unlikely because of the similarity between the predicted primary structure of the protein encoded by RGB-2 and other receptors coupled to guanine nucleotide-binding proteins. (3) It could be that the ionic conditions of the binding assay were not appropriate for formation or destabilization of the ternary complex. In the studies described here, ionic conditions were varied to increase the likelihood of observing GTP-sensitive binding. To maximize high-affinity agonist binding, tissue was preincubated with $MgCl_2$, and $MgCl_2$ was included in the assay buffer (17). To maximize GTP-induced destabilization of the ternary complex, NaCl was added together with GTP (17). Under these conditions, addition of GTP and NaCl decreased the potency of DA for D-2 receptors and increased the slope of the inhibition curve in membranes from LZR1 cells. It is interesting that the ionic requirements for formation and destabilization of the ternary complex seem to be more stringent in membranes from LZR cells than in membranes from rat striatum.

Inhibition of adenylate cyclase activity by DA D-2 receptors is a well-characterized phenomenon (3, 18, 19). Inhibition of adenylate cyclase activity by several drugs was assessed in membranes from LZR1 cells. Maximally effective concentrations of DA and the D-2-selective agonist quinpirole decreased forskolin-stimulated enzyme activity by almost 30%. Inhibition of enzyme activity by DA was blocked by the D-2 antagonist (+)-butaclamol. The most potent agonist tested, bromocriptine, appeared to be a partial agonist, as reported by others (19, 20). Inhibition of adenylate cyclase by agonists was stereoselective, since LY181990, the dextrorotatory enantiomer of quinpirole, had little or no efficacy. As has been reported previously, the partial agonist (+)3-PPP is a stronger agonist than (−)3-PPP, although (−)3-PPP binds to D-2 receptors with higher affinity (21, 22). We observed no inhibition of adenylate cyclase activity by (−)3-PPP in membranes from LZR1 cells. The $EC_{50}$ values determined for inhibition of adenylate cyclase activity by agonists were generally lower than the $K_I$ values determined in assays of ligand binding (Table 1). This could be due to the presence of a receptor reserve on these cells, although the observation that drugs differed in maximal inhibition of enzyme activity suggests that there is not a large receptor reserve even for the most efficacious agonists, DA and quinpirole. Also, there would be no receptor reserve for a partial agonist such as (+)3-PPP. An alternative explanation is that inhibition of adenylate cyclase activity could be related to the binding of agonists to D-2 receptors in a high-affinity state induced by formation of the ternary complex, as had been proposed for inhibition of enzyme activity by DA in the anterior pituitary (23). On the other hand, $K_I$ values in the present report, determined in the presence of GTP and NaCl, reflect the binding of agonists to receptors in a state of low affinity. Direct comparisons are difficult, since adenylate cyclase and radioligand binding assays were carried out at different temperatures, but the $K_I$ value for DA binding to the high-affinity class of sites (0.3 $\mu M$) is close to the $EC_{50}$ value for DA-inhibited adenylate cyclase (0.6 $\mu M$), whereas the $K_I$ values for the binding of DA to the low-affinity class of sites (24 $\mu M$) and binding in the presence of GTP (17 $\mu M$) are considerably higher.

DA did not inhibit adenylate cyclase activity in membranes from LZR1 cells that had been treated with pertussis toxin. Since pertussis toxin-catalyzed ADP-ribosylation of $G_i$ prevents $G_i$-mediated inhibition of adenylate cyclase, this finding is consistent with the hypothesis that D-2 receptors interact with $G_{i\alpha}$ in the transfected LZR1 cells. As has been observed for stimulation of adenylate cyclase activity by isoproterenol after pertussis toxin-treatment of other cell types (24), treatment of intact LZR1 cells with pertussis toxin potentiated the ability of forskolin to stimulate adenylate cyclase activity, suggesting that in some cell lines $G_1$ normally acts to attenuate forskolin- and hormone-stimulated adenylate cyclase activity.

We have characterized a cell line, transfected with the RGB-2 cDNA, that stably expresses a high density of D-2 receptors. With this cell line, it was determined the cDNA encodes a DA D-2 receptor that interacts productively with a guanine nucleotide-binding protein to inhibit adenylate cyclase activity. It seems likely that the RGB-2 cDNA would direct the expression of a functional D-2 receptor in almost any type of cell. For example, $GH_4C_1$ cells, derived from a rat pituitary tumor (25), are prolactin-secreting cells that lack DA receptors, even though lactrotrophs in the rat anterior pituitary express D-2 receptors. Transfection of the RGB-2cDNA into $GH_4C_1$ cells results in the expression of a D-2 receptor with functional characteristics similar to those described here (26). Cell lines created by transfection with a D-2 receptor cDNA will be useful in the study of mechanisms of action and regulation of D-2 receptors.

REFERENCES FOR EXAMPLE 1

1. Bunzow, J. R., H. H. M. Van Tol, D. K. Grandy, P. Albert, J. Salon, M. Christie, C. A. Machida, K. A. Neve, and O. Civelli. Cloning and expressing of a rat $D_2$ dopamine receptor cDNA. *Nature (Lond.)* 336:783–787 (1988).
2. Kebabian, J. W., and D. B. Calne. Multiple receptors for dopamine. *Nature (Lond.)* 277:93–96 (1979).
3. De Camilli, P., D. Macconi, and A. Spada. Dopamine inhibits adenylate cyclase in human prolactin-secreting pituitary adenomas. *Nature (Lond.)* 278:252–254 (179).
4. Malgaroli, A., L. Vallar, F. R. Elahi, T. Pozzan, A. Spada, and J. Meldoiesi. Dopamine inhibits cytosolic $Ca^2$-increases in rat lactotroph cells: Evidence of a dual mechanism of action. *J. Biol. Chem.* 262:13920–13927 (1987).
5. Drouva, S. V., E. Rerat, C. Bihoreau, E. Laplante, R. Rasolonjanahary, H. Clauser, and C. Kordon. Dihydropyridine-sensitive calcium channel activity related to prolactin, growth hormone, and luteinizing hormone release from anterior pituitary cells in culture. Interactions with somatostatin, dopamine, and estrogens. *Endocrinology* 123:2762–2773 (1988).

b 6. Lacey, M. G., N. B. Mercuri, and R. A. North. Dopamine acts on D2 receptors to increase potassium conductance in neurones of the rab substantia nigra zona compacta. *J. Physiol. (Lond.)* 392:397–416 (1987).

7. Simmonds, S. H., and P. G. Strange. Inhibition of inositol phospholipid breakdown by $D_2$ dopamine receptors in dissociated bovine anterior pituitary cells. *Neurosci. Lett.* 60:267–272 (1985).

8. Enjalbert, A., F. Sladaczek, G. Guillon, P. Bertrand, C. Shu, J. Epelbaum, A. Garcia-Sainz, S. Jard, C. Lombard, C. Kordon, and J. Bockaert. Angiotensin II and dopamine modulate both cAMP and inositol phosphate productions in anterior pituitary cells: Involvement in prolactin secretion. *J. Biol Chem.* 261:4071–4075 (1986).

9. Judd, A. M., I. S. Login, K. Kovacs, P. C. Ross, B. L. Spangelo, W. D. Jarvis, and R. M. MacLeod. Characterization of the MMQ cell, a prolactin-secreting cloned cell line that is responsive to dopamine. *Endocrinology* 123:2341–2350 (1988).

10. Lefkowitz, R. J. and M. G. Caron. Adrenergic receptors: Models for the study of receptors coupled to guanine nucleotide regulatory proteins. *J. Biol. Chem.* 263:4993–4996 (1988).

11. Uhler, M. D., and G. S. McKnight. Expression of cDNAs for two isoforms of the catalytic subunit of cAMP-dependent protein kinase. *J. Biol. Chem.* 262:15202–15207, 1987.

12. Gorman, C., R. Padmanabhan, and B. H. Howard. High efficiency DNA-mediated transformation of primate cells. *Science* 231:551–553 (1983).

13. Cheng, Y.-C. and W. H. Prusoff. Relationship between the inhibition constant ($K_I$) and the concentration of inhibitor which causes 50 per cent inhibition ($I_{50}$) of an enzymatic reaction. *Biochem. Pharmacol.* 22:3099–3108 (1973).

14. Salomon, Y., C. Londos, and M. Rodbell. A highly sensitive adenylate cyclase assay. *Analyt. Biochem.* 58:541–548 (1974).

15. Peterson, G. L. A simplification of the protein assay method of Lowry et al. which is more generally applicable. *Analyt. Biochem.* 83:346–356 (1977).

16. Cote, T. E., E. A. Frey, C. W. Grewe, and J. W. Kebabian. Evidence that the dopamine receptor in the intermediate lobe of the rat pituitary gland is associated with an inhibitory guanyl nucleotide component. *J. Neural. Trans. Suppl.* 18:139–147 (1983).

17. Hamblin, M. W., and I. Creese. 3H-Dopamine binding to rat seriatal D-2 and D-$^3$ sites: Enhancement by magnesium and inhibition by guanine nucleotides and sodium. *Life Sci.* 30:1587–1595 (1982).

18. Weiss, S., M. Sebben, J. A. Garcia-Sainz, and J. Bockaert. $D_2$-Dopamine receptor-mediated inhibition of cyclic AMP formation in striatal neurons in primary culture. *Mol. Pharmacol.* 27:595–599 (1985).

19. Onali, P., M. C. Olianas, and G. L. Gessa. Characterization of dopamine receptors mediating inhibition of adenylate cyclase activity in rat striatum. *Mol. Pharmacol.* 28:138–145 (1985).

20. Agui, T., N. Amlaiky, M. G. Caron, and J. W. Kebabian. Binding of [$^{125}$I]-N-(p-aminophenethyl)spiroperidol to the D-2 dopamine receptor in the neurointermediate lob of the rat pituitary gland: A thermodynamic study. *Mol. Pharmacol.* 32:163–169 (1988).

21. Koch, S. W., B. K. Koe, and N. G. Bacopoulos. Differential effects of the enantiomers of 3-(3-hydroxyphenyl)-N-n-propylpiperidine (3-PPP) at dopamine receptor sites. *Eur. J. Pharmacol.* 92:279–283 (1983).

22. Meller, E., K. Bohmaker, Y. Namba, A. J. Friedhoff, and M. Goldstein. Relationship between receptor occupancy and response at striatal dopamine autoreceptors. *Mol. Pharmacol.* 31:592–598 (1987).

23. Borgundvaag, V., and S. R. George. Dopamine inhibition of anterior pituitary adenylate cyclase is mediated through the high-affinity state of the $D_2$ receptor. *Life Sci.* 37:379–386 (1985).

24. Abramson, S. N., M. W. Martin, A. R. Hughes, T. K. Harden, K. A. Neve, D. A. Barrett, and P. B. Molinoff. Interaction of β-adrenergic receptors with the inhibitory guanine nucleotide-binding protein of adenylate cyclase in membranes prepared from cyc-S49 lymphoma cells. *Biochem. Pharmacol.* 37:4289–4297 (1988).

25. Tashjian, A. H. Clonal strains of hormone-producing pituitary cells. *Meth. Enzymol.* 58:527–535 (1979).

26. Albert, P. R., K. Neve, J. Bunzow, and O. Civelli. Biological functions of the rat dopamine $D_2$ receptor cDNA expressed in $GH_4C_1$ rat pituitary cells. *Proc. Endocrine Soc.* 71:(in press).

Example 2

Summary

We have previously described a cDNA which encodes a binding site with the pharmacology of the $D_2$-dopamine receptor (Bunzow, J.R., et al. (19868) *Nature* 336, 783–787). We demonstrate here that this protein is a functional receptor, i.e., it couples to G-proteins to inhibit cAMP generation and hormone secretion. The cDNA was expressed in $GH_4C_1$ cells, a rat somatomammotrophic cell strain which lacks dopamine receptors. Stable transfectants were isolated and one clone, $GH_4ZR_7$, which had the highest levels of $D_2$-dopamine receptor mRNA on Northern blot, was studied in detail. Binding of $D_2$-dopamine antagonist $^3$H-spiperone to membranes isolated from $GH_4ZR_7$ cells was saturable, with $K_D$=96 pM, and $B_{max}$=2300 fmol/mg protein. Addition of GTP/NaCl increased the $IC_{50}$ value for dopamine competition for $^3$H-spiperone binding by two-fold, indicating that the $D_2$-dopamine receptor interacts with one or more G proteins. To assess the function of the dopamine binding site, acute biological actions of dopamine were characterized in $GH_4ZR_7$ sells. Dopamine decreased resting intra- and extracellular cAMP levels by 50–70% ($EC_{50}$=8±2 nM), and blocked completely VIP-induced enhancement of cAMP levels ($EC_{50}$=6±1 nM), which ranged from 8–12 times basal levels. Antagonism of dopamine-induced inhibition of VIP-enhanced cAMP levels by spiperone, (+)-butaclamol, (−)-sulpiride and SCH23390 occurred at concentrations expected from $K_I$ values for these antagonists at the $D_2$-receptor and was stereo-selective. Dopamine (as well as several $D_2$-selective agonists) inhibited forskolin-stimulated adenylate cyclase activity by 45±6%, with $EC_{50}$ of 500–800 nM in $GH_4ZR_7$ membranes. Dopaminergic inhibition of cellular cAMP levels and of adenylate cyclase activity in membrane preparations was abolished by pretreatment with pertussis toxin (50 ng/ml, 16h). Dopamine (200 nM) abolished VIP and TRH-induced acute prolactin release. These data show conclusively that the cDNA clone encodes a functional dopamine-$D_2$ receptor which couples to G proteins to inhibit adenylate cyclase, and both cAMP-dependent and cAMP-independent hormone secretion. The $GH_4ZR_7$ cells will prove useful in elucidating further the biochemistry of the dopamine $D_2$ receptor.

Introduction

The major element controlling PRL[1] secretion from the pituitary is the concentration of dopamine in the hypophyseal portal bloodstream (1). Dopamine acts via dopamine-$D_2$ receptors on pituitary lactotrophs to inhibit basal and hormone-stimulated secretion of PRL (1–5). The dopamine-$D_2$ receptor interacts with pertussis toxin-sensitive, inhibitory G proteins (6–9) to reduce adenylate cyclase activity, and to block enhancement of cAMP levels by other agents (6, 10–12). Dopamine also decreases $[Ca^{++}]_i$ in lactotrophs, and partially inhibits elevation of $[Ca^{++}]_i$ by other agents, such as TRH (13–15). Both dopaminergic inhibition of cAMP and of $[Ca^{++}]_i$ are mediated through coupling to one or more pertussis toxin-sensitive G proteins, and appear to contribute to dopamine inhibition of PRL secretion (15). The precise relation between these components of dopamine action has been difficult to study (15, 16) due to the presence of heterogeneous cell types, limitations of cell number, and variations in responsiveness of divers lactotroph preparations.

The recent cloning of the dopamine-$D_2$ receptor cDNA (17) provides a useful tool to examine the intracellular actions and regulation of the receptor. To examine whether the $D_2$-receptor clone directs synthesis of a functional receptor, and to define the pathway between dopamine-$D_2$ receptor activation and biological effect, we have transfected the dopamine-$D_2$ receptor cDNA into a pituitary-derived cell strain, $GH_4C_1$ cells. $GH_4C_1$ cells are rat pituitary cells which synthesize and secrete PRL and GH, and possess a variety of hormone, growth factor, and neurotransmitter receptors, second messenger systems, and ion channels and have provided an accessible model of lactotroph function (18, 19). However, these cells lack dopamine-$D_2$ receptors, which are present on normal lactotrophs, and thus provide an ideal host for studying the function of the dopamine-$D_2$ receptor. This report demonstrates that the gene product of the cDNA clone functions as a dopamine-$D_2$ receptor and couples to inhibitory G proteins to decrease cAMP accumulation[2] and PRL release. The $GH_4C_1$ transfectants characterized herein should provide a useful cell system in which the mechanisms of dopamine action at $D_2$ receptors may be studied further.

Experimental Procedures

Materials: Dopamine agonists and antagonists were from Research Biochemicals Incorporated (Waltham, Mass.), except quinpirole (Lilly), bromocryptine (Sandoz Research Institute), and (+) and (−)3-PPP (Astra). Rabbit antibody (lot CA-3) to 2-O-succinyl-cAMP-bovine serum albumin conjugate was obtained from ICN (Irvine, Calif.), rPRL standard and anti-rPRL antibody were from Dr. Salvatore Raiti, NIDDK, Bethesda, Md. Peptides were from Peninsula (, Calif.) or Sigma (St. Louis, Mo.). $\alpha^{32}P$-dCTP (2,200 Ci/mmol), $^{125}I$-2-O-(iodotyrosyl methyl ester)-succinyl cAMP (2,200 Ci/mmol), $^{125}I$-rPRL (2,200 Ci/mmol), $\alpha^{32}P$-ATP (10–50 Ci/mmol), $^{3}H$-cAMP (31.9 Ci/mmol) were from New England Nuclear (Boston, Mass.). All other chemicals were reagent grade, obtained primarily from Sigma.

Methods

Construction of pZEM-$D_2$-cDNA: The pZEM-3 plasmid (20) was cut at the Bgl II site between the metallothionein promotor and hGH 3'-flanking sequence. Full-length dopamine-$D_2$ cDNA (17) was excised from λGT10 with Sal I and was ligated to the cut pZEM-3 plasmid in the presence of DATP and dGTP (250 µM) and transformed into E. Coli strain XL-1 (Stratagene). Recombinants were characterized by their hybridization to $^{32}P$-labelled $D_2$-cDNA, followed by restriction analysis and DNA sequencing. Recombinants with cDNA inserts in the sense orientation were prepared and purified by CsCl gradient centrifugation for transfection into eucaryotic cells.

Cell Culture: $GH_4C_1$ cells, obtained from Dr. A. H. Tashjian, Jr. (Harvard University, Boston, Mass.) and subclones were grown in Ham's F10 medium, supplemented with 10% fetal bovine serum, at 37° C. in 5% $CO_2$. For studies of $^{3}H$-spiperone binding or adenylate cyclase activity, cells were grown in Dulbecco's modified Eagle's medium supplemented with 10% fetal bovine serum at 37° C. in 10% $CO_2$. Media were changed 12–24h prior to transfection or experimentation. For transfection, $GH_4C_1$ cells were grown to $2-4\times10^6$ cells/10 cm dish. 20 µg of pZEM-$D_2$cDNA and 1 µpRSV-neo were co-precipitated with calcium phosphate in 2 ml of Hepes-buffered saline, and placed over cells for 10–20 min. 8 ml of warm F10+10% fetal calf serum (pH 7.0) was added, and the cells incubated for 4–5 h, 37° C. The medium was removed and 15% glycerol in Hepes-buffered saline was added, and incubated for 3 min., 37° C. The plates were rinsed and fresh F10+10% fetal calf serum added, and the cells placed in the incubator for 16–20 h. Fresh medium supplemented with 700 µg/ml G418 (Geneticin, GIBCO, N.Y.) was added over the next 3–4 weeks, to select for stable transfectants expressing neo-resistance. Single colonies were isolated using sterile micropipette tips to take up individual colonies in 3–5 µl. Once stocks of the transfectant cell lines were stored frozen in liquid nitrogen, G418 was omitted from growth media.

RNA Isolation and Northern Blot Analysis: Cells were rinsed in calcium-free Hepes-buffered saline +0.02% EDTA and extracted with Tris-buffered guanidinium hydrochloride, centrifuged (33,000 rpm, 16 h) through a 1.7 g/ml CsCl pad, and the pellets extracted with phenol/chloroform and ethanol precipitated (21). RNA was resuspended and quantitated by UV absorbance at OD=260 nm. For Northern blots, RNA was denatured in glyoxal/dimethylsulfoxide (1 h, 50° C.), and run on a 1% agarose gel in 10 mM sodium phosphate. RNA was blotted overnight onto nylon membrane (N-bond, Amersham), baked at 80° C. for 2 h. Prehybridization was as described, for 6 h at 42° C. Random-primed $^{32}P$-labelled 1.6 kb BamHI-BglII fragment of the $D_2$-cDNA ($1-2\times10^6$ dpm/µg) was used for hybridization, 16–20 h at 42° C. in 50% formamide. Blots were washed in 2xSSC for 10 min, room temperature, followed by 3x15 min. wash in 0.2xSSC, 0.5% SDS, 70° C., and exposed to X-ray film overnight at −80° C., with intensifying screen.

Ligand Binding: Cell membranes were prepared by first replacing growth medium with ice-cold hypotonic buffer (1 mM Hepes, pH 7.4, 2 mM EDTA). After swelling for 10–15 min, the cells were scraped from the plate and centrifuged at 24,000g for 20 min, lysed with a Brinkman Polytron homogenizer at setting 6 for 10 sec in Tris-isosaline (50 mM Tris, pH 7.4, 0.9% NaCl) and stored at −70° C. for receptor binding experiments, or resuspended in 50 mM Tris, pH 7.4, centrifuged as above, and resuspended in 50 mM Tris for immediate use in adenylate cyclase assay (below). For binding assays, the membrane preparation was thawed, centrifuged (24,000 gx20 min) and resuspended in Tris-isosaline except where indicated. Aliquots of membrane preparation were added to tubes containing 50 mM Tris, pH 7.4, 0.9% NaCl, 0.025% ascorbic acid, 0.001% bovine serum albumin, $^{3}H$-spiperone and indicated drugs. (+)-Butaclamol (2 µM) was used to define nonspecific binding, which was less than 10% of total binding at concentrations of radioligand near the $K_D$ value. Assays were carried out in duplicate, in a volume of 2 ml for saturation analyses or 1 ml for inhibition analyses. Incubations were initiated by addition of 10–50 μg of membrane protein, carried out at 37° C. for 50 min, and stopped by addition of 10 ml of ice-cold buffer (10 mM Tris, pH 7.4, 0.9% NaCl) to each tube. The samples were immediately filtered through glass-fibre filters (Schleicher and Schuell No. 30) and washed with 10 ml of ice-cold buffer. Radioactivity retained on the filter was counted using a Beckman LS 1701 scintillation counter. In experiments to examine the effect of GTP on dopamine binding, cells were harvested, centrifuged, resuspended in Tris-$Mg^{++}$(50 mM Tris, pH 7.4, 4 mM $MgCl_2$) and incubated for 15 min, 37° C. After centrifugation, the resuspended protein was added to assays containing Tris-$Mg^{++}$ with no added GTP or NaCl, or Tris-$Mg^{++}$ with 120 mM NaCl and 100 μm GTP.

cAMP and PRL Assay: Cells were plated in 6-well, 35 mm dishes, 3–7 days prior to experimentation. Cells were pre-incubated in 2 mil/well warm F10+0.1% (–)-ascorbic acid+20 mM Tris (pH 7.2) (FAT) for 5–10 min, followed by addition of 1 ml/well of FAT+100 μm IBMX+experimental compounds, and incubated for 30 min. at 37° C. Experimental compounds were diluted 200- to 1000-fold from stock solutions made immediately prior to assay. The final ethanol concentration never exceeded 0.1%, a concentration without effect on basal or VIP-enhanced cAMP or PRL levels in $GH_4ZR_7$ cells. Media were collected, and the cells were lysed immediately in 1 ml of boiling water. Cell lysates and media were centrifuged (2000×g, 10 min., 4° C.), and the supernatants collected for assay as cell extracts. Cell extracts and media samples were frozen at –20° C. until assay, if not assayed immediately. cAMP was assayed by a specific radioimmunoassay as described (22), with antibody used at 1:500 dilution. After 16 h incubation at 4° C., 20 μl of 10% BSA and 1 ml of 95% ethanol were added consecutively to precipitate the antibody-antigen complex. Standard curves showed $IC_{50}$ of 0.5±0.2 pmol using cAMP as standard. PRL was assayed in the media samples obtained as described above, except that IBMX was omitted during the 30 min incubation in FAT medium. PRL levels were determined by specific radioimmunoassay using Staphyloccus A lysate (IgSorb, The Enzyme Center, Malden, Mass.) to precipitate antigen-antibody complexes (23). Standard curves gave $IC_{50}$ of 36±6 ng using rPRL standard.

Adenylate Cyclase Assay: The conversion of $\alpha^{32}P$-ATP to $^{32}P$-cAMP was determined essentially as described by Salomon et al. (24). Membranes (10–50 μg) were added in a volume of 100 μl to an assay of 200 μl containing 50 mM Tris, pH 7.4, 5 mM cAMP, 1 mM IBMX, 1 mM $MgCl_2$, 0.5 mM EGTA, 0.25 mM ATP, 30 μm GTP, and about $2\times10^6$ cpm of $\alpha^{32}P$-ATP, and various drugs. Assays carried out in triplicate were initiated by warming to 25° C. and terminated by cooling to 0° C. Trichloroacetic acid (100 μl of 30% solution) was added to each assay, and $^3H$-cAMP (30,000 cpm) was added to each tube as an internal standard. The assay volume was increased to 1 ml by addition of water, and tubes were centrifuged (2000 g×10 min). cAMP in the supernatant was isolated by sequential chromatography on columns containing Dowex AG50W-X4 resin and neutral alumina. The 2-ml eluate from each alumina columnwas dissolved in 10 ml of Bio-Safe II (RPI, Mount Prospect, Ill.) for liquid scintillation counting.

Calculations: Data from cAMP and PRL assays are expressed as means +standard error for triplicate determinations. Curve-fitting parameters were obtained by nonlinear regression analysis using the Enzfitter program (Elsevier Biosoft). Average affinity, $EC_{50}$ and $IC_{50}$ values are geometric means of the indicated number of experiments. In competition experiments, $K_I$ values were calculated from experimentally determined $IC_5$ values by the method of Cheng and Prusoff (25). All experiments were representative of 3–5 independent trials, with the exception of that presented in FIG. 16 (2 trials).

Results

Characterization of Stable Transfectants: $GH_4C_1$ cells were cotransfected with pZEM-$D_2$-cDNA and pRSV-neo, and colonies resistant to the antibiotic G418 were isolated and initially characterized by Northern blot analysis. One clone, $GH_4ZR_7$, had higher levels of 2.5 kb $D_2$ mRNA than other clones (FIG. 13A). Wild-type (untransfected) $GH_4C_1$ cells, as well as a $GH_4C_1$ cell transfectant ($GH_4ZD_{10}$) expressing the rat 5-$HT_{1A}$ receptor gene in the pZEM-3 vector[3] showed no hybridization to the $D_2$-receptor probe. Pretreatment of $GH_4ZR_7$ cells with 100 μM $ZnSO_4$ for 36 h induced a marked enhancement of $D_2$ receptor mRNA, indicating that the transcribed RNA is regulated by the zinc-sensitive metallothionein promotor (20). The $GH_4ZR_7$ clone was used for further analysis (below) because of the high levels of dopamine-$D_2$ receptor expression in this clone.

Figures 1, 13B:
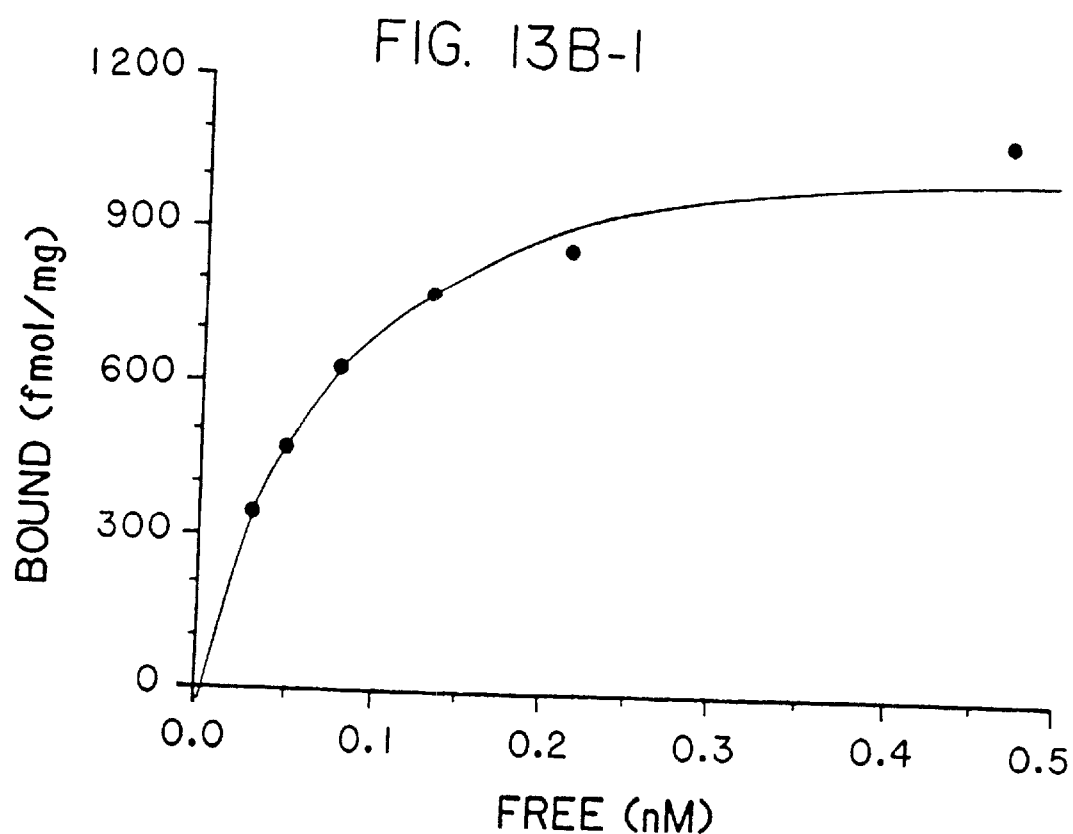
Figures 2, 13B:
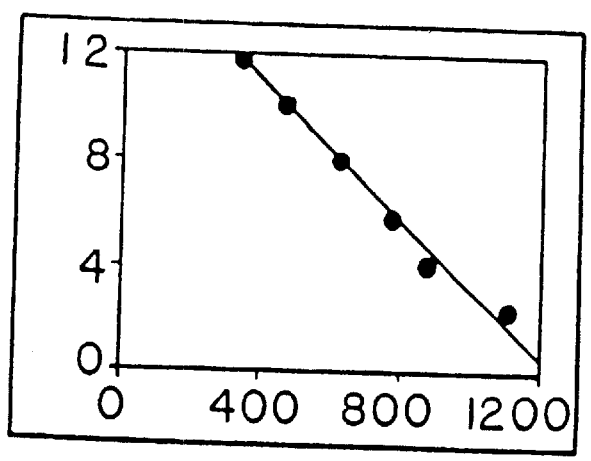

Specific binding of the selective dopamine-$D_2$ receptor antagonist, $^3H$-spiperone, was assayed in crude membranes prepared from $GH_4ZR_7$ cells (FIG. 13B). The $GH_4ZR_7$ membranes showed a saturable component of $^3H$-spiperone binding which was displaced by 2 μM (+)-butaclamol, whereas membranes from wild-type $GH_4C_1$ cells showed no specific $^3H$-spiperone binding (data not shown). In 5 experiments, the $GH_4ZR_7$ cell membranes showed maximal specific $^3H$-spiperone binding of 2046±315 fmol/mg of protein, and a mean $K_D$ value of 96±1 pM. These values demonstrate robust expression of dopamine-$D_2$ binding sites receptors in these cells with affinity for $^3H$-spiperone comparable to that obtained in rat striatal membranes, and in $Ltk^-$ cells transfected with pZEM-$D_2$-cDNA (17).

To ascertain whether the expressed dopamine binding site interacted with a G protein, inhibition of $^3H$-spiperone binding by dopamine was assayed in $GH_4ZR_7$ cell membranes, in the absence or presence of 100 μM GTP and 120 mM NaCl (FIG. 13C). Assays were carried out in the presence of 4 mM $MgCl_2$ to promote high affinity binding of dopamine. In the absence of added GTP and NaCl, dopamine inhibited $^3H$-spiperone binding with $IC_{50}$=49±15 μM, and Hill coefficient of 0.69, suggesting the presence of high and low affinity sites for dopamine. Analyzing the data according to a model assuming the presence of two classes of binding sites indicated that 46±15% of the receptors had a high affinity ($K_D$=0.5 μM) for dopamine and the remaining receptors had lower affinity (30 μM) for the agonist. In the presence of GTP and NaCl, the $IC_{50}$ for dopamine was shifted two-fold to 109±20 μM ($K_I$=17 μM) with Hill coefficient closer to unity (0.93). Thus, the presence of GTP/NaCl converts the dopamine receptors from a heterogeneous population of high and low affinity receptors to a nearly homogeneous population of receptors in a low-affinity agonist state, as observed in striatal membrane preparations (6, 7). These data suggest that the cloned dopamine binding site interacts with G proteins when expressed in $GH_4$ cells.

Figure 14B:
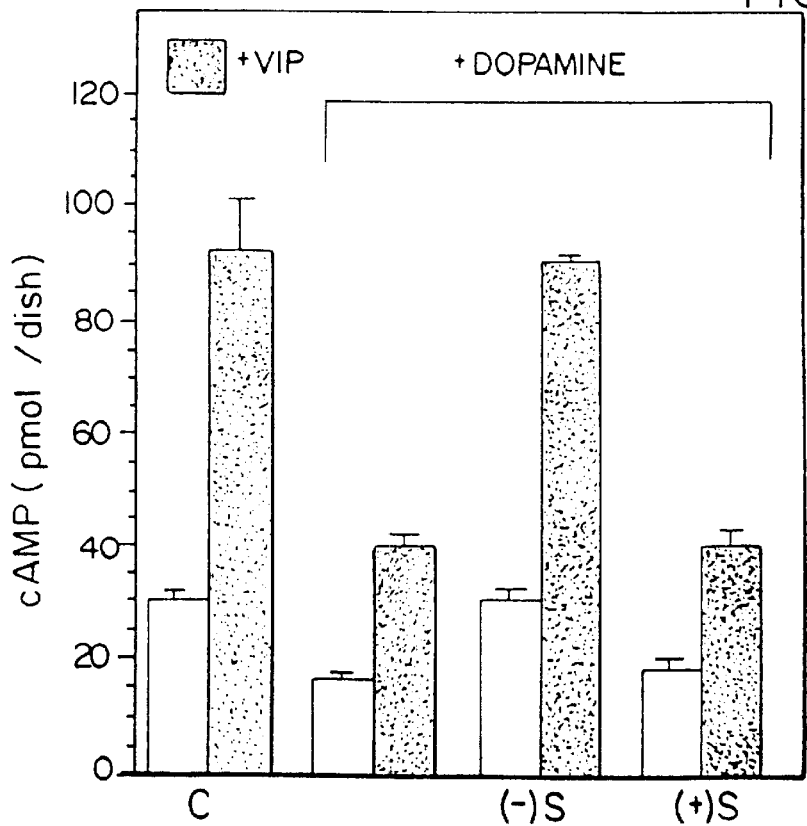

Dopamine Actions on cAMP and PRL Levels: To test directly the function of the expressed dopamine-$D_2$ receptor clone, the actions of dopamine on cellular cAMP levels were measured. These assays were conducted in the presence of 100 μM IBMX, to inhibit phosphodiesterase activity in these cells (22). Thus, the observed changes in cAMP levels reflect changes in the rate of synthesis of cAMP rather than changes in its degradation. Dopamine actions on basal cAMP levels were measured, as well as dopamine inhibition of VIP-enhanced levels of cAMP. $GH_4C_1$ cells respond to VIP with an enhancement of cAMP accumulation (FIG. 14A) as described by others (22, 26). Dopamine had no effect on extracellular cAMP levels in wild-type $GH_4C_1$ cells, whether VIP was omitted or present during the incubation. This result is consistent with the lack of $D_2$-dopamine receptor mRNA and binding in $GH_4C_1$ cells (FIG. 13), and indicates that these cells also lack a detectable $D_2$-dopamine response since dopamine does not elevate cAMP concentrations. In media from $GH_4ZR_7$ cells, dopamine inhibited both basal cAMP levels (by 50–70%), and reduced VIP-enhanced cAMP to basal levels. These actions of dopamine to reduce cAMP levels were consistently observed in all experiments and dopamine was equally effective in lowering intracellular cAMP levels (FIG. 14B). As observed previously in $GH_4C_1$ cells (22), both intra- and extracellular cAMP levels change in parallel, although changes in extracellular cAMP may be more pronounced due to lower recovery of extracted intracellular cAMP. Dopamine actions on cAMP accumulation were blocked by (−)-sulpiride, a highly selective dopamine-$D_2$ antagonist, whereas the inactive stereoisomer, (+)-sulpiride, did not block dopaminergic inhibition of cAMP accumulation. Stereo-selective lockade by sulpiride suggested that inhibition of cAMP levels in $GH_4ZR_7$ by dopamine was mediated by activation of a dopamine-$D_2$ receptor not present in wild-type $GH_4C_1$ cells.

The physiological outcome of dopamine action is inhibition of secretion, which was assayed by measuring acute (30 min) PRL release in $GH_4ZR_7$ cells (FIG. 14D). VIP and TRH enhanced PRL secretion 1.5- and 3-fold, respectively. VIP is thought to enhance PRL release by a cAMP-dependent mechanism (22, 23, 26), while TRH acts by a cAMP-independent mechanism linked to calcium mobilization (19, 27). Dopamine did not inhibit basal PRL release, but both VIP- and TRH-induced enhancement of PRL secretion were blocked by dopamine. Thus, dopamine blocked both cAMP-dependent and cAMP-independent secretion in $GH_4ZR_7$ cells. These actions of dopamine were reversed by (−)-sulpiride, but not by (+)-sulpiride. In $GH_4C_1$ cells, dopamine had no effect on basal, VIP-stimulated, or TRH-stimulated secretion of PRL (data not shown).

To examine whether concentrations required for biological response correlated with affinity for the dopamine-$D_2$ receptor, dose-response relations were examined for dopamine actions on cAMP levels (FIG. 15). Dopamine potently inhibited intra- and extracellular levels of cAMP with similar $EC_{50}$ values. Furthermore, dopamine inhibited both basal and VIP-enhanced cAMP accumulation with $EC_{50}$ values of 8±2 nM and 6±1 nM, respectively. These data demonstrate that dopamine inhibits both basal and stimulated cAMP accumulation with approximately equal potency. The high potency of these inhibitory actions of dopamine supports the assertion that $GH_4ZR_7$ cells express a functional dopamine-$D_2$ receptor.

The pharmacological specificity of dopaminergic inhibition of VIP-enhanced levels of cAMP in $GH_4ZR_7$ was examined further using specific receptor antagonists (FIG. 16). The data show that certain receptor antagonists reverse dopamine-induced inhibition of VIP-enhanced levels of extracellular cAMP. Maximal cAMP (100%) corresponded to cAMP levels in the presence of VIP alone. Low concentrations of dopamine-$D_2$ antagonists (spiperone, (+)-butaclamol, (−)-sulpiride) blocked dopamine action, whereas SCH23390, a specific dopamine-$D_1$ antagonist, was active only at very high concentrations. Inactive stereoisomers of $D_2$-antagonists ((−)-butaclamol, (+)-sulpiride (FIG. 14C)) had little or no effect on dopamine action. Antagonists added in the absence of dopamine did not alter cAMP concentrations. Estimated $K_I$ values obtained from $IC_{50}$ values for the antagonists (see description of FIG. 16) were similar to values determined from binding competition studies of the dopamine $D_2$ receptor (17), showing that inhibition of cAMP levels by dopamine in $GH_4ZR_7$ cells is mediated by a receptor which is pharmacologically indistinguishable from the dopamine-$D_2$ receptor.

Inhibition of Adenylate Cyclase: To assess directly inhibition of adenylate cyclase activity by dopamine receptor agonists, the conversion of $^{32}P$-ATP to $^{32}P$-cAMP was measured in membranes prepared from $GH_4ZR_7$ cells (FIG. 17). Dopamine inhibited total forskolin (10 $\mu$M)-stimulated activity by 45% with an average $EC_{50}$ value of 0.36 $\mu$M (n–5). As observed in pituitary (11) and striatal (28) membranes, bromocryptine behaved as partial agonist, maximally inhibiting enzyme activity by 23% ($EC_{50}$=6 nM). Inhibition of adenylate cyclase activity by selective $D_2$-agonists was stereo-selective. For example, quinpirole inhibited forskolin-stimulated cyclase activity by 41% ($EC_{50}$+0.32 nM), whereas LY181990, the inactive (+)-enantiomer of quinpirole, cause no consistent reduction in enzyme activity. Similarly, (+)-3-PPP ($EC_{50}$=0.86 nM) was as efficacious as dopamine, whereas the enantiomer (−)-3-PPP did not consistently *,educe adenylate cyclase activity. VIP also stimulated adenylate cyclase activity in $GH_4ZR_7$ cell membranes, as reported for wild-type $GH_4C_1$ cell membranes (29). Total activity stimulated by 200 nM VIP was 22±7 pmol/mg protein/min (n=3), and VIP-enhanced activity was inhibited 41% by dopamine (100 $\mu$M), compared to 50–55% inhibition in rat anterior pituitary membranes (11). No effect of dopamine on basal adenylate cyclase activity was observed in these preparations. Nevertheless, inhibition by dopamine of forskolin- or VIP-stimulated adenylate cyclase activity provides a likely mechanism for inhibition of cAMP accumulation by dopamine in $GH_4ZR_7$ cells.

Pertussis Toxin Sensitivity: Sensitivity to pertussis toxin is a hallmark of receptors, such as the dopamine-$D_2$ receptor (6–12, 15), which couple to inhibitor G proteins (e.g., $G_i$ or $G_o$) to induce responses. Pretreatment of $GH_4ZR_7$ cells with pertussis toxin for 16 h (FIG. 12) uncoupled dopamine-mediated inhibition of forskolin-stimulated membrane adenylate cyclase activity, and abolished inhibition of basal and VIP-stimulated cAMP accumulation by dopamine. The concentration of pertussis toxin and incubation time used produce maximal blockage of somatostatin responses in wild-type cells (30), and the dopamine responses were almost completely inhibited under these conditions. By contrast, basal and VIP-stimulated cAMP accumulation, as well as basal and forskolin-stimulated cyclase activity, were not significantly altered by pertussis toxin pretreatment. These data support the assertion that the expressed cDNA clone codes for a dopamine-$D_2$ binding site which is functionally coupled to inhibitory G proteins present in $GH_4$ cells, and thus represents a bona fide receptor.

Discussion

The cDNA clone coding for a dopamine-$D_2$ binding site (17) was expressed in $GH_4C_1$ cells to determine whether the clone expresses a functional $D_2$ receptor, which is coupled by pertussis toxin-sensitive inhibitory G proteins to inhibition of adenylate cyclase, cAMP accumulation, and inhibition of PRL secretion (6–12, 15). Dopamine-$D_2$ receptors were expressed specifically from a $D_2$-cDNA construct under the regulation of the mouse metallothionein promotor (20), as evidenced by the presence of $D_2$ receptor mRNA in the $GH_4ZR_7$ transfectant.

Dopamine-$D_2$ receptor mRNA levels were undetectable in untransfected $GH_4C_1$ cells, or in cells transfected with the rat 5-$HT_{1A}$ receptor subtype (FIG. 13A). The mRNA species found in $GH_4ZR_7$ cells was approximately the same molecular weight as $D_2$ receptor mRNA found in rat brain (17). Levels of dopamine-$D_2$ mRNA increased by addition of 100 μM $Zn^{++}$ in $GH_4ZR_7$ cells, indicating that expression of the mRNA is controlled by the $Zn^{++}$-sensitive mouse metallothionein promotor, and does not represent transcription of the endogenous gene. Specific binding of $^3$H-spiperone binding was present only in $GH_4ZR_7$ cells, and was increased by 100 μM $Zn^{++}$, and thus correlated with the expression of dopamine-$D_2$ receptor mRNA in these cells. The $D_2$-receptor mRNA was transcribed to yield robust expression of high affinity dopamine-$D_2$ binding sites in $GH_4ZR_7$ cells.

The presence of dopamine-$D_2$ binding in the $GH_4ZR_7$ transfectant correlated with potent and powerful inhibition of cAMP accumulation and PRL release, as well as inhibition of forskolin-stimulated adenylate cyclase activity, actions of dopamine not observed in untransfected $GH_4C_1$ cells. These inhibitory actions of dopamine match exactly the known physiological actions of dopamine in pituitary lactotrophs (1, 2). In particular, dopamine controls PRL secretion and cAMP accumulation in lactotrophs such that stimulation of these processes does not occur unless dopamine concentrations decrease to low levels (1, 3–5). Similarly, in the present of maximal concentrations of dopamine, VIP does not enhance cAMP levels or PRL secretion in $GH_4ZR_7$ cells (FIG. 14). The potency of dopamine inhibition of basal and VIP-enhanced cAMP accumulation in $GH_4ZR_7$ cells (FIG. 15) was in the range of concentration expected for lactotrophs, given that dopamine concentrations in hypophyseal portal blood vary from 7 nM in female rates during proestrous, to 20 nM during estrous, and are 3 nM in male rats (31). Detailed analysis of the pharmacology of dopamine-induced inhibition of adenylate cyclase and cAMP accumulation using specific agonists and antagonists are fully consistent with the conclusion that dopaminergic actions in $GH_4ZR_7$ cells are mediated by a receptor indistinguishable from the dopamine-$D_2$ receptor.

The discrepancy between the measured affinity of dopamine (FIG. 13C), and the potency of dopamine to inhibit cAMP accumulation (FIG. 13) raises the possibility that $GH_4ZR_7$ cells have "spare" receptors, i.e., a sufficient excess of binding sites to shift the $EC_{50}$ for biological action to values lower than the $K_D$ value. An alternative explanation is that the receptor in membrane preparations has a lower affinity for agonists (but unchanged affinity for antagonists since measured $IC_{50}$ values correlated with $K_I$ values) than in intact cells. Since cytosolic or membrane-associated components present in intact cells are not entirely replaced in membrane binding and adenylate cyclase assay conditions, it is possible that components which allow for optimal function of the dopamine receptor in membrane preparations are lacking. This assertion is supported by the $EC_{50}$ value for inhibition of particulate adenylate cyclase by dopamine (360 nM), which is close to $K_I$ values obtained for dopamine from binding competition experiments (500 nM), but 100-fold higher $EC_{50}$ values (6–8 nM) obtained for inhibition of cAMP levels by dopamine in intact cells. This difference in conditions may explain the observed differences between assays in intact versus particulate preparations. However, affinities of antagonists correlated well with estimated $K_I$ values obtained from cAMP accumulation experiments (FIG. 16), indicating that antagonist binding is similar in membranes and whole cells.

Further evidence of coupling of the expressed dopamine-$D_2$ binding site to G proteins is the shift of dopamine binding affinity to lower affinity in the presence of GTP. Such GTP-induced shifts in affinity have been reported for dopamine binding in membranes from rat brain (6, 7), and are due to interaction of the receptor with G proteins (8, 9). In the presence of GTP, the G protein dissociates from the receptor leaving the receptor in a low affinity agonist state (6, 7). In the case of dopamine, the difference between the affinities of the two states is small, hence the GTP-induced shift to the low-affinity state is small (two-fold) and requires the presence of $Na^+$ion to maximize dissociation of the G protein (28). The observation of a GTP-induced shift in dopamine affinity suggests that the expressed dopamine receptor is associated with one or more G proteins in $GH_4ZR_7$ cell membranes.

Although the inhibitory actions of dopamine indicate that the receptor couples to inhibitory G proteins, this was tested more directly by pretreating $GH_4ZR_7$ cells with pertussis toxin to inactivate inhibitory G proteins (30). Pertussis toxin pretreatment completely blocked dopamine actions, without altering basal or VIP-stimulated cAMP accumulation. Thus, pertussis toxin prevented the dopamine-enhanced transduction of biological responses, presumably by uncoupling the dopamine-$D_2$ receptor from inhibitory G proteins. Unlike other systems (32), but as seen in wild-type $GH_4C_1$ cells (30), enhancement of cAMP levels by stimulators (e.g., VIP) was not augmented in pertussis toxin-treated $GH_4ZR_7$ cells, nor were basal cAMP levels altered by pertussis toxin. This suggests that inhibitory G proteins present in $GH_4ZR_7$ cells do not inhibit cAMP generation tonically.

The presence of somatostatin receptors on $GH_4C_1$ cells (33) allows for direct comparison of the inhibitory actions of somatostatin and dopamine. Like dopamine, somatostatin does not inhibit basal adenylate cyclase activity (29) or basal PRL secretion (30). Somatostatin-induced inhibition of VIP-stimulated cyclase activity (29), VIP-enhanced cAMP accumulation (22), and PRL secretion (23, 30) in $GH_4C_1$ cells were all about half the maximal inhibition induced by dopamine in $GH_4ZR_7$ cells. Indeed, in $GH_4ZR_7$ cells, somatostatin was half as effective as dopamine at inhibiting VIP-enhanced cAMP accumulation (data not shown). The larger effects of dopamine were not due to the presence of an excessive number of $D_2$ receptors since the receptor number under conditions of cAMP accumulation and PRL secretion experiments was less than 10,000 sites/cell, smaller than somatostatin receptor number (13,000 sites/cell) in $GH_4C_1$ cells (33). It is apparent that the dopamine receptors expressed in these cells are more effective at transducing inhibitory actions than somatostatin receptors, suggesting a more effective coupling of the dopamine receptor to the G proteins present in GH cells.

A second reason for expressing the dopamine-$D_2$ receptor cDNA in $GH_4C_1$ cells was to establish a new model system in which to study dopamine actions and $D_2$ receptor mechanisms. Current studies on dopamine action in rat lactotrophs, the most accessible cell system expressing dopamine-$D_2$ receptors until recently (16), have come to divergent conclusions on mechanisms of dopamine inhibition. In neurons, dopamine hyperpolarizes membrane potential (34) by opening potassium channels (35), actions mediated by coupling of the $D_2$ receptor to inhibitory G proteins (15). Membrane hyperpolarization induced by dopamine in lactotrophs (36) would close calcium channels, decreasing basal calcium influx and explaining observed decreases in basal $[Ca^{++}]_i$ induced by dopainine (13–15, 37, 38). However, dopamine has been observed to increase $[Ca^{++}]_i$ in certain pituitary cells (37). By examining dopamine-induced changes in $[Ca^{++}]_i$ in $GH_4ZR_7$ cells it will be possible to specifically associate the $D_2$ receptor with changes in $[Ca^{++}]_i$ and to ascertain the role of $[Ca^{++}]_i$ in mediating dopamine inhibition of hormone secretion. Another unresolved issue is the mechanism by which dopamine inhibits enhancement of secretion and by calcium-mobilizing hormones such as TRH. While some report inhibition by dopamine of TRH-induced enhancement of phosphatidyl inositol turnover (39, 40) and $[Ca^{++}]_i$ (13, 14), others find no change (38, 41). The observed inhibition by dopamine of TRH-induced PRL release in $GH_4ZR_7$ cells (FIG. 14C) suggests that dopamine may be coupled by G proteins to processes (e.g., opening of potassium channels) which alter TRH-induced calcium-mobilization or phosphatidyl inositol turnover. $GH_4ZR_7$ cells will provide a homogeneous, abundant, and highly-responsive preparation in which to study these and other questions regarding mechanisms of the dopamine-$D_2$ receptor.

The data presented in this report indicate that the expressed clone (17) possesses the pharmacology of the dopamine-$D_2$ receptor in all actions investigated including inhibition of PRL secretion, cAMP generation, and adenylate cyclase activity. The $D_2$ clone meets five basic criteria for classification as a functional G protein-coupled receptor: 1) the cDNA clone for the dopamine-$D_2$ binding site possesses the archetypical structure of G protein-coupled receptors; 2) the clone expresses a protein with saturable and specific binding properties; 3) agonist binding affinity to the expressed binding site is decreased in the presence of GTP; 4) the expressed receptor is coupled to functions (e.g., inhibition of adenylate cyclase) known to be regulated by G proteins; 5) agents (e.g., pertussis toxin) which uncouple G protein function uncouple activation of the expressed receptor from generation of the appropriate response. In conclusion, the interaction of the cloned dopamine-$D_2$ receptor with G proteins is productive, leading to activation of a, or ao subunits and consequent inhibition of cAMP and PRL levels by both cAMP-dependent and cAMP-independent mechanisms.

REERRENCES FOR EXAMPLE 2

1. Ben-Jonathan, N. (1985), Endocr. Rev. 6, 564–589.
2. Memo, M., Missale, C., Carruba, M. O., and Spane, P. F. (1986), J. Neural Transm. (Suppl.) 22, 19–32.
3. Martinez de la Escalera, G., and Weiner, R. I. (1986), Endocrinology 123, 1682–1687.
4. Lopez, F. J., Dominguez, J. R., Sanchez-Criado, J. E., and Negro-Vilar, A. (1988), Endocrinology 124, 527–535.
5. Ibid, pp. 536–542.
6. Sibley, D. R., DeLean, A., and Creese, I. (1982), J. Biol. Chem. 257, 6351–6361.
7. DeLean, A., Kilpatrick, B. F., and Caron, M. G. (1982), Mol. Pharmacol. 22, 290–297.
8. Senogles, S. E., Benovic, J. L., Amlaiky, N., Unson, C., Milligan, G., Vinitsky, R., Spiegel, A. M., Caron, M. G. (1987), J. Biol. Chem. 262, 4860–4867.
9. Ohara, K., Haga, K., Berstein, G., Haga, T., Ichiyama, A., and Ohara, K. (1988), Mol. Pharmacol. 33, 290–296.
10. Deiamilli, P., Macconi, D., and Spada, A. (1979), Nature 278, 252–254.
11. Onali, P., Schwartz, J. P., and Costa, E. (1981), P. N. A. S. 78, 6531–6534.
12. Cronin, M. J., Myer, G. A., MacLeod, R. M., and Hewlett, E. (1983), Am. J. Physiol. 244, E499–E504.
13. Schofield, J. G. (1983), F. E. B. S. Lett. 159, 79–82.
14. Margaroli, A., Vallar, L., Elahi, F. R., Pozzan, T., Spada, A., and Meldolesi, J. (1987), J. Biol. Chem. 261, 13920–13927.
15. Vallar, L. and Meldolesi, J. (1989), TIPS 10, 74–77.
16. Judd, A. M., Login, I. S., Kovacs, K., Ross, P. C., Spangelo, B. L., Jarvis, W. D., and MacLeod, R. M. (1988), Endocrinology 123, 2341–2350.
17. Bunzow, J. R., VanTol, H. H. M., Grandy, D. K., Albert, P., Salon, J., Christie, M., Machida, C., Neva, K. A., and Civelli, O. (1988), Nature 336, 783–787.
18. Tashjian, A. H., Jr. (1979), Meth. Enzymol. 58, 526–535.
19. Ozawa, S., and Sand, O. (1986), Physiol. Rev. 66, 887–952.
20. Uhler, M., and McKnight, G. S. (1987), J. Biol. Chem. 262, 15202–15207.
21. Chirgwin, J. M., Prybyla, A. E., MacDonald, R. J., and Rutter, W. J. (1979).
22. Dorflinger, L. J., and Schonbrunn, A. (1983), Endocrinology 113, 1541–1550.
23. Dorflinger, L. J., and Schonbrunn, A. (1983), Endocrinology 113, 1551–1558.
24. Salomon, Y., Londos, C., and Rodbell, M. (1974), Analyt. Biochem. 58, 541–548.
25. Cheng, Y. -C., and Prusoff, W. H. (1973), Biochem. Pharmacol. 22, 3099–3108.
26. Gourdji, D., Bataille, D., Vauclin, N., Grouselle, D., Rosselin, G., and Tixier-Vidal, A. (1979), FEBS Lett. 104, 165–168.
27. Albert, P. R., and Tashjian, A. H., Jr. (1984), J. Biol. Chem. 259, 15350–15363.
28. Onali, P., Olianas, M. C., and Gessa, G. L. (1985), Mol. Pharmacol. 28, 138–145.
29. Koch, B. D., and Schonbrunn, A. (1984), Endocrinology 114, 1784–1790.
30. Koch, B. D., Dorflinger, L. D., and Schonbrunn, A. (1985), J. Biol. Chem. 260, 13138–13145.
31. Ben-Jonathan, N., Oliver, C., Weiner, H. J., Mical, R. S., and Porter, J. C. (1977), Endocrinology 100, 452–458.
32. Kurose, H., Katada, T., Amano, T., and Ui, M. (1983), J. Biol. Chem. 258, 4870–4875.
33. Schonbrunn, A., and Tashjian, A. H., Jr. (1978), J. Biol. Chem. 253, 6473–6483.
34. Bunney, B. S., Aghajanian, G. K., and Roth, R. H. (1973), Nature (New Biol.) 245, 123–125.
35. Lacey, M. G., Mercuri, N. B., and North, R. A. (1987), J. Physiol. 392, 397–416.
36. Taraskevich, P. S., and Douglas, W. W. (1978), Nature 276, 832–834.
37. Winiger, B. P., Wuarin, F., Zahan, G. R., Wollheim, C. B., and Schlegel, W. (1987), Endocrinology 121, 2222–2228.
38. Law, G. J., Pachter, J. A., and Dannies, P. (1988), Mol. Endocrinol. 2, 966–972.
39. Journot, L., Homburger, V., Pantaloni, C., Priam, M., Bockaert, J., and Enjalbert, A. (1987), J. Biol. Chem. 262, 15106–15110.
40. Vallar, L., Vicentini, L. M., and Meldolesi, J. (1988), J. Biol. Chem. 263, 10127–10134.
41. Canonico, P. L., Jarvis, W. D., Judd, A. M., and MacLeod, R. M. (1986), J. Endocrinol. 110, 389–393.

FOOTNOTES

[1]The abbreviations used are: PRL, prolactin; GH, growth hormone; $[Ca^{++}]_i$, cytosolic free calcium concentration; VIP, vasoactive intestinal peptide; TRH, thyrotropin-releasing hormone; IBMX, 3-isobutyl-1-methyl xanthine; YD, equilibrium dissociation constant; $EC_{50}$ ($IC_{50}$), concentration required to elicit a half-maximal effect (inhibition).

[2] These results have been presented in part at the 71[St] Annual Endocrine Meetings, Seattle, Wash., Abstract #1278.

[3] Albert, P. R., et al., manuscript in preparation.

Example 3

A clone encoding a human dopamine $D_2$ receptor was isolated from a pituitary cDNA library and sequenced. The deduced protein sequence is 96% identical with that of the cloned rat receptor [Bunzow et al. (1988) Nature 336, 783–787] with one major difference: The human receptor contains an additional 29 amino acids in its putative third cytoplasmic loop. Southern blotting demonstrated the presence of only one human dopamine $D_2$ receptor gene. Two overlapping phage containing the gene were isolated and characterized. DNA sequence analysis of these clones showed that the coding sequence is .interrupted by six introns and that the additional amino acids present in the human pituitary receptor are encoded by a single exon of 87-basepairs. The involvement of this sequence in alternative splicing and its biological significance are discussed.

Introduction

Dopamine neurons in the vertebrate central nervous systemtare involved in the initiation and execution of movement, the maintenance of emotional stability, and the regulation of pituitary function. Several human neurological diseases, including Parkinson's Disease (1) and schizophrenia (2), are thought to be manifestations of imbalances between dopamine receptors and dopamine. The receptors which mediate dopamine's effects have been divided into $D_1$ and $D_2$ subtypes, which are distinguished by their G-protein coupling (3, 4), ligand specificities, anatomical distribution and physiological effects (5). The dopamine $D_2$ receptors have been of particular clinical interest due to their regulation of prolactin secretion (6) and their affinity for antipsychotic drugs (7, 8).

The dopamine $D_2$ receptors belong to the family of G-protein coupled receptors. The sequence similarity shared by members of this family enabled us to clone a rat brain dopamine $D_2$ receptor cDNA (9). We have used that clone to isolate the human pituitary dopamine $D_2$ receptor cDNA described here. We have found that the deduced amino acid sequences of these two receptors are very similar, with one notable difference. The human receptor contains an additional 29 amino acids in its putative third cytoplasmic loop which are encoded by one of the gene's exons. This genomic organization suggests that the existence of two dopamine $D_2$ receptor mRNAs is the result of an alternative splicing event.

Materials and Methods

Cloning of the Human Pituitary cDNA

Human pituitary tissue was a generous gift from Drs. N. Seidah and M. Chretien, Clinical Research Institute of Montreal, Canada. Poly(A)+ mRNA and cDNA were prepared as previously described (9). The cDNA was size-selected (1–6 kb) on agarose gels, isolated using Geneclean (Bio 101), ligated to EcoRI adaptors, cloned into λGT10 arms (Stratagene), and packaged (Gigapak Gold). Recombinants ($1.5 \times 10^6$) were screened on replica nylon filters (DuPont PlaquetColony Hybridization filters) with [32P]-labelled hybridization probes. Prehybridization and hybridization were performed in 50% formamide, 1% SDS, 2×SSC (1×SSC=0.15 M NaCl/0.015 M sodium citrate, pH 7) at 37° C. The complete sequence of both strands of DNA were determined in M13 mp19 using Sequenase (U.S. Biochemical) primed with synthetic oligonucleotides.

Expression and Pharmacoloqy

The 2.5-kb human pituitary cDNA (hPitD$_2$) was cloned into pZem3 (a gift from Dr. E. Mulvihill, Zymogenetics) and co-transfected with the pRSVneo gene into mouse Ltk⁻ cells by $CaPO_4$ precipitation (10). A stable transfectant (L-hPitD$_2$Zem) was selected and maintained in 750 μg/ml of G418 (Geneticin sulphate, Gibco). Twenty hours prior to the harvesting of membranes, these cells were incubated with 70 μM zinc sulphate. Membranes were prepared from L-HPitD$_2$Zem, from the Ltk⁻ cell line expressing the cloned rat dopamine $D_2$ receptor (L-RGB2Zem-1) and from freshly dissected rat striata (Taconic Farm, Germantown, N.Y.), as previously described (11, 12). For the binding assays, membrane protein was used at 10–15 μg from L-hPitD$_2$Zem, 50–75 μg from L-RGB2Zem-1, and 220–250 μg from rat striatum. The binding assays were incubated at 37° C. for 60 minutes in 50 mM Tris-HCl, 120 mM NaCl, 5 mM KCl, 2 mM $CaCl_2$, 1 mM $MgCl_2$, pH 7.4, and then stopped by rapid filtration over glass fiber filters (Schleicher and Schuell, No. 32) which had been presoaked in 0.5% polyethyleneimine. The filters were washed twice in ice cold 50 mM Tris-HCl, pH 7.4. Saturation curves were generated using increasing concentrations of the highly $D_2$-specific antagonist [³H]-domperidone (13). Antagonist drugs were evaluated for their ability to inhibit specifically bound [³H]-domperidone (1 nM). The $B_{max}$, $K_d$, and $IC_{50}$ values were determined as previously described (14).

Southern Blotting

Human genomic DNA prepared from a normal male donor was a gift from M. Litt. Three micrograms of DNA were digested with restriction enzymes and the fragments were electrophoresed in 0.7% agarose and blotted onto nitrocellulose filters (Schleicher and Schuell). Prehybridization and hybridization were performed at 37° C. in 50% formamide as previously described (15).

Genomic Sequencing

Genomic bacteriophage lambda libraries, prepared from normal human male DNA, were purchased from Stratagene and Clontech Laboratories, Inc. and screened with portions of the cloned rat dopamine $D_2$ receptor cDNA. DNA sequence was determined by a genomic sequencing approach (16, 17). Briefly, for each restriction enzyme used, cloned genomic phage DNA (50 μg) was digested, subjected to chemical cleavage, and the resulting fragments resolved in a denaturing polyacrylamide gel. The DNA was then transferred from the gel and immobilized onto nylon filters (Plasco Genetran). Using [³²P] end-labelled synthetic oligomers, ladders of sequence were visualized within exons and read into neighboring introns. The filters were then either reprobed with a different oligomer, or a new filter was made in order to read the complementary sequence back across the exon. Both strands of the coding region were sequenced.

Results

Cloning and Sequence Analysis of the Human Pituitary cDNA

Using the rat brain $D_2$ receptor cDNA as probe, three partial cDNAs were isolated from a human pituitary library and secuenced. Two oligonucleotide probes based on these sequences were used to isolate a fourth cDNA, hPitD$_2$, which encoded a full-length receptor protein (FIG. 18). The human pituitary receptor contains seven putative transmembrane domains and lacks a signal sequence. Overall, the human and rat nucleotide seqiences are 90% similar and show 96% identity at the amino acid level. Several consensus sequences for N-linked glycosylation, protein kinase A phosphorylation and palmitoylation (18) are conserved between the human and rat receptors. There are also 18 amino acid differences (including one deletion) between these proteins, and, strikingly, the human pituitary receptor contains an additional 29 amino acids in its putative third cytoplasmic loop.

Expression and Pharmacological Evaluation of hpit $D_2$ cDNA

In order to evaluate the pharmacological characteristics of the human pituitary receptor, its cDNA was subcloned into pZem3 and expressed in mouse Ltk⁻ cells (L-hPitD$_2$Zem). Membranes prepared from these cells showed specific binding of [$^3$H]-domperidone, a $D_2$-selective antagonist (12, 13), with a $B_{max}$ of 4.05+/−0.3 pmol per mg (n=2) protein and a $K_d$ of 0.74+/−0.11 nM (n=2). This $K_d$ value is in excellent agreement with the published value of 0.74 nM in mouse brain membranes (13). A Scatchard plot of the data was linear. There was no detectable [$^3$H]-domperidone binding in membranes prepared from cells transfected with pZem3 alone (data not shown). [$^3$H]-domperidone binding to L-hPitD$_2$Zem membranes was inhibited by a number of dopamine $D_2$-specific drugs (FIG. 19). Their rank order of potency was: spiperone, (+)-butaclamol, haloperidol, and sulpiride. The serotonin-selective antagonist mianserin and the $D_1$-selective antagonist SCH-23390 inhibited domperidone binding only at very high concentrations, as did the inactive isomer (−)-butaclamol. These values are essentially identical to those obtained with membranes from Ltk⁻ cells transfected with the cloned rat dopamine $D_2$ receptor cDNA (L-RGB2Zem-1) and from rat striatum (FIG. 22).

Human Dopamine $D_2$ Receptor Gene

Using portions of the rat cDNA as probe, a clone was isolated from a human genomic library. This genomic clone, λHD2G1, contained a 1.6-kb BamHI fragment which encoded the last 64 amino acids of the human $D_2$ receptor and 1.2-kb of 3' non-coding sequence. The 1.6-kb fragment was used to probe a Southern blot of human genomic DNA digested with three restriction enzymes. Each enzyme generated a single fragment that hybridized to the probe (FIG. 20), indicating that there is probably only one human dopamine $D_2$ receptor gene.

In order to isolate a genomic clone that encoded the N-terminus of the human receptor protein, a 118-bp restriction fragment from the cloned rat dopamine $D_2$ receptor cDNA (corresponding to amino acid residues 1–39) was used to screen a second genomic library. λHD2G2 was isolated and found to overlap with λHD2G1 by 400 nucleotides (FIG. 21a). Together, these phage span 34-kb of the human dopamine $D_2$ receptor gene locus, DRD2 (19), and contain the sequence found in the hPitD$_2$ cDNA plus sequences that extend 15-kb downstream of the polyadenylation signal and 3.7-kb upstream of the translation initiation site. To characterize the intron/exon structure of the gene, a genomic sequencing approach employing oligonucleotide probes and chemical cleavage was used (FIG. 21b). Since the divergence of nucleotide sequences between human and rat members of this receptor family is approximately 10% (unpublished observations), we were able to initiate genomic sequencing relying on hybridization probes and restriction sites that are present in the cloned rat dopamine $D_2$ receptor cDNA. Our results demonstrate that the coding portion of the human dopamine $D_2$ receptor gene is divided into seven exons (FIG. 21b). Interestingly, we found that exon five is 87-bp long and encodes the entire 29 amino acid sequence present in the cloned human pituitary receptor (FIGS. 18 and 21c). Analysis of the six introns revealed that each contains acceptor and donor sequences that conform to the GT/AG rule (20), as summarized in FIG. 23. The approximate sizes of the introns were based on the results of Southern blotting experiments (data not shown). When compared, the genomic and cDNA sequences were found to differ by only two silent transitions, one at 939 (T to C in the gene) and the other at 957 (C to T in the gene).

Discussion

Several alternative hypotheses might account for the extra sequence present in our human pituitary $D_2$ receptor cDNA clone. One possibility is that the human gene contains the extra 87 bases and that the rat gene does not. Another is that both human and rat have two distinct genes which code for two different dopamine $D_2$ receptors. Finally, alternative splicing of a single transcript could result in one mRNA and the other without the 87 bases. In support of the latter hypothesis, we have shown that there is probably only one human dopamine $D_2$ receptor gene, DRD2, and that the 87-bp sequence is contained on a distinct exon of that gene. Furthermore, we have cloned a rat brain cDNA that contains the 87-bp sequence (unpublished results). This sequence is highly similar to that of the human cDNA and established that dopamine $D_2$ receptors containing the 29 residues are not unique to the human pituitary.

The human dopamine $D_2$ receptor expressed in L-hpitD$_2$Zem cells has essentially the same drug binding profile as do rat striatum and L-RGB2Zem-1 membranes. Therefore, since the 29 amino acids do not affect binding, they may be involved in other levels of receptor function. For example, the third cytoplasmic loop of the $\beta_2$-adrenergic receptor has been shown to be required for appropriate G-protein coupling (21). Therefore, one possibility is that this sequence may influence whether dopamihe $D_2$ receptor stimulation inhibits adenylyl cyclase, activates potassium channel conductance or inhibits calcium mobilization (22). Another possibility is that the 29 amino acids differentiate post-synaptic dopamine $D_2$ receptors from presynaptic autoreceptors (23). Since a computer search (VAX/Intelligenetics) failed to identify another sequence of significant homology, we consider this sequence to be unique to the $D_2$ receptor.

Based on the comparison of genomic and cDNA sequences, the human dopamine $D_2$ receptor gene is divided into at least seven exons. It is possible that one or more additional exons remain to be identified at the 5' end of the gene, as was shown to be the case with muscarinic receptor genes (24).

The interruption of coding sequence by introns distinguishes the human dopamine $D_2$ receptor gene from most other members of the G-protein coupled receptor gene family with the exception of the opsin genes (25). One significant observation is that the placement of two introns (Nos. 3 and 5) in this human gene corresponds almost precisely to intron positions conserved in bovine and Drosophila opsin genes (26, 27). The simplest interpretation of this finding is that their common ancestor, a gene rougly one billion years old (28), contained these introns. Our characterization of the gene structure also provides evidence that the exons encode recognizable elements of protein structure (29). That introns are found following transmembrane segments II, III, and IV (See FIGS. 18 and 21) argues that the repeated structural motifs characteristic of these receptors may have evolved by internal duplication. Furthermore, the presence of several introns within the third cytoplasmic loop provides an explanation of the substantial variation in length observed across the family (30).

The possibility of alternatively spliced dopamine $D_2$ receptdr mRNAs giving rise to structurally distinct forms is exciting. The expression of one form of the.dopamine $D_2$ receptor mRNA or another represents a level of control which may have implications with respect to human disease.

ACKNOWLEDGEMENTS

We would like to thank Howard Goodman for discussion and review of the manuscript, Dee Yarozeski for manuscript preparation, and Vicky Robertson, Nancy Kurkinen, and June Shiigi for the illustrations. D. K. G. holds a fellowship from NIH. This work was supported by NIH Grant Nos. Dk37231 and MH45614 and a grant from Cambridge NeuroScience Research, Inc., Cambridge, Mass., to O.C.

REFERENCES

1. Lee, T., Seeman, P., Rajput, A., Farley, I. J. and Hornykiewicz, O. (1978) Nature 273, 59–61.
2. Seeman, P., Ulpian, G., Bergeron, C., Riederer, P., Jellinger, K., Gabriel, E., Reynolds, G. P. and Tourtellotte, W. W. (1984) Science 225, 728–730.
3. Kebabian, J. W. (1978) Adv. Biochem. Psychopharmacol. 19, 131–154.
4. DeCamilli, P., Maconi, D. and Spada, A. (1979) Nature (London) 278, 252–255.
5. Clark, D. and White, F. J. (1987) Synapse 1, 347–388.
6. Weiner, R. I. and Ganong, W. (1978) Physiol. Rev. 58, 905–976.
7. Seeman, P. and Lee, T. (1975) Science 188, 1217–1219.
8. Creese, I., Burt, D. R., and Snyder, S. H. (1976) Science 192, 481–483.
9. Bunzow, J. R., Van Tol, H. H. M., Grandy, D. K., Albert, P. R., Salon, J., Christie, M., Machida, C. A., Neve, K., and Civelli, O. (1988) Nature 336, 783–787.
10. Gorman, C., Padmanabhan, R. and Howard, B. H. (1983) Science 221, 551–553.
11. Albert, P. R., Neve, K., Bunzow, J. R. and Civelli, O. (1989) submitted.
12. Grigoriadis, D. and Seeman, P. (1986) Naunyn-Schmiederberg Arch. Pharmacol. 321, 21–25.
13. Baudry, M., Martres, M. P. and Schwartz, J. C. (1979) Naunyn-Schiederberg Arch. Pharmacol. 308, 231–237.
14. Fischer, J. B. and Schonbrunn, A. (1988) J. Biol. Chem. 263 2808–2816
15. Grandy, D. K. and Dodgson, J. B. (1987) Nuc. Acids Res. 15, 1063–1080.
16. Church, G. M. and Gilbert, W. (1984) Proc. Natl. Acad. Sci. USA 81, 1991–1995.
17. Marchionni, M. and Gilbert, M. (1986) Cell 46, 133–141.
18. O'Dowd, B. F., Hnatowich, M., M. C. G., Lefkowitz, R. J. and Bouvier, M. (1989) J. Biol. Chem. 264, 7564–7569.
19. Grandy, D. K., Litt, M., Allen, L., Bunzow, J. R., Marchionni, M. A., Makam, H., Frothingham, L., Magenis, R. E. and Civelli, 0. (1989) Am. J. Hum. Genet. accepted.
20. Mount, S. M. (1982) Nuc. Acids Res. 10, 461–472.
21. Strader, C. D., Dixon, R. A. F., Cheung, A. H., Candelore, M. R., Blake, A. D. and Sigal, I. S. (1987) J. Biol. Chem. 262, 16439–16443.
22. Vallar, L. and Meldolesi, J. (1989) TiPS 10, 74–77.
23. Tepper, J. M., Gariano, R. F. and Groves, P. M. (1987) in *Neurophysioloqv of Dopaminergic Systems: Current Status and Clinical Perspectives*, eds. Chiodo, L. A. and Freeman, A. S. (Lakeshore Publishing Co., Michigan), pp. 93–127.
24. Peralta, E. G., Winslow, J. W., Peterson, F. L., Smith, D. H., Ashkenazi, Avi, Ramachandran, J., Schimerlik, M. I. and Capon, D. J. (1987) Science 236, 600–605.
25. O'Dowd, B. F., Lefkowitz, R. J. and Caron, M. G. (1989) Ann. Rev. Neurosci. 12, 67–83.
26. Nathans, J. and Hogness, D. S. (1983) Cell 32, 807–814.
27. O'Tousa, J. E., Baehr, W., Martin, R. L., Hirsch, J., Pak, W. L. and Applebury, M. L. (1985) Cell 40, 839–850.
28. Doolittle, R. F. (1987) *Of URFS and ORFS* (University Science Books, Mill Valley), p. 40.
29. Gilbert, W. (1978) Nature 271, 501.
30. Dohlman, H. G., Caron, M. G. and Lefkowitz, R. J. (1987) Biochem. 26, 2657–2664.

What is claimed is:

1. A method of isolating a DNA molecule having a DNA sequence coding for a mammalian G-protein coupled receptor, comprising hybridizing a first portion of a mammmalian DNA sample with a detectably labeled probe comprising a DNA molecule coding for one or more peptides having an amino acid sequence of a transmembrane domain selected from domains I–VII of a polypeptide of FIG. 2, or a DNA molecule complementary thereto, under low stringency conditions, isolating a DNA molecule from the DNA sample which hybridizes with the probe, and, hybridizing the DNA sample under high stringency conditions with a detectably labeled oligonucleotide probe, comprising an oligonucleotide having a nucleotide sequence that is capable of hybridizing under high stringency conditions to a DNA moecule coding for a transmembrane domain selected from domains I–VII of FIGS. 18A–D and 18G–H of either rat or human origin, or a DNA molecule complementary thereto, and isolating the thus-identified DNA molecule encoding a mammalian G-protein coupled receptor.

2. An isolated DNA molecule comprising
a) a DNA molecule having the sequence of FIGS. 7A–C,
b) a DNA molecule having the DNA sequence 1–1245 of FIGS. 1A–E,
c) a DNA molecule having the DNA sequence 1–1323 of the human DNA sequence of FIGS. 18A–H,
d) a DNA molecule having the DNA sequence 1–723 and 811–1323 of the human DNA sequence of FIGS. 18A–H, corresponding to nucleotides 1–1323 of the human DNA sequence of FIGS. 18A–H, wherein the nucleotide sequence 724–810 of the human is deleted therefrom,
e) a DNA molecule having a DNA sequence complementary to a), b), c), or d),
f) a DNA molecule that hybridizes under high stringency conditions to a), b), c), or d), or
d) a DNA molecule encoding an amino acid sequence identified as the amino acid sequence of FIGS. 7A–C. FIGS. 18A–H or FIGS. 18A–H wherein amino acids 246–272 are deleted therefrom.

3. A method of producing a mammalian G-protein couple D2 dopamine receptor polypeptide, comprising expressing a DNA molecule encoding an amino acid sequence identified as the amino acid sequence of FIGS. 1A–E, FIGS. 18A–H or FIGS. 18A–H wherein amino acids 246–272 are deleted therefrom, operably linked to control sequences, in a suitable host, and isolating the thus-produced polypeptide.

4. An isolated DNA molecule comprising
a) a DNA molecule having the sequence of FIGS. 7A–C,
b) a DNA molecule having a DNA sequence complementary to a), or
c) a DNA molecule that hybridizes under high stringency conditions to either a) or b).

5. An isolated DNA molecule of claim 4, wherein the DNA is isolated from a human.

6. An isolated DNA molecule of claim 4, wherein the DNA is isolated from a rat.

7. An isolated DNA molecule comprising
a) a DNA molecule having the sequence 1–1245 of FIGS. 1A–E,
b) a DNA molecule having a DNA sequence complementary to a), or
c) a DNA molecule that hybridizes under high stringency conditions to either a) or b).

8. An isolated DNA molecule of claim 7, having a DNA sequence identical with a protein coding sequence isolated from a rat.

9. An isolated DNA molecule comprising
a) a DNA molecule having the sequence 1–1323 of the human DNA sequence of FIGS. 18A–H,
b) a DNA molecule having a DNA sequence complementary to a), or
c) a DNA molecule that hybridizes under high stringency conditions to either a) or b).

10. An isolated DNA molecule of claim 9 having a DNA sequence that is nucleotides 1–1323 of the human sequence of FIGS. 18A–H.

11. An isolated DNA molecule of claim 9, having a DNA sequence identical with a protein coding sequence isolated from a human.

12. An isolated DNA molecule comprising
a) a DNA molecule having the DNA sequence 1–723 and 811–1323 of the human DNA sequence of FIGS. 18A–H, corresponding to nucleotides 1–1323 of the human DNA sequence of FIGS. 18A–H, wherein the nucleotide sequence 724–810 of the human is deleted therefrom,
b) a DNA molecule having a DNA sequence complementary to a), or
c) a DNA molecule that hybridizes under high stringency conditions to either a) or b).

13. An isolated DNA molecule of claim 12, having a DNA sequence identical with a protein coding sequence isolated from a human.

14. A reagent for preparing a nucleic acid hybridization probe comprising an oligonucleotide that hydridizes under high stringency conditions to
a DNA molecule having the nucleotide sequence of the naturally occurring DNA sequence coding for a transmembrane domain selected from domains I–VII of FIGS. 18A–D and 18G–H of either rat or human origin, or
a DNA molecule complementary thereto.

15. A nucleic acid hybridization probe comprising the reagent of claim 14 labeled with a detectable label moiety.

16. A reagent for preparing a nucleic acid hybridization probe comprising an oligonucleotide that hydridizes under high stringency conditions to
a DNA molecule having the nucleotide sequence of FIGS. 1A–E or FIGS. 18A–J which codes for a transmembrane domain selected from domains I–VII of FIGS. 18A–D and 18G–H, selected from sequences identical with or corresponding to nucleotides 112–180 (I), 214–291 (II), 325–290 (III), 454–522 (IV), 559–630 (V), 1120–1191 (IV) and 1216–1287 (VII) of $D_2$ dopamine receptor cDNA, of either rat or human origin, or
a DNA molecule complementary thereto.

17. A nucleic acid hybridization probe comprising the reagent of claim 16 labeled with a detectable label moiety.

18. A vector comprising a DNA molecule having the sequence of FIGS. 7A–C, or a DNA molecule that hybridizes under high stringency conditions to a DNA molecule having a DNA sequence complementary thereto.

19. A vector of claim 18, wherein the DNA molecule encoding a mammalian $D_2$ dopamine receptor is operably linked to an expression control sequence.

20. A cell transformed with a vector of claim 19.

21. A vector comprising a DNA molecule having the DNA sequence 1–1245 of FIGS. 1A–E, or a DNA molecule that hybridizes under high stringency conditions to a DNA molecule having a DNA sequence complementary thereto.

22. ///

23. A vector of claim 21, wherein the DNA molecule encodes a mammalian $D_2$ dopamine receptor and is operably linked to an expression control sequence.

24. A cell transformed with a vector of claim 23.

25. A vector comprising a DNA molecule having the DNA sequence 1–1323 of the human DNA sequence of FIGS. 18A–H, or a DNA molecule that hybridizes under high stringency conditions to a DNA molecule having a DNA sequence complementary thereto.

26. A vector of claim 25, wherein the DNA molecule encodes a mammalian G-protein coupled D2 dopamine receptor and is under the control of a viral promoter.

27. A vector of claim 26, which is a vaccinia virus or retrovirus.

28. A cell transformed with the vector of claim 26.

29. A cell transformed with vector of claim 25.

30. A cell of claim 28, wherein the mammal is human.

31. A cell of claim 28, from a multicellular organism.

32. A cell of claim 28, wherein the cell is a mammalian cell.

33. A vector of claim 25, wherein the DNA molecule encodes a mammalian $D_2$ dopamine receptor and is operably linked to an expression control sequence.

34. A cell transformed with a vector of claim 33.

35. A vector comprising a DNA molecule having the DNA sequence 1–723 and 811–1323 of the human DNA sequence of FIGS. 18A–H, corresponding to nucleotides 1–1323 of the human DNA sequence of FIGS. 18 A–H, wherein the nucleotide sequence 724–810 of the human is deleted therfrom, or a DNA molecule the hybrizes under high stringency conditions to a DNA molecule having a DNA sequence complementary thereto.

36. A cell transformed with vector of claim 35.

37. A vector of claim 35, wherein the DNA molecule encodes a mammalian $D_2$ dopamine receptor and is operably linked to an expression control sequence.

38. A cell transformed with a vector of claim 37.

39. A vector of claim 35, wherein the DNA molecule encodes a mammalian G-protein coupled $D_2$ dopamine receptor and is under the control of a viral promoter.

40. A cell transfromed with the vector of claim 39.

41. A method for preparing a G-proteim coupled $D_2$ dopamine receptor polypeptide, comprising culturing a cell under expression conditions, wherein the cell is transformed with a vector comprising a DNA molecule having the DNA sequence 1–1323 of the human DNA sequence of FIGS. 18A–H.

42. A method for preparing a G-proteim coupled D2 dopamine receptor polypeptide, comprising culturing a cell under expression conditions, wherein the cell is transformed with a vector comprising a DNA molecule having the DNA sequence 1–723 and 811–1323 of the human DNA sequence of FIGS. 18A–H, coresponding to nucleotides 1–1323 of the human DNA sequence of FIG. 18A–H, wherein the nucleotide sequence 724–810 of the human is deleted therefrom.

43. A method for preparing an islated G-protein coupled $D_2$ dopamine receptor protein, comprising
  culturing, under expression conditions, host cells containing an isolated cDNA encoding a mammalian G-protein coupled $D_2$ dopamine receptor operably linked to an expression control sequence wherein the host cells produce the dopamine $D_2$ receptor, wherein said cDNA is selected from the group consisting of:
  a) a DNA molecule having the DNA sequence 1–1245 of FIGS. 1A–E;
  b) a DNA molecule having the DNA sequence 1–1323 of the human DNA sequence of FIGS. 18A–H;
  c) a DNA molecule having the DNA sequence 1–723 and 811–1323 of the human DNA sequence of FIGS. 18A–H, corresponding to nucleotides 1–1323 of the human DNA sequence of FIGS. 18A–H, wherein the nucleotide sequence 724–810 of the human is deleted therfrom; and isolatign the G-protein coupled $D_2$ dopamine receptor from the host cells.

44. A method for producing a mammalian G-protein coupled $D_2$ dopamine receptor polypeptided, comprising expressing a DNA molecule having the DNA sequence 1–1245 of FIGS. 1A–E operably linked to an expression control sequence in a suitable host and isolating the thus-produced the polypeptide.

45. A method for producing a mammalian G-protein coupled $D_2$ dopamine receptor polypeptided, comprising expressing a DNA molecule having the DNA sequence 1–1323 of the human DNA sequence of FIGS. 18A–H operably linked to an expression control sequence in a suitable host and isolating the thus-produced the polypeptide.

46. A method for producing a mammalian G-protein coupled $D_2$ dopamine receptor polypeptided, comprising expressing a DNA molecule having the DNA sequence 1–723 and 811–1323 of the human DNA sequence of FIGS. 18A–H, corresponding to nucleotides 1–1323 of the human DNA sequence of FIGS. 18A–H, wherein the nucleotide sequence 724–810 of the human id deleted therefrom operably linked to an expression control sequence in a suitable host and isolating the thus-produced the polypeptide.

47. A method of isolating a cDNA molecule having a DNA sequence encoding a mammalian G-protein coupled $D_2$ dopamine receptor, comprising the steps of
  a) preparing cDNA from a a mammalian tissue which expresses G-protein couple dopamine $D_2$ receptor,
  b) inserting the cDNA into plasmids and transforming suitable host cells to produce transformed cells containing said cDNA, and
  c) isolating a clone of said transformed cells which contains a cDNA molecule encoding a G-protein coupled dopamine $D_2$ receptor by a process comprising:
    hybridizing samples of clones of the transformed host cells under high stringency conditions with a detectably labeled nucleic acid hybridization probe comprising a nucleic acid coding for one or more peptides having a amino acid sequence of a transmembrane domain selected from domains I–VII of a polypeptide of FIG. 2, or to a DNA molecule complementary thereto.

48. The method of claim 47, further comprising the step of
  identifying clones from among the clones identified in step (c) which contain a cDNA encoding a G-protein coupled dopamine $D_2$ receptor receptor by screening the expression products of said cDNA molecule made in a suitable host cell fro $D_2$ dopamine receptor biological activity, and isolating the thus-identified DNA molecules therefrom.

* * * * *

UNITED STATES PATENT AND TRADEMARK OFFICE
CERTIFICATE OF CORRECTION

PATENT NO. : 6,277,591 B1
DATED : August 21, 2001
INVENTOR(S) : Olivier Civelli, James R. Bunzow, David K. Grandy and Curtis A. Machida It is certified that error appears in the above-identified patent and that said Letters Patent is hereby corrected as shown below:

Column 42,
Lines 46, 49 and 50, delete "1323" and insert therefor -- 1329 --.

Column 43,
Lines 25, 32, 39 and 40, delete "1323" and insert therefor -- 1329 --.

Column 44,
Lines 29, 49 and 50, delete "1323" and insert therefor -- 1329 --.

Column 45,
Lines 2, 8, 9, 21, 24, 25 and 39, delete "1323" and insert therefor -- 1329 --.

Column 46,
Line 4, delete "1323" and insert therefor -- 1329 --.
Line 5, delete "1323" and insert therefor -- 1329 --.

Signed and Sealed this

Twenty-first Day of May, 2002

Attest:

JAMES E. ROGAN
Director of the United States Patent and Trademark Office

Attesting Officer